United States Patent
Magnani et al.

(10) Patent No.: US 11,712,446 B2
(45) Date of Patent: *Aug. 1, 2023

(54) METHODS OF MOBILIZING MARROW INFILTRATING LYMPHOCYTES AND USES THEREOF

(71) Applicant: GLYCOMIMETICS, INC., Rockville, MD (US)

(72) Inventors: John L. Magnani, Gaithersburg, MD (US); William Fogler, Baltimore, MD (US)

(73) Assignee: GLYCOMIMETICS, INC., Rockville, MD (US)

( * ) Notice: Subject to any disclaimer, the term of this patent is extended or adjusted under 35 U.S.C. 154(b) by 381 days.

This patent is subject to a terminal disclaimer.

(21) Appl. No.: 16/767,698

(22) PCT Filed: Nov. 29, 2018

(86) PCT No.: PCT/US2018/062988
§ 371 (c)(1),
(2) Date: May 28, 2020

(87) PCT Pub. No.: WO2019/108750
PCT Pub. Date: Jun. 6, 2019

(65) Prior Publication Data
US 2021/0177878 A1    Jun. 17, 2021

Related U.S. Application Data

(60) Provisional application No. 62/592,686, filed on Nov. 30, 2017.

(51) Int. Cl.
*A61K 31/7034* (2006.01)
*A61P 35/00* (2006.01)
*A61K 35/17* (2015.01)
*A61K 38/19* (2006.01)

(52) U.S. Cl.
CPC .......... *A61K 31/7034* (2013.01); *A61K 35/17* (2013.01); *A61K 38/193* (2013.01); *A61P 35/00* (2018.01)

(58) Field of Classification Search
None
See application file for complete search history.

(56) References Cited

U.S. PATENT DOCUMENTS

| | | |
|---|---|---|
| 4,471,057 A | 9/1984 | Koprowski et al. |
| 4,851,511 A | 7/1989 | Hakomori et al. |
| 4,859,769 A | 8/1989 | Karlsson et al. |
| 4,876,199 A | 10/1989 | Hakamori |
| 4,925,796 A | 5/1990 | Bergh et al. |
| 4,946,830 A | 8/1990 | Pulverer et al. |
| 5,143,712 A | 9/1992 | Brandley et al. |
| 5,151,360 A | 9/1992 | Handa et al. |
| 5,211,937 A | 5/1993 | Brandley et al. |
| 5,268,364 A | 12/1993 | Kojima et al. |
| 5,304,640 A | 4/1994 | Lasky et al. |
| 5,352,670 A | 10/1994 | Venot et al. |
| 5,369,096 A | 11/1994 | Yamada et al. |
| 5,412,123 A | 5/1995 | Rao et al. |
| 5,444,050 A | 8/1995 | Kogan et al. |
| 5,464,778 A | 11/1995 | Cummings et al. |
| 5,464,815 A | 11/1995 | Chamow et al. |
| 5,470,843 A | 11/1995 | Stahl et al. |
| 5,484,891 A | 1/1996 | Lasky et al. |
| 5,486,536 A | 1/1996 | Ward et al. |
| 5,519,008 A | 5/1996 | Rao et al. |
| 5,527,785 A | 6/1996 | Bevilacqua et al. |
| 5,538,724 A | 7/1996 | Butcher et al. |
| 5,559,103 A | 9/1996 | Gaeta et al. |
| 5,576,305 A | 11/1996 | Ratcliffe |
| 5,580,858 A | 12/1996 | Ippolito et al. |
| 5,580,862 A | 12/1996 | Rosen et al. |
| 5,589,465 A | 12/1996 | Ishida et al. |
| 5,604,207 A | 2/1997 | DeFrees et al. |
| 5,618,785 A | 4/1997 | Heavner et al. |
| 5,622,937 A | 4/1997 | Kogan et al. |
| 5,632,991 A | 5/1997 | Gimbrone, Jr. |
| 5,639,734 A | 6/1997 | Esko et al. |
| 5,646,123 A | 7/1997 | Ippolito et al. |
| 5,646,248 A | 7/1997 | Sawada et al. |
| 5,648,344 A | 7/1997 | Brandley et al. |

(Continued)

FOREIGN PATENT DOCUMENTS

| | | |
|---|---|---|
| DE | 2434953 | 2/1975 |
| EP | 319253 A2 | 6/1989 |

(Continued)

OTHER PUBLICATIONS

Noonan et al., "Activated Marrow-Infiltrating Lymphocytes Effectively Target Plasma Cells and Their Clonogenic Precursors", 2005, Cancer Res., 65(5), pp. 2026-2034. (Year: 2005).*
Borrello et al., "Marrow-infiltrating Lymphocytes—role in Biology and cancer therapy", 2016, Front. Immunol., 7:112, pp. 1-7. (doi: 10.3389/fimmu.2016.00112) (Year: 2016).*
Biavati et al., "Activated Allogeneic Donor-derived Marrow-infiltrating Lymphocytes Display Measurable In Vitro Antitumor Activity", Apr. 2019, J. Immunother., 42(3), pp. 73-80 (Year: 2019).*
Muz et al., "Inhibition of E-Selectin (GMI-1271) or Eselectin together with CXCR4 (GMI-1359) re-sensitizes multiple myeloma to therapy", Aug. 2019, 9(68), pp. 1-6. (doi.org/10.1038/s41408-019-0227-3) (Year: 2019).*
Chemical Abstracts (STN), Accession No. 1997:584307, Jul. 8, 1997.

(Continued)

*Primary Examiner* — My-Chau T. Tran
(74) *Attorney, Agent, or Firm* — Finnegan, Henderson, Farabow, Garrett & Dunner LLP

(57) ABSTRACT

Methods are disclosed for the mobilization of marrow infiltrating cells (MILs) using E-selectin antagonists for the treatment of disorders such as cancer. Methods for treating or preventing cancers using MILs mobilized by E-selectin antagonists are further disclosed.

14 Claims, 3 Drawing Sheets

(56) References Cited

U.S. PATENT DOCUMENTS

| | | |
|---|---|---|
| 5,654,282 A | 8/1997 | Tang et al. |
| 5,654,412 A | 8/1997 | Srivastava et al. |
| 5,658,880 A | 8/1997 | Dasgupta et al. |
| 5,663,151 A | 9/1997 | Martel et al. |
| 5,679,321 A | 10/1997 | Dasgupta et al. |
| 5,679,644 A | 10/1997 | Rao et al. |
| 5,686,426 A | 11/1997 | Martel et al. |
| 5,693,621 A | 12/1997 | Toepfer et al. |
| 5,695,752 A | 12/1997 | Rosen et al. |
| 5,710,023 A | 1/1998 | Collins et al. |
| 5,710,123 A | 1/1998 | Heavner et al. |
| 5,723,583 A | 3/1998 | Seed et al. |
| 5,728,685 A | 3/1998 | Abbas et al. |
| 5,739,300 A | 4/1998 | Toepfer et al. |
| 5,747,463 A | 5/1998 | Marinier et al. |
| 5,750,508 A | 5/1998 | Dasgupta et al. |
| 5,753,617 A | 5/1998 | Heavner et al. |
| 5,753,631 A | 5/1998 | Paulson et al. |
| 5,763,413 A | 6/1998 | Numata et al. |
| 5,763,582 A | 6/1998 | Rao et al. |
| 5,789,385 A | 8/1998 | Anderson et al. |
| 5,789,573 A | 8/1998 | Baker et al. |
| 5,795,958 A | 8/1998 | Rao et al. |
| 5,811,404 A | 9/1998 | De Frees et al. |
| 5,811,405 A | 9/1998 | Toepfer et al. |
| 5,817,742 A | 10/1998 | Toepfer et al. |
| 5,817,807 A | 10/1998 | Bridger et al. |
| 5,827,817 A | 10/1998 | Larsen et al. |
| 5,827,837 A | 10/1998 | Bevilacqua et al. |
| 5,830,871 A | 11/1998 | Wong et al. |
| 5,837,689 A | 11/1998 | Anderson et al. |
| 5,837,690 A | 11/1998 | Rao et al. |
| 5,840,679 A | 11/1998 | Larsen et al. |
| 5,854,218 A | 12/1998 | DeFrees |
| 5,856,300 A | 1/1999 | Rittershaus et al. |
| 5,858,983 A | 1/1999 | Seed et al. |
| 5,858,994 A | 1/1999 | Kretzschmar et al. |
| 5,880,091 A | 3/1999 | Cummings et al. |
| 5,916,910 A | 6/1999 | Lai |
| 5,919,768 A | 7/1999 | Korgan et al. |
| 5,919,769 A | 7/1999 | Tsukida et al. |
| 5,962,422 A | 10/1999 | Nagy et al. |
| 5,976,540 A | 11/1999 | Rittershaus et al. |
| 5,977,080 A | 11/1999 | Rosen et al. |
| 5,985,852 A | 11/1999 | Nagy et al. |
| 5,994,402 A | 11/1999 | Rotstein et al. |
| 6,001,819 A | 12/1999 | Simon et al. |
| 6,001,988 A | 12/1999 | Parma et al. |
| 6,033,665 A | 3/2000 | Yednock et al. |
| 6,037,333 A | 3/2000 | Panjwani |
| 6,043,348 A | 3/2000 | Lawman et al. |
| 6,110,897 A | 8/2000 | Unverzagt et al. |
| 6,111,065 A | 8/2000 | Heavner et al. |
| 6,120,751 A | 9/2000 | Unger |
| 6,121,233 A | 9/2000 | Magnani et al. |
| 6,124,267 A | 9/2000 | McEver et al. |
| 6,133,239 A | 10/2000 | Handa et al. |
| 6,133,240 A | 10/2000 | Taylor et al. |
| 6,136,790 A | 10/2000 | Toepfer et al. |
| 6,169,077 B1 | 1/2001 | Oehrlein |
| 6,177,547 B1 | 1/2001 | Cummings et al. |
| 6,187,754 B1 | 2/2001 | Oehrlein |
| 6,193,973 B1 | 2/2001 | Tuttle |
| 6,193,979 B1 | 2/2001 | Rittershaus et al. |
| 6,197,752 B1 | 3/2001 | Schmidt et al. |
| 6,225,071 B1 | 5/2001 | Cummings et al. |
| 6,235,309 B1 | 5/2001 | Nagy et al. |
| 6,280,932 B1 | 8/2001 | Parma et al. |
| 6,287,556 B1 | 9/2001 | Portnoy et al. |
| 6,309,639 B1 | 10/2001 | Cummings et al. |
| 6,372,712 B1 | 4/2002 | Briesewitz |
| 6,387,884 B1 | 5/2002 | Magnani et al. |
| 6,391,857 B1 | 5/2002 | Magnani et al. |
| 6,407,135 B1 | 6/2002 | Lai et al. |
| 6,465,434 B1 | 10/2002 | Magnani et al. |
| 6,492,332 B1 | 10/2002 | Demopulos et al. |
| 6,503,885 B1 | 1/2003 | Kiso et al. |
| 6,506,770 B1 | 1/2003 | Bridger et al. |
| 6,515,117 B2 | 2/2003 | Ellsworth et al. |
| 6,528,487 B1 | 3/2003 | Heavner et al. |
| 6,569,998 B2 | 5/2003 | Cummings et al. |
| 6,592,872 B1 | 7/2003 | Klimpel et al. |
| 6,683,056 B2 | 1/2004 | Washburn et al. |
| 6,756,391 B2 | 6/2004 | Bridger et al. |
| 6,844,125 B2 | 1/2005 | Bistrup et al. |
| 6,872,714 B1 | 3/2005 | Schols |
| 6,875,738 B1 | 4/2005 | Clark-Lewis et al. |
| 6,887,842 B1 | 5/2005 | Briesewitz |
| 6,921,531 B2 | 7/2005 | Briesewitz |
| 6,943,239 B2 | 9/2005 | Holgersson et al. |
| 6,967,093 B2 | 11/2005 | Bistrup et al. |
| 7,060,685 B2 | 6/2006 | Magnani et al. |
| 7,087,212 B2 | 8/2006 | Cantrell et al. |
| 7,160,872 B2 | 1/2007 | Bridger et al. |
| 7,226,949 B2 | 6/2007 | Crooks et al. |
| 7,300,656 B2 | 11/2007 | Ashkenazi et al. |
| 7,361,644 B2 | 4/2008 | Magnani et al. |
| 7,390,784 B2 | 6/2008 | Briesowitz |
| 7,414,065 B2 | 8/2008 | Bridger et al. |
| 7,422,733 B2 | 9/2008 | Ranganathan et al. |
| 7,449,176 B2 | 11/2008 | Ashkenazi et al. |
| 7,517,980 B2 | 4/2009 | Magnani et al. |
| 7,563,760 B2 | 7/2009 | Larsen et al. |
| 7,709,486 B2 | 5/2010 | Bridger et al. |
| 7,728,117 B2 | 6/2010 | Magnani et al. |
| 7,741,312 B2 | 6/2010 | Magnani et al. |
| 7,951,816 B2 | 5/2011 | Kokubo et al. |
| 7,964,569 B2 | 6/2011 | Ernst et al. |
| 7,989,601 B2 | 8/2011 | Magnani et al. |
| 8,026,222 B2 | 9/2011 | Magnani et al. |
| 8,039,442 B2 | 10/2011 | Magnani |
| 8,258,290 B2 | 9/2012 | Magnani et al. |
| 8,361,975 B2 | 1/2013 | Magnani |
| 8,410,066 B2 | 4/2013 | Magnani |
| 8,518,896 B2 | 8/2013 | Magnani et al. |
| 8,530,448 B2 | 9/2013 | Magnani et al. |
| 8,633,303 B2 | 1/2014 | Magnani et al. |
| RE44,778 E | 2/2014 | Magnani et al. |
| 8,895,510 B2 | 11/2014 | Magnani |
| 8,921,328 B2 | 12/2014 | Ernst et al. |
| 9,109,002 B2 | 8/2015 | Magnani et al. |
| 9,254,322 B2 | 2/2016 | Levesque et al. |
| 9,486,497 B2 | 11/2016 | Levesque et al. |
| 9,534,009 B2 | 1/2017 | Magnani |
| 9,796,745 B2 | 10/2017 | Magnani et al. |
| 9,867,841 B2 | 1/2018 | Magnani |
| 11,072,625 B2 * | 7/2021 | Magnani ............... C07H 15/26 |
| 11,197,877 B2 * | 12/2021 | Magnani ............... A61P 35/00 |
| 2001/0046970 A1 | 11/2001 | Nagy et al. |
| 2001/0051370 A1 | 12/2001 | Bistrup et al. |
| 2002/0031508 A1 | 3/2002 | Wagner et al. |
| 2002/0040008 A1 | 4/2002 | Wagner et al. |
| 2002/0086356 A1 | 7/2002 | Tuschi et al. |
| 2002/0128225 A1 | 9/2002 | Liu et al. |
| 2002/0132220 A1 | 9/2002 | Berens et al. |
| 2002/0155429 A1 | 10/2002 | Allaway et al. |
| 2002/0164336 A1 | 11/2002 | Harrison et al. |
| 2002/0164748 A1 | 11/2002 | Bistrup et al. |
| 2002/0165178 A1 | 11/2002 | Schetter et al. |
| 2002/0168366 A1 | 11/2002 | Stewart et al. |
| 2003/0012787 A1 | 1/2003 | Ashkenazi et al. |
| 2003/0012790 A1 | 1/2003 | Ashkenazi et al. |
| 2003/0018181 A1 | 1/2003 | Larsen et al. |
| 2003/0036560 A1 | 2/2003 | Sonis et al. |
| 2003/0039683 A1 | 2/2003 | Cantrell et al. |
| 2003/0073632 A1 | 4/2003 | Ciaccia et al. |
| 2003/0211078 A1 | 11/2003 | Heavner |
| 2004/0067220 A1 | 4/2004 | Sykes |
| 2004/0072796 A1 | 4/2004 | Embury et al. |
| 2004/0096396 A1 | 5/2004 | Magnani et al. |
| 2004/0097403 A1 | 5/2004 | Ranganathan et al. |
| 2004/0219158 A1 | 11/2004 | Magnani |
| 2005/0112124 A1 | 5/2005 | Frenette et al. |
| 2005/0181987 A1 | 8/2005 | Blaszczyk-Thurin et al. |

(56) References Cited

U.S. PATENT DOCUMENTS

| | | |
|---|---|---|
| 2005/0187171 A1 | 8/2005 | Magnani et al. |
| 2005/0214283 A1 | 9/2005 | Sackstein et al. |
| 2006/0194745 A1 | 8/2006 | Magnani et al. |
| 2006/0217303 A1 | 9/2006 | Kriegler |
| 2006/0264451 A1 | 11/2006 | Shim et al. |
| 2006/0287253 A1 | 12/2006 | Kriegler et al. |
| 2007/0021378 A1 | 1/2007 | Varki et al. |
| 2007/0054870 A1 | 3/2007 | Magnani et al. |
| 2007/0054930 A1 | 3/2007 | Shim et al. |
| 2007/0213278 A1 | 9/2007 | Wong et al. |
| 2008/0025992 A1 | 1/2008 | Fabene et al. |
| 2008/0112955 A1 | 5/2008 | Embury et al. |
| 2008/0161546 A1 | 7/2008 | Ernst et al. |
| 2008/0200406 A1 | 8/2008 | Magnani |
| 2008/0227799 A1 | 9/2008 | Liotta et al. |
| 2008/0300220 A1 | 12/2008 | Ranganathan et al. |
| 2008/0306098 A1 | 12/2008 | Mutz et al. |
| 2009/0036386 A1 | 2/2009 | Magnani et al. |
| 2009/0053198 A1 | 2/2009 | Sackstein |
| 2009/0054334 A1 | 2/2009 | Mutz et al. |
| 2009/0175792 A1 | 7/2009 | Magnani et al. |
| 2009/0176717 A1 | 7/2009 | Magnani |
| 2009/0253646 A1 | 10/2009 | Magnani |
| 2009/0312278 A1 | 12/2009 | Magnani et al. |
| 2010/0145032 A1 | 6/2010 | Laine et al. |
| 2010/0215575 A1 | 8/2010 | O'Neill et al. |
| 2010/0240773 A1 | 9/2010 | Korzekwa et al. |
| 2010/0292095 A1 | 11/2010 | Laukkanen et al. |
| 2010/0303766 A1 | 12/2010 | Miyaji et al. |
| 2010/0311105 A1 | 12/2010 | Lu et al. |
| 2011/0002881 A1 | 1/2011 | Levesque et al. |
| 2011/0020270 A1 | 1/2011 | Levesque et al. |
| 2011/0142856 A1 | 6/2011 | Kokubo et al. |
| 2011/0229409 A1 | 9/2011 | Ranganathan et al. |
| 2011/0245265 A1 | 10/2011 | Zuk et al. |
| 2011/0251148 A1 | 10/2011 | Magnani et al. |
| 2011/0257380 A1 | 10/2011 | Ernst et al. |
| 2012/0093782 A1 | 4/2012 | Grove et al. |
| 2012/0129712 A1 | 5/2012 | Satomaa et al. |
| 2012/0202762 A1 | 8/2012 | Magnani |
| 2012/0258043 A1 | 10/2012 | Ranganathan et al. |
| 2012/0329755 A1 | 12/2012 | Magnani et al. |
| 2013/0184229 A1 | 7/2013 | Magnani et al. |
| 2013/0224217 A1* | 8/2013 | Sackstein ............ A61P 9/00 424/158.1 |
| 2013/0261070 A1 | 10/2013 | Magnani et al. |
| 2013/0281646 A1 | 10/2013 | Korzekwa et al. |
| 2013/0331350 A1 | 12/2013 | Ernst et al. |
| 2014/0073594 A1 | 3/2014 | Magnani et al. |
| 2014/0178303 A1 | 6/2014 | Magnani et al. |
| 2015/0051164 A1 | 2/2015 | Magnani |
| 2015/0110808 A1 | 4/2015 | Magnani et al. |
| 2015/0284420 A1 | 10/2015 | Magnani et al. |
| 2016/0145290 A1 | 5/2016 | Magnani et al. |
| 2016/0184339 A1 | 6/2016 | Magnani |
| 2016/0193294 A1 | 7/2016 | Magnani et al. |
| 2016/0243145 A1 | 8/2016 | Magnani et al. |
| 2016/0289257 A1 | 10/2016 | Magnani et al. |
| 2016/0333043 A1 | 11/2016 | Magnani et al. |
| 2017/0305951 A1 | 10/2017 | Magnani et al. |
| 2022/0265693 A1* | 8/2022 | Magnani ............ A61K 31/7052 |

FOREIGN PATENT DOCUMENTS

| | | |
|---|---|---|
| EP | 381310 A1 | 8/1990 |
| EP | 408859 B1 | 1/1991 |
| EP | 671407 A2 | 9/1995 |
| EP | 0 867 722 | 9/1998 |
| JP | 06-0306092 | 11/1994 |
| JP | 9-176047 | 7/1997 |
| JP | 2002-520323 | 7/2002 |
| JP | 2004-518704 | 6/2004 |
| WO | WO 90/13300 | 11/1990 |
| WO | WO 91/19502 | 12/1991 |
| WO | WO 92/01718 | 2/1992 |
| WO | WO 92/07572 | 5/1992 |
| WO | WO 94/25043 | 11/1994 |
| WO | WO 94/26760 | 11/1994 |
| WO | WO 94/29477 | 12/1994 |
| WO | WO 95/00527 | 1/1995 |
| WO | WO 95/03059 | 2/1995 |
| WO | WO 95/29681 | 11/1995 |
| WO | WO 95/31210 | 11/1995 |
| WO | WO 96/20204 | 7/1996 |
| WO | WO 96/25418 | 8/1996 |
| WO | WO 96/26950 | 9/1996 |
| WO | WO 96/40942 | 12/1996 |
| WO | WO 97/01355 | 1/1997 |
| WO | WO 97/01569 | 1/1997 |
| WO | WO 97/14707 | 4/1997 |
| WO | WO 97/28173 | 8/1997 |
| WO | WO 97/28174 | 8/1997 |
| WO | WO 98/06730 | 2/1998 |
| WO | WO 98/13058 | 4/1998 |
| WO | WO 98/046771 | 10/1998 |
| WO | WO 99/42130 | 8/1999 |
| WO | WO 99/43353 | 9/1999 |
| WO | WO 99/43356 | 9/1999 |
| WO | WO 99/065712 | 12/1999 |
| WO | WO 00/02870 | 1/2000 |
| WO | WO 00/050032 | 8/2000 |
| WO | WO 00/066112 | 11/2000 |
| WO | WO 01/89564 | 11/2001 |
| WO | WO 02/22820 | 3/2002 |
| WO | WO 02/062810 | 8/2002 |
| WO | WO 03/032925 | 4/2003 |
| WO | WO 03/055876 | 7/2003 |
| WO | WO 03/088980 | 10/2003 |
| WO | WO 03/097658 | 11/2003 |
| WO | WO 04/004636 | 1/2004 |
| WO | WO 04/033663 | 4/2004 |
| WO | WO 04/058304 | 7/2004 |
| WO | WO 04/094619 | 11/2004 |
| WO | WO 05/016349 | 2/2005 |
| WO | WO 05/046597 | 5/2005 |
| WO | WO 05/046997 | 5/2005 |
| WO | WO 05/051920 | 6/2005 |
| WO | WO 05/054264 | 6/2005 |
| WO | WO 05/058934 | 6/2005 |
| WO | WO 05/085219 | 9/2005 |
| WO | WO 05/116088 | 12/2005 |
| WO | WO 06/017180 | 2/2006 |
| WO | WO 06/022454 | 3/2006 |
| WO | WO 06/062946 | 6/2006 |
| WO | WO 06/074426 | 7/2006 |
| WO | WO 06/074428 | 7/2006 |
| WO | WO 06/089106 | 8/2006 |
| WO | WO 06/127906 | 11/2006 |
| WO | WO 07/021721 | 2/2007 |
| WO | WO 07/022089 | 2/2007 |
| WO | WO 07/022385 | 2/2007 |
| WO | WO 07/028050 | 3/2007 |
| WO | WO 07/033329 | 3/2007 |
| WO | WO 08/008852 | 1/2008 |
| WO | WO 08/008854 | 1/2008 |
| WO | WO 08/011094 | 1/2008 |
| WO | WO 08/060378 | 5/2008 |
| WO | WO 08/100453 | 8/2008 |
| WO | WO 08/109154 | 9/2008 |
| WO | WO 09/011889 | 1/2009 |
| WO | WO 09/073911 | 6/2009 |
| WO | WO 09/073916 | 6/2009 |
| WO | WO 09/126556 | 10/2009 |
| WO | WO 09/152245 | 12/2009 |
| WO | WO 10/126888 | 11/2010 |
| WO | WO 12/037034 | 3/2012 |
| WO | WO 12/045913 | 4/2012 |
| WO | WO 12/061662 | 5/2012 |
| WO | WO 12/151576 | 11/2012 |
| WO | WO 13/096926 | 6/2013 |
| WO | WO 14/070991 | 5/2014 |
| WO | WO 14/089269 | 6/2014 |
| WO | WO 14/149837 | 9/2014 |

(56) References Cited

FOREIGN PATENT DOCUMENTS

| | | |
|---|---|---|
| WO | WO 15/019284 | 2/2015 |
| WO | WO 15/048616 | 4/2015 |
| WO | WO 15/109049 | 7/2015 |
| WO | WO 16/089872 | 6/2016 |
| WO | WO 16/164394 | 10/2016 |
| WO | WO 17/023918 | 2/2017 |
| WO | WO 17/095904 | 6/2017 |
| WO | WO 17/151708 | 9/2017 |
| WO | WO 18/031445 | 2/2018 |
| WO | WO 18/068010 | 4/2018 |
| WO | WO 18/169853 | 9/2018 |

OTHER PUBLICATIONS

Culmer et al., "E-selectin inhibition with GMI-1271 decreases venous thrombosis without profoundly affecting tail vein bleeding in a mouse model," Thrombosis and Haemostasis, 117(6), 1171-1181, 2017.
De Castro et al., "Effects of GMI-1070, a Pan-Selectin Inhibitor, On Pain Intensity and Opioid Utilization in Sickle Cell Disease", Blood, 122(21):775, Nov. 15, 2013.
De Clercq, Erik, "The bicyclam AMD3100 story," Nat. Rev. Drug Disc. 2:581-587, Jul. 2003.
Definition of allogenic. Medline Plus-Merriam-Webster Medical Dictionary (last accessed Jun. 3, 2013).
Definition of syngeneic. Medline Plus-Merriam-Webster Medical Dictionary (last accessed Jun. 3, 2013).
Definition of xenogeneic. Medline Plus-Merriam-Webster Medical Dictionary (last accessed Jun. 3, 2013).
Demain et al. "Natural products for cancer chemotherapy," Microbio. Biotechnol. 4(6): 687-699, 2011.
Devata et al., "First in Human Phase 1 Single Dose Escalation Studies of the E-Selectin Antagonist GMI-1271 Show a Favorable Safety, Pharmacokinetic, and Biomarker Profile," Blood, 126(23), Abstract#1004, Dec. 3, 2015.
Devata et al., First in Human Phase 1 Single Dose Escalation Studies of the E-Selectin Antagonist GMI-1271 Show a Favorable Safety, Pharmacokinetic, and Biomarker Profile, Proceedings of the 57$^{th}$ Annual Meeting of the American Society of Hematology, Abstract #1004, Poster Presentation, Dec. 5, 2015, Orlando, FL.
Devereux, J., et al., "A comprehensive set of sequence analysis programs for the VAX", Nucleic Acids Research 12(1), (1984), 387-395.
Devine, "Rapid Mobilization of CD34+ Cells Following Administration of the CXCR4 Antagonist AMD 3100 to Patients With Multiple Myeloma and Non-Hodgkin's Lymphoma," Journal of Clinical Oncology, 22(6): 1095-1102 (Feb. 23, 2004).
Deweerdt, "Animal models: Towards a myeloma mouse," Nature, 480 (7377): S38-39 (2011).
Diamandis et al., "Reflection on the Discovery of Carcinoembryonic Antigen, Prostate-Specific Antigen, and Cancer Antigens CA125 and CA19-9", Clin Chem, 59(1), Nov. 30, 2012.
Diaz-Ricart et al., "rPSGL-Ig" Drugs of the Future 27(4):346 (2002).
Dimasi et al., "Expression, crystallization and preliminary crystallographic analysis of the extracellular IgV-like domain of the human natural killer cell inhibitory receptor p75/AIRM1," Acta Crystallographica Section D, Biological Crystallography, 59(Pt 10), 1856-1858, 2003.
Dimasi et al., "Structure of the saccharide-binding domain of the human natural killer cell inhibitory receptor p75/AIR1. Erratum,"Acta Crystallographica Section D, Biological Crystallography, 60(Pt 2), Erratta, 401-403, 2004.
Dittmar et al., "Adhesion Molecules and Chemokines: the Navigation System for Circulating Tumor (Stem) Cells to Metastasize in an Organ-Specific Manner," Clin. Exp. Metastasis 25:11-32, 2008.
Doranz et al., "Safe Use of the CSCR4 Inhibitor ALX40-4C in Humans," AIDS Research and Human Retroviruses 17(6):475-486, 2001.

Duijvestijn et al., "High Endothelial Differentiation in Human Lymphoid and Inflammatory Tissues Defined by Monoclonal Antibody HECA-452," Am. J. Path. 130:147-155, 1988.
Dupre et al., "Glycomimetic Selectin Inhibitors: ($\alpha$-D-Mannopyranosyloxy)methylbiphenyls," Bioorganic & Medicinal Chemistry Letters 6(5): 569-572, 1996.
Dutta et al., "E-Selectin Inhibition Mitigates Splenic HSC Activation and Myelopoiesis in Hypercholesterolemic Mice with Myocardial Infarction," Arteriosclerosis, Thrombosis and Vascular Biology, 36(9), 1802-1808, Jul. 2016.
Dykewicz, "Summary of the Guidelines for Preventing Opportunistic Infections among Hematopoietic Stem Cell Transplant Recipients," Clin. Infectious Diseases, 33:139-144, Jul. 15, 2001.
Edgington, "How Sweet It Is: Selectin-Mediating Drugs," Biotechnology 10: 383-389, 1992.
Edwards, "Generally Applicable, Convenient Solid-Phase Synthesis and Receptor Affinities of Octreotide Analogs," J. Med. Chem. 37:3749-3757, 1994.
Egberink et al. "Bicyclams, Selective Antagonists of the Human Chemokine Receptor CXCR4, Potently Inhibit Feline Immunodeficiency Virus Replication," Journal of Virology, 73(8): 6346-6352 (1999).
Eggens et al., "A Role of Carbohydrate—Carbohydrate Interaction in the Process of Specific Cell Recognition During Embryogenesis and Organogenesis: A Preliminary Note," Biochem. Biophys. Res. Common. 158(3):913-920, 1989.
Eggens et al., "Specific Interaction between Le$^x$ and Le$^x$ Determinants. A Possible Basis for Cell Recognition in Preimplantation Embryos and in Embryonal Carcinoma Cells," J. Biol. Chem. 264(16):9476-9484, 1989.
Egger et al. "Nanomolar E-Selectin Antagonists with Prolonged Half-Lives by a Fragment-Based Approach," JACS, 135(26): 9820-9828 (Jul. 2013).
Embury et al., "The contribution of endothelial cell P-selectin to the microvascularflow of mouse sickle erythrocytes in vivo," Blood 104(10):3378-3385, Nov. 15, 2004.
English Abstract for DE 2434953, Feb. 6, 1975.
English Abstract for JP 9-176047, published Jul. 8, 1997.
English Abstract for WO 96/20204, published Jul. 4, 1996.
English Translation of JP 06-0306092, dated Nov. 1, 1994.
Ernst et al., "Design and Synthesis of E-Selectin Antagonists," Chimia 55:268-274, 2001.
Ernst et al., "From carbohydrate leads to glycomimetic drugs," Nature Reviews 8:661-677, Aug. 2009.
Ernst, "Substrate and donor specificity of glycosyl transferases," Glycoconjugate Journal 16: 161-170, 1999.
Esposito et al., "Exploration of a Potent E-selectin Antagonist (GMI-1271) as a Potential Therapeutic for Treating Breast Cancer Metastasis to the Lung and Bone", AACR Annual Meeting 2014, Poster #4039, Apr. 8, 2014.
Esposito et al., "Exploration of a potent E-selectin antagonist (GMI-1271) as a potential therapeutic for treating breast cancer metastasis to the lung and bone," Proceedings of the 105$^{th}$ Annual Meeting of the America Association for Cancer Research, Abstract #4039, Apr. 2-5, 2014, San Diego, CA.
Esposito et al., "Exploration of a potent E-Selectin antagonist (GMI-1271) as a potential novel therapeutic for treating breast cancer metastasis to the bone and lung," Cancer Research, 74 (19 Supplement), Abstract #4039, Oct. 2014.
Faber et al., "The Many Facets of SDF-1a, CXCR4 Agonists and Antagonists on Hematopoietic Progenitor Cells," J. Biomed. & Biotech. Article ID 26065:1-10, 2007.
Faderl et al., "Clofarabine Plus Cytarabine Compared With Cytarabine Alone in Older Patients With Relapsed or Refractory Acute Myelogenous Leukemia: Results From the Classic I Trial," Journal of Clinical Oncology, 30(20), 2492-2499, 2012.
Feizi et al., "Neoglycolipids: Probes of Oligosaccharide Structure, Antigenicity, and Function," Methods in Enzymology, vol. 230, 1994, pp.
Feletou, M. et al., "Endothelial dysfunction: a multifaceted disorder," Am. J. Physiol. Heart Circ. Physiol., 291: H985-H1002 (2006).

(56) References Cited

OTHER PUBLICATIONS

Fenderson et al., "A Multivalent Lacto-N-Fucopenataose III-Lysyllysine Conjugate Decompacts Preimplantation Mouse Embryos, While the Free Oligosaccharide is Ineffective," J. Exp. Med. 160:1591-1596, 1984.
Fenderson et al., "Coordinate Expression of X and Y Haptens during Murine Embryogenesis," Devel. Biol. 114:12-21, 1986.
Fenderson et al., "The blood group I antigen defined by monoclonal antibody C6 is a marker of early mesoderm during murine embryogenesis," Differentiation 38:124-133, 1988.
Filser, C. et al., "Synthetic glycopeptides from the E-selectin ligand 1 with varied sialyl Lewis(x) structure as cell-adhesion inhibitors of E-selectin," Angewandte Chemie—International Edition, 46(12): 2108-2111 (2007).
Flanner et al., "Comparison of Predicted GMI-1070 Human Intravenous Pharmacokinetics from in silico PBPK and Allometric Scaling Models", AAPS Annual Meeting, Abstract, Nov. 2009.
Flanner et al., "Single Ascending Dose Pharmacokinetics of the E-Selectin/CXCR4 Dual Antagonist GMI-1359 After Intravenous Infusions of 0.1, 0.2, 0.5, 1, 2, and 3.5 mg/kg to Healthy Volunteers," Proceedings of the American College of Clinical Pharmacology Annual Meeting, Sep. 23-25, 2018, Bethesda, MD.
Fogler et al., "Combination of a Glycomimetic Antagonist to E-Selectin and CXCR4, GMI-1359, with an Anti-PD-L1 Antibody Attenuates Regulatory T Cell Infiltration and Accelerates Time to Complete Response in the Murine CT26 Tumor Model," Proceedings of the 31$^{st}$ Annual Meeting of the Society for Immunotherapy of Cancer, Poster Presentation, #P204, Nov. 9-13, 2016, National Harbor, MD.
Fogler et al., "Combination of a glycomimetic antagonist to E-selectin and CXCR4, GMI-1359, with an anti-PD-L1 antibody attenuates regulatory T cell infiltration and accelerates time to complete response in the murine CT26 tumor model," Journal of ImmunoTherapy of Cancer, 4(Supplement 1), 73, P204, Nov. 16, 2016.
Fogler et al., "Administration of the Dual E-Selectin/CXCR4 Antagonist, GMI-1359, Results in a Unique Profile of Tumor Mobilization from the Bone Marrow and Facilitation of Chemotherapy in a Murine Model of FLT3 ITD AML," Blood, 128(22), Abstract #2826, Dec. 2, 2016.
Fogler et al., "Administration of the Dual E-Selectin/CXCR4 Antagonist, GMI-1359, Results in a Unique Profile of Tumor Mobilization from the Bone Marrow and Facilitation of Chemotherapy in a Murine Model of FLT3 Itd Aml," Proceedings of the 58th Annual Meeting of the American Society of Hematology, Abstract #2826, Poster Presentation, Dec. 4, 2016, San Diego, CA.
Fogler et al., "Mobilization of Tumor-Primed, Marrow Infiltrating Lymphocytes Into Peripheral Blood with Inhibitors of E-Selectin or E-Selectin and CXCR4," Abstract #1757, Proceedings of the American Association for Cancer Research Annual Meeting, Apr. 14-18, 2018, Chicago Copy.
Fogler et al., "Abstract 1757: Mobilization of tumor-primed, marrow-infiltrating lymphocytes into peripheral blood with inhibitors of E-selectin or E-selectin and CXCR4," Cancer Research, 78 (13 Supplement) Abstract #1757, Jul. 2018.
Frenette, Paul S. et al., "Sulfated Glycans Induce Rapid Hematopoietic Progenitor Cell Mobilization: Evidence For Selectin-Dependent And Independent Mechanisms," Blood, 96:2460-2468, (2000).
Frison, N. et al., "Oligolysine-Based Oligosaccharide Clusters: Selective Recognition and Endocytosis By the Mannose Receptor and Dendritic Cell-Specific Intercellular Adhesion Molecule 3 (ICAM-3)-Grabbing Nonintegrin," The Journal of Biological Chemistry 278(26):23922-23929, Apr. 2003.
Fruehauf, S., et al., "Protection of hematopoietic stem cells from chemotherapy-induced toxicity by multidrug-resistance 1 gene transfer," Recent Results in Cancer Research, 144, Abstract Only), (1998), 1 pQ.
Fukushi et al., "Novel Fucolipids Accumulating in Human Adenocarcinoma," J. Biol. Chem. 259(16):10511-10517 (1984).
Fukushi et al., "Novel Fucolipids Accumulating in Human Adenocarcinoma. II. Selective Isolation of Hybridoma Antibodies That Differentially Recognize Mono-, Di-, and Trifucosylated Type 2 Chain," J. Biol. Chem. 259(7):4681-4685, 1984.
Gabius et al., "Endogenous Tumor Lectins: Overview and Perspectives," Anticancer Res. 6:573-578, 1986.
Gais, H.-J. et al., "Enantioselective and Enantioconvergent Syntheses of Building Blocks for the Total Synthesis of Cyclopentanoid Natural Products," Angewandte Chemie, Int. Ed. Eng. 23(2):142-143, 1984.
Gallatin et al., "A cell-surface molecule involved in organ-specific homing of lymphocyctes," Nature 304:30-34, 1983.
Garber, N. et al., "On the specificity of the D-galactose-binding lectin (PA-I) of Pseudomonas aeruginosa and its strong binding to hydrophobic derivatives of D-galactose and thiogalactose," Biochimica et Biophysica Acta, 1116:331-333 (1992).
Gebauer et al., "Selectin binding is essential for peritoneal carcinomatosis in a xenograft model of human pancreatic adenocarcinoma in pfp—/rag2—mice," Gut 2013; 62:741-750.
Gelbrich, T. et al., "Preparation of 4-benzylsulfanyl[1,2,3,5]dithiadiazol-1-ylium chlorides: potential precursors to meso-ionic 1,2,3,5-dithiadiazolium-4-thiolate," Arkivoc, (vi): 224-223 (2002).
Ghobrial, IM, "Myeloma as a model for the process of metastasis: implications for therapy," 120(1): 20-30 (2012).
Gilboa-Gardner, N. et al., "A new mitogenic D-galactosephilic lectin isolated from seeds of the coral-tree Erythrina corallodendron. Comparison with Glycine max (soybean) and Pseudomonas aeruginosa lectins," Canadian Journal of Biochemistry, 59(5):315-320 (1981).
Goodman and Gillman's, "Pharmacological Basis of Therapeutics," 10th edition, p. 54 (2001).
Gooi et al., "Stage-specific embryonic antigen involves α 1-3 fucosylated type 2 blood group chains," Nature 292:156-158, 1981.
Gout, et al., "Selectins and selectin ligands in extravasation of cancer cells and organ selectivity of metastasis," Clin. Exp. Metastasis, 25(4): 335-344 (2008).
Gravina et al., "Abstract 428: Dual E-selectin and CXCR4 inhibition reduces tumor growth and increases the sensitivity to docetaxel in experimental bone metastases of prostate cancer," Proceedings of the 106$^{th}$ Annual Meeting of the American Association for Cancer Research, Abstract #428, Apr. 18-22, 2015, Philadelphia, PA.
Gravina et al., "Abstract 428: Dual E-selectin and CXCR4 inhibition reduces tumor growth and increases the sensitivity to docetaxel in experimental bone metastases of prostate cancer," Cancer Research, 75(15 Supplemental), 428-429, Aug. 2, 2015.
Griciuc et al., "Alzheimer's Disease Risk Gene CD33 Inhibits Microglial Uptake of Amyloid Beta," Neuron, 78(4), 631-643, May 22, 2013.
Griffioen et al., "Angiostasis as a way to improve immunotherapy," Intravascular Biology Meeting 2008, 2009 SchattauerGmbH, Stuttgart, pp. 1025-1031.
Guha et al., "Cod glycopeptide with picomolar affinity to galectin-3 suppresses T-cell apoptosis and prostate cancer metastasis," Proceedings of the National Academy of Science, 110(13), 5052-5057, 2013.
Hakomori et al., "The Hapten Structure of a Developmentally Regulated Glycolipid Antigen (SSEA-1) Isolated From Human Erythrocytes and Adenocarcinoma: A Preliminary Note," Biochem. Biophys. Res. Comm. 100(4):1578-1586, 1981.
Hakomori et al., "Novel Fucolipids Accumulating in Human Adenocarcinoma. I. Glycolipids With Di-or Trifucosylated Type 2 Chain," J. Biol. Chem. 259(7):4672-4680, 1984.
Hakomori, "Aberrant Glycosylation in Cancer Cell Membranes as Focused on Glycolipids: Overview and Perspectives," Cancer Res. 45:2405-2414, 1985.
Halloran et al., "Le$^y$/H: An endothelial-selective cytokine-inducible angiogenic mediator," Journal Of Immunology, 164(9): 4868-4877 (May 1, 2000).
Hamamoto et al., "Inhibition of Dextran Sulphate Sodium (DSS)-induced Colitis in Mice by Intracolonically Administered Antibodies Against Adhesion Molecules (Endothelial Leucocyte Adhesion Molecule-1 (ELAM-1) or Intercellular Adhesion Molecule-1 (ICAM-1))", Clinical Experimental Immunology, 117, (1999), 462-468.

(56) References Cited

OTHER PUBLICATIONS

Handa et al., "Selectin GMP-140 (CD62; PADGEM) Binds to Sialosyl -Le$^a$ and Sialosyl-Le$^x$, and Sulfated Glycans Modulate this Binding," Biochemical and Biophysical Research Communication 181 (3):1223-1230, 1991.

Handschel et al., "Irradiation induces increase of adhesion molecules and accumulation of beta2-integrin-expressing cells in humans" International Journal of Radiation Oncology, Biology, Physics 45(2): 475-481 (1999).

Hansson et al., "Biosynthesis of the Cancer-associated Sialyl-Le.sup.a Antigen," Journal of Biological Chemistry 260(16):9388-9392, 1985.

Harlan, "Introduction-anti-adhesion therapy in sickle cell disease," Blood 95:365-367, 2000.

Hasegawa et al., "Synthesis of deoxy-L-fucose-containing sialyl Lewis X ganglioside analogues," Carbohydrate Research 257: 67-80, 1994.

Hasegawa et al., "Synthesis of sialyl Lewis X ganglioside analogues containing modified L-fucose residues," Carbohydrate Research 274: 165-181, 1995.

Hashida et al., "High-efficacy site-directed drug delivery system using sialyl-Lewis X conjugated liposome," Experimental Eye Research 86, 2008, 138-149.

Hayashi et al., "Increased Level of Soluble E-Selectin in the Serum from Patients with Idiopathic Pulmonary Fibrosis," Inflammation, 28(1), 1-5, 2004.

Hebbar et al., "E-selectin gene S128R polymorphism is associated with poor prognosis in patients with stage II or III colorectal cancer," European Journal of Cancer, 45, 1871-1876, 2009.

Hebbel, P.R., "Blockade of Adhesion of Sickle Cells to Endothelium by Monoclonal Antibodies," The New England Journal of Medicine 342:1910-1912, Jun. 22, 2000.

Hendrix, C.W. et al., "Pharmacokinetics and Safety of AMD-3100, a Novel Antagonist of the CXCR-4 Chemokine Receptor, in Human Volunteers," Antimicrobial Agents and Chemotherapy 44(6):1667-1673, Jun. 2000.

Hickey et al., "Leukocyte-Endothelial Cell Interactions Are enhanced in Dermal Postcapillary Venules of MRL/fas$^{lpr}$ (Luplus-Prone) Mice: Roles of P-and E-Selectin," The Journal of Immunology, 168, 4728-4736, 2002.

Hiddemann et al., "Management of Acute Myeloid Leukemia in Elderly Patients," Journal of Clinical Oncology, 17(11), 3569-3576, 1999.

Hilal et al., "Electronic structure of orotic acid I. Geometry, conformational preference and tautomerism:, Journal of Molecular Structure (Theochem)" 685 (2004) 35-42.

Hilgenbrink et al., "Folate receptor-mediated drug targeting: from therapeutics to diagnostics," J. Pharm. Sci., 94(10): 2135-2146 (2005).

Hirai et al., Accumulation of liposome with Sialyl Lewis X to inflammation and tumor region: Application to in vivo bio-imaging., Biochemical and Biophysical Research Communications, 353 (2007), 553-558.

Holgate, ST et al., "Epithelium dysfunction in asthma," Current Reviews of Allergy and Clinical Immunology, 120: 1233-1234 (2007).

Holmes et al., "Enzymatic Basis for the Accumulation of Glycolipids with X and Dimeric X Determinants in Human Lung Cancer Cells (NCI-H69)," J. Biol. Chem. 260(12):7619-7627, 1985.

Hong, P. W.-P. et al., "Identification of the Optimal DC-SIGN Binding Site on Human Immunodeficiency Virus Type 1 gp120," Journal of Virology 18(15):8325-8336, Aug. 2007.

Horacek et al., "Multi-analytical evaluation of serum levels of cytokines and adhesion molecules in patients treated for acute myeloid leukemia using biochip array technology," Biomed Pap Med Fac Univ Palacky Olomouc, Czech Repub., 157(4), 277-279, Dec. 2013.

Horiya et al., "Recent strategies targeting HIV glycans in vaccine design," Nature Chemical Biology, 10, 990-999, 2014.

Mauch, P., et al., "Hematopoietic Stem Cell Compartment: Acute and Late Effects of Radiation Therapy and Chemotherapy", Int. J. Radiation Oncology Bioi. Phys . . . 31(5), 1995), 1319-1339.

McCavit et al., "An Analysis of the Pediatric Sub-Group From the Phase 2 Study of GMI-1070—A Novel Agent For The Vaso-Occlusive Crisis of Sickle Cell Anemia", Blood, 122(21):2206, Nov. 15, 2013.

McCavit et al., "An Analysis of the Pediatric Sub-Group From the Phase 2 Study of GMI-1070—A Novel Agent For The Vaso-Occlusive Crisis of Sickle Cell Anemia", ASH Annual Meeting 2013, Poster#56448, Dec. 8, 2013.

McEver et al., "Leukocyte trafficking mediated by selectin-carbohydrate interactions," J. Biol. Chem., 270 (19): 11025-11028 (1995).

McKenzie et al., "Low rhodamine 123 retention identifies long-term human hematopoietic stem cells with the Lin-CD34+CD38- population", Blood. 109, (2007), 543- 545.

McLean et al., "Effects of a small molecule inhibitor of ICAM-1 and E-selectin expression on colonic inflammatory hyperalgesia and colitis" Digestive Disease 2003, Orlando FL, May 2003, abstract.

Menendez et al., "A Peptide Inhibitor of HIV-1 Neutralizing Antibody 2G12 is not a Structural Mimic of the Natural Carbohydrate Epitope on gp120," The FASEB Journal 22:1380-1382, May 2008.

Metza et al., "Venous Thrombosis and Post-Thrombotic Syndrome: From Novel Biomarkers to Biology," Methodist Debakey Cardiovasc J, 14(3), 2018, pp. 173-181.

Mimeault, et al., "Stem cells: a revolution in therapeutics-recent advances in stem cell biology and their therapeutic applications in regenerative medicine and cancer therapies," Clin. Pharmacol. Therapeutics, 82(3): 252-264 (2007).

Mitsiades, et al., "Preclinical studies in support of defibrotide for the treatment of multiple myeloma and other neoplasias," Clin. Cancer Res., 15 (4): 1210-1221 (2009).

Moore et al., "Evolution of an HIV Glycan-Dependent Broadly Neutralizing Antibody Epitope Through Immune Escape," Nature Medicine doi:10.1038/nm.2985 pp. 1-6, Oct. 2012.

Moore, "Waking Up HSCs: A new Role For E-Selectin," Nat. Med., 18:16131614, (2012).

Morikis et al., "Selectin catch-bonds mechanostransduce integrin activation and neutrophil arrest on inflamed endothelium under shear flow," Blood, Nov. 9, 2017, vol. 130, No. 19. pp. 2101-2110.

Mosley et al., "Recent Patents Regarding the Discovery of Small Molecule CXCR4 Antagonists," Expert Opin. Ther. Patents 19(1):23-38, 2009.

Mulligan et al., "Selection for animal cells that express the *Escherichia coli* gene coding for xanthine-gunine phosphoribosyltransferase," Proc. Natl. Acad. Sci. USA 78:2072-2076, 1981.

Mulligan et al., "Role of Endothelial-Leukocyte Adhesion Molecule 1 (ELAM-1) in Neutrophil-mediated Lung Injury in Rats," J Clin Invest.,88(4):1396-406, Oct. 1991.

Murohara et al., "Cardioprotection by liposome-conjugated sialyl Lewis$^x$-oligosaccharide in myocardial ischaemia and reperfusion injury," Cardiovascular Research, 30(1995), 965-974.

Muz et al., "Inhibition of E-Selectin or E-Selectin Together with CXCR4 Re-Sensitizes Multiple Myeloma to Treatment," Proceedings of the 108$^{th}$ Annual Meeting of the American Association for Cancer Research, Abstract #5005, Oral Presentation, Apr. 1-5, 2017, Washington DC.

Muz et al., "Abstract 5005: Inhibition of E-selectin or E-selectin together with CXCR4 resensitizes multiple myeloma to treatment," Cancer Research, 77(13 Supplement), Abstract #5005, Jul. 2, 2017.

Myers et al., "Pan-Selectin Antagonist, GMI-1070 Decreases Venous Thrombosis in a Mouse Model", Blood, 118, Abstract #3273, Nov. 2011.

Myers Jr. et al., "Novel E-Selectin Antagonist GMI-1271 Decreases Venous Thrombosis without Increased Bleeding Potential in a Mouse Model," Blood, 120(21), Abstract #3422, Nov. 16, 2012.

Myers Jr. et al., "Novel E-Selectin Antagonist GMI-1271 Decreases Venous Thrombosis without Increased Bleeding Potential in a Mouse Model," Proceedings of the 54$^{th}$ Annual Meeting of the American Society of Hematology, Abstract #3422 Poster Presentation on Dec. 10, 2012, Atlanta, GA.

(56) References Cited

OTHER PUBLICATIONS

Myers et al., "E-Selectin Inhibitor GMI-1271 Works in Combination with Low-Molecular Weight Heparin to Decrease Venous Thrombosis and Bleeding Risk in a Mouse Model", Blood, 124(21):593, Dec. 6, 2014.
Myers Jr. et al., "E-Selectin Inhibitor GMI-1271 Works in Combination with Low-Molecular Weight Heparin to Decrease Venous Thrombosis and Bleeding Risk in a Mouse Model," Proceedings of the 56th Annual Meeting of the American Society of Hematology, Abstract #593 Oral Presentation on Dec. 8, 2014, San Francisco, CA.
Nagel, R. L., "A Knockout of a Transgenic Mouse-Animal Models of Sickle Cell Anemia," The New England Journal of Medicine 339:194-195, Jul. 16, 1998.
Narita, T. et al., "Corticosteroids and medroxyprogesterone acetate inhibit the induction of breast cancer cells," Anticancer Research, 15(6B): 2523-2527 (1995)—Abstract.
Narumi, Tetsuo et al., "Synthesis And Biological Evaluation Of Selective CXCR4 Antagonists Containing Alkene Dipeptide Isosteres," Organic & Biomolecular Chemistry, 8(3): 616-621(Feb. 7, 2010).
Natarajan, M.M. et al., "Adhesion of sickle red blood cells and damage to interleukinIbeta stimulated endothelial cells under flow in vitro," Blood 87:4845-4852, 1996.
Natoni et al., "Multiple Myeloma Cells Express Functional E-Selectin Ligands Which Can be Inhibited Both in-Vitro and in-Vivo Leading to Prolongation of Survival in a Murine Transplant Model", Blood, 124(21):4718, Dec. 6, 2014.
Natoni et al., Multiple Myeloma Cells Express Functional E-Selectin Ligands Which Can be Inhibited Both in vitro and in vivo Leading to Prolongation of Survival in a Murine Transplant Model, Proceedings of the 56th Annual Meeting of the American Society of Hematology, Abstract #4718 Poster Presentation on Dec. 8, 2014 in San Francisco, CA.
Natoni et al., "E-Selectin Ligand Expression Increases with Progression of Myeloma and Induces Drug Resistance in a Murine Transplant Model, Which Is Overcome By the Glycomimetic E-Selectin Antagonist, GMI-1271," Blood, 126(23), Abstract#1805, Dec. 3, 2015.
Natoni et al., "E-Selectin Ligand Expression Increases with Progression of Myeloma and Induces Drug Resistance in a Murine Transplant Model, Which Is Overcome By the Glycomimetic E-Selectin Antagonist, GMI-1271," Proceedings of the 57th Annual Meeting of the American Society of Hematology, Abstract #1805 Poster Presentation on Dec. 5, 2015 in Orlando, FL.
Natoni et al., "E-selectin ligands recognized by HECA452 induce drug resistance in myeloma, which is overcome by the E-selectin antagonist, GMI-1271," Leukemia (2017) 31, 2642-2651.
Newlaczyl et al., "Galectin-3—A jack-of-all-trades in cancer," Cancer Letters, 313, 123-128, 2011.
Nguyen, M et al., "Novel synthetic analogs 1-29 of sialyl Lewis X can inhibit angiogenesis in vitro and in vivo," Biochemical And Biophysical Research Communications, 228(3): 716-723 (Nov. 21, 1996).
Nicolaou et al., "Total Synthesis of the Tumor-Associated Lex Family of Glycosphingolipids," J. Amer. Cherm. Soc. 112:3693-3695, 1990.
Noguchi, M. et al. "A minor E-selectin ligand, CD65, is critical for extravascular infiltration of acute myeloid leukemia cells," Leukemia Research, 25: 847-853 (2001).
Nonomura et al., "CD43, but not P-Selectin Glycoprotein Ligand-1, Functions as an E-Selectin Counter-Receptor in Human Pre-B-Cell Leukemia NALL-1," Cancer Res, 2018, 68⊙ 3), Feb. 1, 2008, pp. 790-800.
Noonan et al., "Adoptive transfer of activated marrow-infiltrating lymphocytes induces measurable antitumor immunity in the bone marrow in multiple myeloma," Science Translational Medicine, vol. 7, No. 288, May 20, 2015.
Norman et al., "Sialyl Lewis[y](sLe[y]) and an sLe[x] Mimetic, CGP69669A, Disrupt E-Selectin-Dependent Leukocyte Rolling In Vivo," Blood, 91(2):475-483 (Jan. 15, 1998).

Nudelman et al., "Novel Fucolipids of Human Adenocarcinoma: Disialosyl Lea Antigen (III.sup.4FucIII.sup.6NeuAcIV.sup.3NeuAcLc.sub.4) of Human Colonic Adenocarcinoma and the Monoclonal Antibody (FH7) Defining This Structure," J. Biol. Chem. 261:5487-5495, 1986.
Nutku, E. et al., "Ligation of Siglec-8: a selective mechanism for induction of human eosinophil apoptosis," Blood, 101(12): 5014-5020 (2003).
Oancea et al., "Alleviation of Acute Drug-Induced Liver Injury Following Acetaminophen Overdose by Therapeutic Blockade of E-Selectin in Preclinical Mouse Model," Gastroenterology, 150(4), Supplement 1, p. S1029, Abstract #358 (no oral presentation available), New Orleans, LA, Apr. 2016.
Obermajer, N. et al., "Design, synthesis and activity evaluation of mannose-based DC-SIGN antagonists," Molecular Diversity 15:347-360, May 2011.
Orhlein, R., "Carbohydrates and Derivatives as Potential Drug Candidates with Emphasis on the Selectin and Linear-B Area," Mini Reviews in Medicinal Chemistry 1: 349-361, 2001.
Oxford Textbook of Oncology, vol. 1, published 1995 by Oxford University Press, pp. 447-453.
Palcic et al., "A Bisubstrate Analog Inhibitor for .alpha.(1.fwdarw.2)-Fucosyltransferase," J. Biol. Chem. 264:17174-17181, 1989.
Palcic et al., "Enzymic Synthesis of Oligosaccharides Terminating in the Tumor-Associated Sialyl-Lewis-a Determinant," Carbohydr. Res. 190:1-11, 1989.
Palcic et al., "Regulation of N-Acetylglucosaminyltransferase V Activity. Kinetic Comparisons of Parental, Rous Sarcoma Virus-Transformed BHK, and .sub.L-Phytohemagglutinin-Resistant BHK Cells Using Synthetic Substrates and an Inhibitory Substrate Analog," J. Biol. Chem. 265:6759-6769, 1990.
Palma-Vargas, J.M. et al., "Small-Molecule Selectin Inhibitor Protects Against Liver Inflammatory Response After Ischemia and Reperfusion," J. Am. Coll. Surg. 185: 365-372, 1997.
Pamphilon et al., "Stem Cell Donation—What advice can be given to the donor?," Br. J. Haematol. 147(1):71-76, Oct. 2009, Author manuscript available at NIH Public access Aug. 1, 2012.
Paneghetti et al., "A novel endothelial-derived anti-inflammatory activity significantly inhibits spontaneous choroidal neovascularization in a mouse model," Vascular Cell, (2016, 8:2, pp. 1-12.
Pattillo et al., "Radiation-Guided Targeting of Combretastatin Encapsulated Immunoliposomes to Mammary Tumors," Pharmaceutical Research, vol. 26, No. 5, May 2009, pp. 1093-1100.
Patton, J. T. et al., "GMI-1070: a Small Glycomimetic, Pan-selectin Antagonist that Improves Blood Flow and Inhibits Blood Cell Adhesion in Sickle Mice," Abstract ID:ABSTY-5APYL-CA6TP-V2ET6, Sep. 2, 2005.
Payre, et al., "Chemoenzymatische Synthese eines zweifach modifizierten Pentasaccharids als Substrat fur einen alpha-Amylase-Assay durch Fluoreszenz-loschung" Angew. Chem., vol. 107, No. 11, 1995, pp. 1361-1364.
Payre, N. et al., "Chemoenzymatic Synthesis of a Modified Pentasaccharide as a Specific Substrate for a Sensitive Assay of a-Amylase by Fluorescence Quenching," Angew. Chem. Int. Ed. Engl. 34(11): 1239-1241 (1995).
Peacock et al., "Emergency Department Use of Galectin-3, "Critical Pathways in Cardiology, 13(2), 73-77, 2014.
Pejchal R. et al., "A Potent and Broad Neutralizing Antibody Recognizes and Penetrates the HIV Glycan Shield," Science 334:1097-1103, Nov. 2011.
Pelus, "Peripheral blood stem cell mobilization: new regimens, new cells, where do we stand," Curr. Opin. Hematol., 15(4): 285-292 (2008).
Pentelute, Brad et al., "A Semisynthesis Platform for Investigating Structure-Function Relationships in the N-Terminal Domain of the Anthrax Lethal Factor," ACS Chemical Biology. 5(4): 359-364 (Apr. 2010).
Pentelute, Brad L. et al., "Chemica 1 1-16 dissection of protein translocation through the anthrax toxin pore," Angewandte Chemie, 50(10): 2294-2296 (Mar. 1, 2011).
Perret, S. et al., "Structural basis for the interaction between human milk oligosaccharides and the bacterial lectin PA-IIL of Pseudomonas aeruginosa," Biochem. J. 389: 325-332, 2005. cited by other.

(56) References Cited

OTHER PUBLICATIONS

Peterson et al., "A Novel and Potent Inhibitor of E-Selectin, GMI-1687, Attenuates Thrombus Formation and Augments Chemotherapeutic Intervention of AML in Preclinical Models Following subcutaneous Administration," Poster #4678, Proceedings of the 60th American Society of Hematology Annual Meeting, Dec. 3, 2018, San Diego, CA.
Pezeshkian et al., "Leukemia Mediated Endothelial Cell Activation Modulates Leukemia Cell Susceptibility to Chemotherapy through a Positive Feedback Loop Mechanism," PLOS One, 8(4), e60823, 2013.
Phillips et al., "ELAM-1 Mediates Cell Adhesion by Recognition of a Carbohydrate Ligand, Sialyl-Le.sup.x," Science 250:1130-1132, 1990.
Picker er al., "The Neutrophil Selectin LECAM-1 Presents Carbohydrate Ligands to the Vascular Selectins ELAM-1 and GMP-140," Cell 66:921-933, 1991.
Plasterk, R. H. A., et al., "The silence of the genes", Current Opinion in Genetics and Development 10 (2000), 562-567.
Porquet et al., "Survival advantages conferred to colon cancer cells by E-selectin-induced activation of the PI3K-NF$_k$B survival axis downstream of Death receptor-3," BMC Cancer, 2011, 11:285, pp. 1-12.
Prescher et al., "Discovery of multifold modified sialosides as human CD22/Siglec-2 ligands with nanomolar activity on B-cells," ACS Chem Biol., Jul. 18, 2014, 9(7):1444-50.
Prescher et al., "New Human CD22/Siglec-2 Ligands with a Triazole Glycoside," ChemBioChem, 2017, 18, 126-1225.
Price et al., "Breast Cancer Cells Metastasize to Bone through E-Selectin Positive Vascular Gateways", AACR Annual Meeting 2014, Poster #4831, Apr. 9, 2014.
Price et al., "Breast Cancer Cells Metastasize to Bone through E-Selectin Positive Vascular Gateways," Proceedings of the 105th Annual Meeting of the AACR, 4831, Apr. 5-9, 2014, San Diego, CA.
Price et al., "Breast cancer cells metastasize to bone through E-selectin + vascular gateways," Cancer Research, 74(19 Supplement), 4831, Sep. 20, 2014.
Price et al., "Metastatic Breast Cancer Cell Communication Within a Pro-Dormancy Bone Marrow Niche," Proceedings of the 106th Annual Meeting of the American Association for Cancer Research, Abstract #3212, Apr. 18-22, 2015, Philadelphia, PA.
Price et al., "Metastatic breast cancer cell communication within a pro-dormancy bone marrow niche," Cancer Research, 75(15 Supplement), Abstract #3212, Aug. 2015.
Price et al., "Dormant breast cancer micrometastases reside in specific bone marrow niches that regulate their transit to and from bone," Science Translational Medicine, May 25, 2016, vol. 8, Issue 340.
Prokazova et al., "Sialylated lactosylceramides. Possible inducers of non-specific immunosuppression and atherosclerotic lesions," European Journal of Biochemistry 172:1-6, 1988.
Purton et al., "Limiting Factors in Murine Hematopoietic Stem Cell Assays," Cell Stem Cell 1: 263-270, Sep. 2007.
Rapoport et al., "Ganglioside Binding Pattern of CD33-Related Siglecs," Bioorganic and Medicinal Chemistry Letters, 13(4), 675-678, Feb. 2003.
Rapoport, E. et al., "Probing Sialic Acid Binding Ig-Like Lectins (Siglecs) with Sulfated Oligosaccharides," Biochemistry (Moscow), 71(5): 496-504 (2006).
Rauvala et al., "Studies on Cell Adhesion and Recognition. I. Extent and Specificity of Cell Adhesion Triggered by Carbohydrate-reactive Proteins (Glycosidases and Lectins) and by Fibronectin," J. Cell Biol. 88:127-137, 1981.
Ravandi et al., "Characteristics and outcome of patients with acute myeloid leukemia refractory to 1 cycle of high-dose cytarabine-based induction chemotherapy," Blood 116(26), 5818-5823, 2010.
Reina et al., "1,2-Mannobioside Mimic: Synthesis, DC-SIGN Interaction by NMR and Docking, and Antiviral Activity," ChemMedChem 2:1030-1036, 2007.

Rice et al., "An Inducible Endothelial Cell Surface Glycoprotein Mediates Melanoma Adhesion," Science 246:1303-1306, 1989.
Richert et al., "Inhibition of CXCR4 by CTCE-9908 Inhibits Breast Cancer Metastasis to Lung and Bone," Oncology Reports 21:761-767, 2009.
Roberge, J. Y., et al., "A Strategy for a Convergent Synthesis of N-Linked Glycopeptides on a Solid Support", Science 269(5221), (1995), 202-204.
Röllig et al., "Long-Term Prognosis of Acute Myeloid Leukemia According to the New Genetic Risk Classification of the European LeukemiaNet Recommendations: Evaluation of the Proposed Reporting System," Journal of Clinical Oncology, 29(20), 2758-2765, 2011.
Rood et al., "E-Selectin And Very Late Activation Antigen-r Mediate Adhesion Of Hematopoietic Progenitor Cells To Bone Marrow Endothelium," Ann Hematol, 79:477-484, (2000).
Ruoslahti et al., "New Perspectives in Cell Adhesion: RGD and Integrins," Science 238:491-497, 1987.
Sackstein, "The Biology of CD44 and HCELL in Hematopoiesis: The 'Step 2-Bypass Pathway' and Other Emerging Perspectives", Current Opinion in Hematology, 18(4):239-248 (2011).
Sakurai et al., "Selection of a Monoclonal Antibody Reactive with a High-Molecular-Weight Glycoprotein Circulating in the Body Fluid of Gastrointestinal Cancer Patients," Cancer Research 48:4053-4058, 1988.
Salameh et al., "1H-1,2,3-Triazol-1-yl thiodigalactoside derivatives as high affinity galectin-3 inhibitors," Bioorganic & Medicinal Chemistry, 18, 5367-5378, 2010.
Sanz et al., "Roflumilast inhibits leukocyte-endothelial cell interactions, expression of adhesion molecules and microvascular permeability", British Journal of Pharmacology. 152(4), (2007), 481-492.
Sastry et al., "Cloning of the immunological repertoire in *Escherichia coli* for generation of monoclonal catalytic antibodies: Construction of a heavy chain variable region-specific cDNA library," Proc. Natl. Acad. Sci. USA 86:5728-5732, 1989.
Scanlan et al., "The Broadly Neutralizing Anti-Human Immunodeficiency Virus Type 1 Antibody 2G12 Recognizes a Cluster of a1-2 mannose Residues on the Outer Face of gp120," Journal of Virology 76:7306-7321, Jul. 2002.
Scanlan et al., "Exploiting the Defensive Sugars of HIV-1 for Drug and Vaccine Design," Nature 446:1038-1045, Apr. 2007.
Scharfman et al., "Pseudomonas aeruginosa binds to neoglycoconjugates bearing mucin carbohydrate determinants and predominantly to sialyl-Lewis x conjugates," Glycobiology 9(8): 757-764, 1999.
Scharfman et al., "Recognition of Lewis x Derivatives Present on Mucins by Flagellar Components of Pseudomonas aeruginosa," Infection and Immunity 69(9): 5243-5248, Sep. 2001.
Schief et al., "Challenges for Structure-Based HIV Vaccine Design," Current Opinion in HIV and AIDS 4:431-440, 2009.
Schwizer et al. "Pre-organization of the Core Structure of E-Selectin Antagonist," Chemistry—A European Journal, 18(5): 1342-1351 (Jan. 2012).
Shamay et al., "E-selectin binding peptide-polymer-drug conjugates and their selective cytotoxicity against vascular endothelial cells," Biomaterials, 30, 6460-6468, 2009.
Smith et al., "Glycomimetic Antagonist of E-selectin, GMI-1271, Enhances Therapeutic Activity of the Hypomethylating Agent, 5-Azacitidine, in the KG1 Model of AML," Abstract #2867, Proceedings of the American Association for Cancer Research Annual Meeting, April 14-18, 2018, Chicago, IL.
Steele et al., "425 A Small Molecule Glycomimetic Antagonist of E-selectin and CXCR4 (GMI-1359) Prevents Pancreatic Tumor Metastasis and Offers Improved Chemotherapy," Proceedings of the 106th Annual Meeting of the American Association for Cancer Research, Abstract #425, Apr. 18-22, 2015, Philadelphia, PA.
Winkler et al., "Administration of E-selectin Antagonist GMI-1271 Improves Survival to High-Dose Chemotherapy by Alleviating Mucositis and Accelerating Neutrophil Recovery", ASH Annual Meeting, Poster#63045, Dec. 8, 2013.

(56) References Cited

OTHER PUBLICATIONS

Abraham, W.M. et al., "Selectin Blockade Prevents Antigen-induced Late Bronchial Response and Airway Hyperresponsiveness in Allergic Sheep," Am J. Respir Crit Care Med. 159: 1205-1214, 1999.
Acord, J. et al., "A rapid microplate method for quantifying inhibition of bacterial adhesion to eukaryotic cells," Journal of Microbiological Methods 60: 55-62, 2005.
Adams, E. W. et al., "Oligosaccharide and Glycoprotein Microarrays as Tools in HIV Glycobiology: Glycan-Dependent gp120/Protein Interactions," Chemistry & Biology 11:875-881, Jun. 2004.
Aggoune et al., "The Vascular Niche Is Involved in Regulating Leukemic Stem Cells in Murine Chronic Myelogenous Leukemia" Blood, 124(21):516, Dec. 6, 2014.
AGGOUNE et al., "The vascular niche is involved in regulating leukemic stem cells in murine chronic myelogenous leukemia," Proceedings of the 56$^{th}$ Annual Meeting of the American Society of Hematology, Abstract #516 Oral Presentation, Dec. 8, 2014, San Francisco, CA.
Alessandro, et al., "Role of S128R polymorphism of E-selectin in colon metastasis formation," Int. J. Cancer, 121(3): 528-535 (2007).
Alessandro et al., "Multiple Myeloma Cells Express Functional E-Selectin Ligands Which Can be Inhibited Both in vitro and in vivo Leading to Prolongation of Survival in a Murine Transplant Model," Blood, Dec. 6, 2014, XP055349837, 56$^{th}$ Annual Meeting of the American Society of Hematology, Dec. 6-9, 2014, San Francisco, CA.
Ali, M., et al., "Polymers bearing sLex-mimetics are superior inhibitors of E-selectin-dependent leukocyte rolling in vivo", The FASEB Journal 18(1), (2004), 152-154.
Alousi, A., et al., "Reduced-Intensity Conditioning Allogeneic Hematopoietic Stem Cell Transplantation", Clinical Advances in Hematoloav & Oncoloav. 5(7), (2007), 560-570.
Angelini et al., "E-Selectin Antagonist GMI-1271 Shows a Favorable Safety, PK and Bleeding Profile in Phase I Studies of Healthy Volunteers," Blood, 128(22), Abstract #3826, Dec. 6, 2014.
Angelini et al., Proceedings of the 56$^{th}$ Annual Meeting of the American Society of Hematology, Abstract #3826, Poster Presentation, Dec. 8, 2014, in San Francisco, CA.
Antoine et al., "Expression of E-selectin ligand-1 (CFR/ESL-1) on heptatic stellate cells: Implications for leukocyte extravasation and liver metastasis," Oncology Reports, 21:357-362, 2009.
Aoki et al., "Effects of Vascular Endothelial Growth Factor and E-Selectin on Angiogenesis in the Murine Metastatic RCT Sarcoma," Tumor Biol., 2001; 22:239-246.
Arakaki, R. et al., "T134, a Small-Molecule CXCR4 Inhibitor, Has No Cross-Drug Resistance with AMD3100, a CXCR4 Antagonist with a Different Structure," Journal of Virology 73(2):1719-1723, Feb. 1999.
Aref et al., "L and E Selectins in Acute Myeloid Leukemia: Expression, Clinical Relevance and Relation to Patient Outcome," Hematology, 7(2), 83-87, 2002.
Arshad, S. et al., "Primary prevention of asthma and atopy during childhood by allergen avoidance in infacny: a randomised controlled study," Thorax., 58:489-493 (2003).
Arshad, S. et al., "Primary prevention of asthma and allergy," J. Allergy Clin. Immunol., 116: 3-14 (2005).
Astronomo, R.D. et al., "A Glycoconjugate Antigen Based on the Recognition Motif of a Broadly Neutralizing Human Immunodeficiency Virus Antibody, 2G12, Is Immunogenic but Elicits Antibodies Unable To Bind to the Self Glycans of gp120," Journal of Virology 82(13):6359-6368, Jul. 2008.
Azab et al., "Role of Selectins in the Pathogenesis of Multiple Myeloma", J Clin Oncol, 27(15s):Absrt 11103, 2009.
Azab et al., "Role of Selectins in the Pathogenesis of Multiple Myeloma", ASCO Annual Meeting 2009, Poster #11103, May 2009.
Azab et al., "P-selectin Glycoprotein Ligand Regulates the Interaction of Multiple Myeloma Cells with the Bone Marrow Microenvironment", Blood, 119(6), 1468-1478, Nov. 16, 2011.

Baeckstrom et al., "Purification and Characterization of a Membrane-bound and a Secreted Mucin-type Glycoprotein Carrying the Carcinoma-associated Sialyl-Le.sup.a Epitope on Distinct Core Proteins," J. Biol. Chem. 266(32):21537-21547, 1991.
Banteli, R. et al., "Potent E-Selectin Antagonists," Helvetica Chimica Acta 83(11): 2893-2907, 2000.
Banteli et al., "Synthesis of sialyl lewisx mimics. Modifications of the 6-position of galactose," Bioorganic & Medicinal Chemistry Letters, 11(4): 459-462 (2001).
Barasch et al., "Palifermin for Management of Treatment-Induced Oral Mucositis in Cancer Patients", Biologies: Targets & Therapy, 3:111-116, 2009.
Barnes, P. et al., "How do corticosteroids work in asthma?" Ann. Intern. Med., 139: 359-370 (2003).
Barthel et al., "Targeting selectins and selectin ligands in inflammation and cancer," Expert Opinion Therapeutic Targets, 11(11), 1473-1491, 2007.
Bastin, R.. et al.," Salt Selection and Optimisation Procedures for Pharmaceutical New Chemical Entities" Organic Process Research & Development (2000), vol. 4, pp. 427-435.
Bedard et al., "Expert Opinion: Selectin Inhibitors: A Patent Review," Rights Link, 20(6):781-793, 2010.
Belcher, J.D. et al., "Activated monocytes in sickle cell disease: potential role in the activation of vascular endothelium and vaso-occlusion," Blood 96(7):2451-2459, Oct. 1, 2000.
Belcher, J.D. et al., "Inflammatory response in transgenic mouse models of human sickle cell anemia," Blood 96(11)Pt. 1 :600a, Abstract #2574, Nov. 16, 2000.
Bennett, C. F., et al., "Inhibition of Endothelial Cell Adhesion Molecule Expression with Antisense Oligonucleotides", Journal of Immunoloav. 152(7), (1994), 3530-3540.
Berg et al., "A Carbohydrate Domain Common to Both Sialyl Le.sup.a and Sialyl Le.sup.x Is Recognized by the Endothelial Cell Leukocyte Adhesion Molecule ELAM-1," J. Biol. Chem. 266(23):14869-14872, 1991.
Berg et al., "The Cutaneous Lymphocyte Antigen Is a Skin Lymphocyte Homing Receptor for the Vascular Lectin Endothelial Cell-Leukocyte Adhesion Molecule 1," J. Exp. Med. 174:1461-1466, 1991.
Berger et al., "Adoptive transfer of effector CD8+ T cells derived from central memory cells establishes persistent T cell memory in primates."J. Clin. Invest. 118(1):294-305 (2008).
Bevilacqua, et al., "Endothelial-leukocyte adhesion molecules in human disease," Ann. Rev. Med., 45: 361-378 (1994).
Bhaskar, V. et al. "E-selectin Up-regulation Allows for Targeted Drug Delivery in Prostrate Cancer," Cancer Research, 63: 6387-6394 (Oct. 2003).
Bird et al., "Oligosaccharides Containing Fucose Linked .alpha.(1-3) and .alpha.(1-4) to N-Acetylglucosamine Cause Decompaction of Mouse Morulae," Devel. Biol. 104:449-460, 1984.
Bjercke,"Rational Design and Synthesis of Oligosaccharide Mimetics: Selectin Antagonists as Cell Adhesion Inhibitors," Abstracts of Papers, 210th ACS National Meeting, American Chemical Society, Chicago, IL, Aug. 20-24, 1995, MEDI-18.
Blanc-Muesser et al., "Syntheses Stereoselective de 1-Thioglycosides," Carbohydrate Research 67:305-328, 1978, and English Translation.
Bleckmann et al., "O-glycosylation pattern of CD24 from mouse brain," Biol. Chem., vol. 390, pp. 627-645, Jul. 2009.
Bochner, B. et al., "Glycan array screening reveals a candidate ligand for Siglec-8," Journal of Biological Chemistry, 280(6): 4307-4312 (2005).
Bock, K. et al., "Conformations in Solution of α,α-Trehalose, α-D-Glucopyranosyl α-D-Mannopyranoside, and Their 1-Thioglycosyl Analogs, and a Tentative Correlation of Their Behaviour with Respect to the Enzyme Trehalase," European Journal of Biochemistry, 131:595-600, 1983.
Bogden, A. E., et al., "Amelioration of Chemotherapy-Induced Toxicity by Cotreatment with AcSDKP, a Tetrapeptide Inhibitor of Hematopoietic Stem Cell Proliferation", Annals New York Academv of Sciences. 628, (1991), 126-139.

(56) References Cited

OTHER PUBLICATIONS

Borentain et al., "Inhibition of E-selectin expression on the surface of endothelial cells inhibits hepatocellular carcinoma growth by preventing tumor angiogenesis," Cancer Chemother Pharmacol (2016), 77:847-856.

Borsig et al., "Synergistic effects of L-and P-selectin in facilitating tumor metastasis can involve non-mucin ligands and implicate leukocytes ad enhancers of metastasis," Proceedings of the National Academy of Sciences, 99(4), 2193-2198, 2002.

Bowen et al., "Characterization of a Human Homologue of the Murine Peripheral Lymph Node Homing Receptor," Journal of Cell Biology, 109:421-427, 1989.

Bradford, G. B., et al., "Quiescence, cycling, and turnover in the primitive hematopoietic stem cell compartment", Experimental Hematoloav. 25, (1997), 445-453.

Brandley et al., "Carbohydrate Ligands of LEC Cell Adhesion Molecules," Cell, 63:861-863, 1990.

Breems et al., "Prognostic Index for Adult Patients With Acute Myeloid Leukemia in First Relapse," Journal of Clinical Oncology, 23(9(), 1969-1978, 2005.

Bridger, GJ et al. "Synthesis and Structure—Activity Relationships of Phenylenebis(methylene)-Linked Bis-Tetraazamacrocycles That Inhibit HIV Replication. Effects of Macrocyclic Ring Size and Substituents on the Aromatic Linker," J. Med. Chem., 38: 366-378 (1995).

Brodt et al., "Liver endothelial E-selectin mediates carcinoma cell adhesion and promotes liver metastasis," Int. J. Cancer, 71(4): 612-619 (1997).

Broquet et al., "Effect of Desipramine on a Glycoprotein Sialyltransferase Activity in C6 Cultured Glioma Cells," J. Neurochem., 54:388-394, 1990.

Burkhardt, K., et al., "The Significance of Adhesion Molecules in Nephrology", Artificial Oraans 20(5), (1996), 433-436.

Calarese, D. A. et al., "Antibody Domain Exchange is and Immunological Solution to Carbohydrate Cluster Recognition," Science 300:2065-2071, Jun. 2003.

Calarese, D. A et al., "Dissection of the Carbohydrate Specificity of the Broadly Neutralizing Anti-HIV-1 Antibody 2G12," Proceedings of the National Academy of Sciences 102(38):13372-13377, Sep. 2005.

Cao, X. et al., "Defective Lymphoid Development in Mice Lacking Expression of the Common Cytokine Receptor Y Chain," Immunity, 2:223-238, Mar. 1995.

Ceder, O. et al., "On the Absolute Configuration of 3-Cyclohexene-1-carboxylic Acid," Acta Chemica Scandivavica, 24(8):2693-2698, 1970.

Chang et al., "Effects of Pan-Selectin Antagonist GMI-1070 on the Treatment of Vaso-Occlusion in Sickle Cell Mice", Blood, 112(11), Abstract #535, Nov. 2008.

Chang, J. et al. "GMI-1070, a novel pan-selectin antagonist, reverses acute vascular occlusions in sickle cell mice," Blood, 116(10): 1779-1786 (Sep. 2010).

Chantarasrivong et al., "Synthesis and Functional Characterization of Novel Sialyl LewisX Mimic-Decorated Liposomes for E-selectin-Mediated Targeting to Inflamed Endothelial Cells," Mol. Pharmaceutics, 2017, 14, 1528-1537.

Chase et al., "E-Selectin Ligands as Mechanosensitive Receptors on Neutrophils in Health and Disease", Annals of Biomedical Engineering, 40(4), pp. 849-899, Apr. 2012.

Chien et al., "579 Novel Dual E-Selectin-CXCR4 Inhibitors Mobilize Human Acute Myeloid Leukemia (AML) Cells in the NODscid IL2Rγc−/− Xenograft and Confer Susceptibility to Cytarabine," Blood, 118(21) Abstract #579, Oral, Nov. 18, 2011.

Chien et al., "A Novel Small Molecule E-Selectin Inhibitor GMI-1271 Blocks Adhesion of AML Blasts to E-Selectin and Mobilizes Blood Cells in Nodscid IL2Rgc−/− Mice Engrafted with Human AML," Proceedings of the 54th Annual Meeting of the American Society of Hematology, Abstract #4092, Poster Presentation, Dec. 10, 2012, San Diego, CA.

Chien et al., "A Novel Small Molecule E-Selectin Inhibitor GMI-1271 Blocks Adhesion of AML Blasts to E-Selectin and Mobilizes Blood Cells in Nodscid IL2Rgc−/− Mice Engrafted with Human AML", 2012 ASH Annual Meeting, Poster#54715, Dec. 10, 2012.

Chien et al., "Adhesion of Acute Myeloid Leukemia Blasts to E-Selectin in the Vascular Niche Enhances Their Survival By Mechanisms Such as Wnt Activation", Blood, 122(21):61, Nov. 15, 2013.

Chien et al., "E-Selectin Ligand Expression By Leukemic Blasts Is Associated with Prognosis in Patients with AML," Blood 2018. 132:1513.

Childs et al. ,"High-molecular-weight glycoproteins are the major carriers of the carbohydrate differentiation antigens I, I and SSEA-1 of mouse teratocarcinoma cells," Biochem. J., 215:491-503 (1983).

Choi, S. et al., "Synthetic Multivalent Molecules: Concepts and Biomedical Applications," Wiley-Interscience, p. xxi-xxvi, 1-17, 2004.

Christianson, S.W. et al.,"Enhanced Human CD4+ T Cell Engraftment in $\beta_2$-Microglobulin-Deficient NOD-scid Mice," The Journal of Immunology, 158:3578-3586 (1997).

Cleophax, J. et al., "A chiral synthesis of D-(+)-2,6-dideoxystreptamine and its microbial incorporation into novel antibodies," Journal of the American Chemical Society, 98 (22): 7110-7112 (Oct. 27, 1976).

Clinical Trials.gov, "Randomized Ph I/II Study to Assess Safety, Tolerability, and Efficacy of GMI-1271 in Patients With Calf-Level Deep Venous Thrombosis (DVT)," Protocol Summary of GMI-1271-220 Clinical Trial, Apr. 7, 2016.

Clinical Trials.gov, "A Phase I Open-Label Dose Escalation Study to Determine the Efficacy, Safety and Pharmacokinetics of GMI-1271 as Adjunct to Standard of Care Chemotherapy for the Treatment of Multiple Myeloma," Protocol Summary of GMI-1271-230 Clinical Trial, Jun. 2016.

Clinical Trials.gov, "Study to Determine Safety, Pharmacokinetics and Efficacy of GMI-1271 in Combination with Chemotherapy in AML," Protocol Summary of GMI-1271-201 Clinical Trial, Nov. 7, 2016.

Collier, et al., "Membrane translocation by anthrax toxin," Molecular Aspects Of Medicine, 30(6): 413-422 (Dec. 1, 2009).

Corral et al., "Requirements for Sialic Acid on Neutrophils in a GMP-140 (PADGEM) Mediated Adhesive Interaction with Activated Platelets," Biochem. Biophys. Res. Common., 172:1349-1356, (1990).

Corson, Timothy W. et al., "Design and Applications of Bifunctional Small Molecules: Why Two Heads Are Better Than One," ACS Chemical Biology 3(11):677-692, Nov. 2008.

Cossu et al., "Serum levels of vascular dysfunction markers reflect disease severity and stage in systemic sclerosis patients," Rheumatology, 2016; 55:1112-116.

Cottler-Fox, M.H. et al., "Stem Cell Mobilization," Amer. Sci. Hematology, 419-437, (2003).

Crawford et al., "AMD070, a CXCR4 Chemokine Receptor Antagonist: Practical Large-Scale Laboratory Synthesis," Org. Process Res. Devel. 12:823-830, 2008.

Cumpstey, I. et al. "C2-Symmetrical Thiodigalactoside Bis-Benzamido Derivatives as High-Affinity Inhibitors of Galectin-3: Efficient Lectin Inhibition through Double Arginine-Arene Interactions," Angew Chem., 117:5240-5242 (2005).

Dagia, Nilesh et al., "G-CSF induces E-selecting ligand expression on human myeloid cells," Nature Medicine, 12(10): 1185-90, Oct. 1, 2006.

Daoudii, Jean-Michel et al., "New bicyclam-GalCer analogue conjugates: synthesis and in vitro anti-HIV activity," Bioorg. & Med. Chem. Letters 14:495-498, 2004.

Datta et al., "Isolation and purification of trehalose 6-mono-and 6,6'-di-corynomycolates from Cornyebacterium matruchotii. Structural characterization of .sup.1H NMR," Carbohydrate Research 245: 151-158, 1993.

DeAngelo et al., "Results of a Phase 1 Study of GMI-1271, A Novel E-Selectin Antagonist in Combination with Induction Chemotherapy in Relapsed/Refractory AML: A Novel, Well-Tolerated Regimen with a High Remission Rate," Haematologica, 101 (s2), Abstract P191, #133179, May 19, 2016.

(56) References Cited

OTHER PUBLICATIONS

DeAngelo et al., "Results of a Phase I Study of GMI-1271, a Potent E-Selectin Antagonist in Combination with Induction Chemotherapy in Relapsed/Refractory AML: A Novel, Well-Tolerated Regimen with a High Remission Rate," Proceedings of the European Hematology Society 21st Congress, Poster Presentation, #133179, Copenhagen, Denmark, Jun. 10, 2016.

DeAngelo et al., "A Phase I/II Study of GMI-1271, a Novel E-Selectin Antagonist, in Combination with Induction Chemotherapy inf Relapsed/Refractory and Elderly Previously Untreated Acute Myeloid Leukemia; Results to Date," Blood, 128(22) Abstract #4049, Dec. 2, 2016.

DeAngelo et al., "A Phase I/II Study of GMI-1271, a Novel E-selectin Antagonist, in Combination with Induction Chemotherapy in Relapsed/Refractory and Previously Untreated Elderly Patients with Acute Meyloid Leukemia; Results to Date," Proceedings of the 58th Annual Meeting of the American Society of Hematology, Abstract #4049, Poster Presentation on Dec. 5, 2016, San Diego, CA.

DeAngelo et al., "GMI-1271, a novel E-selectin antagonist, combined with induction chemotherapy in elderly patients with untreated AML," Journal of Clinical Oncology, 35 (15 Supplement), Abstract #2560, May 20, 2017.

DeAngelo et al., "GMI-1271, a Potent E-Selectin Antagonist, Combined with Induction Chemotherapy in Elderly Patients with Untreated AML: A Novel, Well-Tolerated Regimen with A High Remission Rate," Haematologica, 102 (s2), #181490, Jun. 2017.

DeAngelo et al., "GMI-12751, A Potent E-Selectin Antagonist, In Combination with Chemotherapy In Relapsed/Refractory AML: A Novel, Well-Tolerated Regimen with A High Remission Rate," Haematologica, 102 (s2), #181834, Jun. 2017.

DeAngelo et al., "GMI-1271, a Potent E-Selectin Antagonist, in Combination with Chemotherapy in Relapsed/Refractory AML: A Novel, Well-Tolerated Regimen with a High Remission Rate," Proceedings of the European Hematology Society 22nd Congress, Poster Presentation, #181834, Madrid, Spain, Jun. 23, 2017.

DeAngelo et al., "GMI-1271, a Potent E-Selectin Antagonist, Combined with Induction Chemotherapy in Elderly Patients with Untreated AML: A Novel, Well-Tolerated Regimen with a High Remission Rate," Proceedings of the European Hematology Society 22nd Congress, Poster Presentation, #181490, Madrid, Spain, Jun. 24, 2017.

DeAngelo et al., "GMI-1271, a Novel E-Selectin Antagonist, Combined with Induction Chemotherapy in Elderly Patients with Untreated AML," Proceedings of the Annual Meeting of the American Society of Clinical Oncology, #2560, Poster Presentation, Jun. 2-6, 2017, Chicago, IL.

Deangelo et al., "GMI-1271, a Novel E-Selectin Antagonist, in Combination with Chemotherapy in Relapsed/Refractory AML," Proceedings of the Annual Meeting of the American Society of Clinical Oncology, #2520, Poster Presentation, Jun. 2-6, 2017, Chicago, IL.

DeAngelo et al., "GMI-1271 Improves Efficacy and Safety of Chemotherapy in RR and Newly Diagnosed Older Patients with AML: Results of a Phase 1/2 Study," Proceedings of the 59th American Society of Hematology Annual Meeting, Oral Presentation, Dec. 11, 2017, Atlanta, GA.

DeAngelo et al., "Uproleselan (GMI-1271), an E-selectin antagonist, improves efficacy and safety of chemotherapy in R/R and newly diagnosed older patients with AML: final, correlative, and subgroup analysis," Proceedings of the 60th American Society of Hematology Annual Meeting, Oral Presentation, Dec. 2, 2018, San Diego, CA.

Huang et al., "Postischemic Cerebrovascular E-Selectin Expression Mediates Tissue Injury in Murine Stroke," Stroke, 31, 3047-3053, 2000.

Huse et al., "Generation of a Large Combinatorial Library of the Immunoglobulin Repertoire in Phage Lambda," Science 246:1275-1281, 1989.

Huwe, C. M. et al., "Design, Synthesis and Biological Evaluation of Aryl-substituted Sialyl Lewis X Mimetics Prepared Via Cross-metathesis of C-Fucopeptides," Biological & Medicinal Chemistry 7:773-788, 1999.

Hynes, R., "Integrins: A Family of Cell Surface Receptors," Cell 48:549-554, 1987.

Ikeuchi, Yoshihiro et al., "Synthesis and Antitumor Activities of Novel 5-Deazaflavin-Sialic Acid Conjugate Molecules," Bioorg. & Med. Chem. 8:2027-2035, 2000.

International Search Report dated Mar. 21, 2019, for International Application No. PCT/US2018/062988 (4 pages).

Inwald, D. P. et al., "Platelet and leucocyte activation in childhood sickle cell disease: association with nocturnal hypoxaemia," British Journal of Haematologyl 11:474-481, Nov. 2000.

Ishikawa, F. et al., "Chemotherapy-resistant human AML stem cells home to and engraft within the bone-marrow endosteal region," Nature Biotechnology 25(11):1315-1321, Nov. 2007.

Issekutz, T., "Inhibition of in Vivo Lymphocyte Migration of Inflammation and Homing to Lymphoid Tissues by the TA-2 Monoclonal Antibody. A Likely Role for VLA-4 in Vivo," Journal of Immunology 147:4178-4184, 1991.

Itai, S. et al., "Differentiation-dependent Expression of I and Sialyl I Antigens in the Developing Lung of Human Embryos and in Lung Cancers," Cancer Research 50: 7603-7611, 1990.

Jeffrey et al., "Affinity Chromatography of Carbohydrate-Specific Immunoglobulins: Coupling of Oligosaccharides to Sepharose ," Biochem. Biophys. Res. Common. 62:608-613, 1975.

Jentsch, K.D. et al., "Inhibition of Human Immunodeficiency Virus Type I Reverse Transcriptase by Suramin-related Compounds," The Journal of General Virology 68(8): 2183-2192, 1987.

Jentsch, TJ et al. "Ion Channels: Function Unravelled by Dysfunction," Nature Cell Biology, 6(11): 1039-1047 (Nov. 2004).

Jiang et al., "CD33 in Alzheimer's Disease," Molecular Neurobiology, 46, 529-535, 2014.

Ju et al., "Dual E-Selectin and CXCR4 Inhibition Reduces Tumor Growth and Metastatic Progression in an Orthotopic Model of Osteosarcoma,"Abstract #5211, Proceedings of the American Association for Cancer Research Annual Meeting, Apr. 14-18, 2018, Chicago, IL.

Ju et al., "Abstract 5211: Dual E-selectin and CXCR4 inhibition reduces tumor growth and metastatic progression in an orthotopic model of osteosarcoma," Cancer Research, 78(13 Supplement), Abstract #5211, Jul. 2018.

Jubeli et al., "E-selectin as a target for drug delivery and molecular imaging," Journal of controlled Release, 158, 194-206, 2012.

Jubeli et al., "Preparation of E-selectin-targeting nanoparticles and preliminary in vitro evaluation," International Journal of Pharmaceutics, 426(2012), 291-301.

Juliusson et al., "Age and acute myeloid leukemia: real world data n decision to treat and outcomes from the Swedish Acute Leukemia Registry," Blood, 113, 4170-4187, 2009.

Kaila, N. et al., "Design and synthesis of sialyl Lewis(x) mimics as E-and P-selectin inhibitors," Med Res Rev 22(6):566-601, Nov. 2002.

Kaila, N. et al., "ß-C-Mannosides as Selectin Inhibitors," Journal of Medicinal Chemistry 45(8): 1563-1566, 2002.

Kannagi et al., "New Globoseries Glycosphingolipids in Human Teratocarcinoma Reactive with the Monoclonal Antibody Directed to a Developmentally Regulated Antigen, Stage-specific Embryonic Antigen 3," J. Biol. Chem. 258(14):8934-8942, 1983.

Kannagi et al., "Stage-specific embryonic antigens (SSEA-3 and -4) are epitopes of a unique globo-series ganglioside isolated from human teratocarcinoma cells," Embo J. 2(12):2355-2361, 1983.

Kannagi, "Transcriptional regulation of Expression of Carbohydrate Ligands for Cell Adhesion Molecules in the Selectin Family[a,b]," The Molecular Immunology of Complex Carbohydrates-2, edited by Albert M. Wu, Kluwer Academic/Plenum Publishers, 2001, pp. 267-278.

Kannagi, R. et al. "Carbohydrate-mediated cell adhesion in cancer metastasis and angiogenesis," Cancer Sci., 95(5): 377-384 (2004).

Kansas, G., "Selectins and Their Ligands: Current Concepts and Controversies," Blood, 88(9): 3259-3287 (1996).

(56) References Cited

OTHER PUBLICATIONS

Karaivanova et al., "Partial Characterization of Microsomal Sialyltransferase From Chicken Liver and Hepatoma Mc-29: II. Measurement of Enzyme Activities Utilizing Microsomal Glycoproteins as Exogenous Acceptors," Cancer Biochem. Biophys. 11:311-315, 1990.
Katayama, Y. et al., "PSGL-1 Participates In E-Selectin-Mediated Progenitor Homing To Bone Marrow: Evidence For Cooperation Between E-Selectin Ligands And a4 Integrin," Blood, 102:2060-2067, (2003).
Katayama, Y., et al., "CD 44 is a physiological E-selectin ligand on neutrophils", J. Exp. Med. 201(8), (2005), 1183-1189.
Kaul, D.K. et al., "Hypoxia/reoxygenation causes inflammatory response in transgenic sickle mice but not in normal mice," The Journal of Clinical Investigation 106(3):411-420, Aug. 2000.
Khatib, A.-M., et al., "Inhibition of Hepatic Endothelial E-Selectin Expression by C-raf antisense Oligonucleotides Blocks Colorectal Carcinoma Liver Metastasis", Cancer Research 62(19), (2002), 5393-5398.
Kiel, M. J., et al., "SLAM Family Receptors Distinguish Hematopoietic Stem and Progenitor Cells and Reveal Endothelial Niches for Stem Cells" Cell 121 (7) (2006}, 11 09-1121.
Kilgore et al., "Reducation of myocardial infarct size in vivo by carbohydrate-based glycomimetics" Journal of Pharmacology and Experimental Therapeutics, American Society for Pharmacology and Experimental Therapeutics, 284(1):427-435 (1998).
Kim et al., "Altered Expression of Lewis Antigen on Tissue and Erythrocytes in Gastric Cancer Patients," Yonsei Medical Journal, vol. 43, No. 4, pp. 427-434, 2002.
Kim et al., "Inhibition of the CXCR4/CXCL12 Chemokine Pathway Reduces the Development of Murine Pulmonary Metastases," Clin. Exp. Metastasis 25(3):201-211, 2008.
Kitagawa et al., "Immunoaffinity Isolation of a Sialyl-Le$^a$ Oligosaccharide from Human Milk," J. Biochem. 104:591-594, 1988.
Kitagawa et al., "Characterization of Mucin-Type Oligosaccharides With the Sialyl-Le.sup.a Structure From Human Colorectal Adenocarcinoma Cells," Biochem. Biophys. Res. Common. 178(3):1429-1436, 1991.
Klyosov et al., "Galectins in Disease and Potential Therapeutic Approaches," In Galectins and Disease Implications for Targeted Therapeutics, American Chemical Society, Washington, DC, Chapter 1, pp. 3-43, 2012.
Kneuer et al: "Selectins—potential pharmacological targets?" Drug Discovery Today vol. 11, No. 21-22, pp. 1034-1040, Oct. 2006.
Ko, HL et al. "In Vitro and In Vivo Inhibition of Lectin Mediated Adhesion of Pseudomonas aeruginosa by Receptor Blocking Carbohydrates," Infection, 15(4): 21-24 (1987).
Kobayashi et al., "Cimetidine Inhibits Cancer Cell Adhesion to Endothelial Cells and Prevents Metastasis by Blocking E-selectin Expression," Cancer Research, 60, 3978-3984, 2000.
Koch, Alisa E et al., "Angiogenesis mediated by soluble forms of E-selectin and vascular cell adhesion molecule-1," Nature, 376(6540): 517-519 (1995).
Koenig et al., "Selectin Inhibition: Synthesis and Evaluation of Novel Sialylated, Sulfated and Fucosylated Oligosaccharides, Including the Major Capping Group of Glycam-1", Glycobiology, 7(1):79-93 (1997).
Kogan, T.P. et al., "Rational Design and Synthesis of Oligosaccharide Mimetics: Selectin Antagonists as Cell Adhesion Inhibitors," Abstracts of Papers, 210.sup.th ACS National Meeting, American Chemical Society, Chicago, IL, Aug. 20-24, 1995, MEDI-18.
Kogan, T.P. et al., "Rational Design and Synthesis of Small Molecule, Non-oligosaccharide Selectin Inhibitors: (.alpha.-D-Mannopyranosyloxy)biphenyl-Substituted Corboxylic Acids," J. Med. Chem. 38: 4976-4984, Dec. 22, 1995.
Kogan, T.P. et al., "Novel Synthetic Inhibitors of Selectin-Mediated Cell Adhesion: Synthesis of 1,6-Bis[3-(3-carboxymethylphenyl)-r-(2-.alpha.-.sub.D-monnopyranosyloxy)p- henyl]hexane (TBC1269)," J Med. Chem 41:1099-1111, 1998.

Kohler et al., "Continuous cultures of fused cells secreting antibody of predefined specificity," Nature 256:495-497, 1975.
Kohler et al., "Derivation of specific antibody-producing tissue culture and tumor lines by cell fusion," Eur. J. Immunol. 6:511-519, 1976.
Kojima et al., "Specific Interaction between Gangliotriaosylceramide (G.sub.g3) and Sialosyllactosylceramide (G.sub.M3) as a Basis for Specific Cellular Recognition between Lymphoma and Melanoma Cells," J. Biol. Chem. 264(34):20159-20162, 1989.
Kolb et al., "Development of Tools for the Design of Selectin Antagonists," Chem. Eur. J. 3(10):1571-1578, 1997.
Kolb et al., "Recent progress in the glycodrug area," Pure & Applied Chemistry 69(9):1879-1884, 1997.
Komrokji et al., "The Colony-Stimulating Factors: Use to Prevent and Treat Neutropenia and Its Complications," Expert Opin.Biol. Ther., 4:1897-1910, (2004).
Koprowski et al., "Colorectal Carcinoma Antigens Detected by Hybridoma Antibodies," Somatic Cell Genetics 5(6):957-972, 1979.
Kulidjian et al., "Differential role of E-selectin and P-selectin in T lymphocyte migration to cutaneous inflammatory reactions induced by cytokines," International Immunology, 14(7), 751-760, 2002.
Kuuliala et al., "Circulating soluble E-selectin in early rheumatoid arthritis: a prospective five year study," Annals of Rheumatic Diseases, 61, 242-246, 2002.
Kuznetsova et al., "Targeting liposomes loaded with melphalan prodrug to tumour vasculature via the Sialyl Lewis X selectin ligand," J. Drug Target. 2014, 22(3):242-250.
Kuzuoka, "Antitumor activity of murine monoclonal antibody NCC-ST-421," Chem. Ab. 115:27344v, 1991.
Kwiatskowski et al., "Tautomerism and Electronic Structure of Biological Pyrimidines" Adv Het Chem 1975, pp. 199-335.
Kwong et al., "An Antagonist of the Chemokine Receptor CXCR4 Induces Mitotic Catastrophe in Ovarian Cancer Cells," Mol. Cancer Ther. 8(7): 1893-1905, Jul. 2009.
Kwong, P. D. et al., "Rational Design of Vaccines to Elicit Broadly Neutralizing Antibodies to HIV-1," Cold Spring Harbor Perspectives in Medicine 1-16, 2011.
Kyriakides et al., "Endothelial selectin blockade attenuates lung permeability of experimental acid aspiration," Surgery, 128(2):327-31, Aug. 2000.
Laird et al., "P-and E-selectin receptor antagonism prevents human leukocyte adhesion to activated porcine endothelial monolayers and attenuates porcine endothelial damage," Xenotransplantation, 25:e12381, 2018.
Lamblin et al., "Primary Structure Determination of Five Sialylated Oligosaccharides Derived from Bronchial Mucus Glycoproteins of Patients Suffering from Cystic Fibrosis.," Journal of Biological Chemistry 259(14):9051-9058, 1984.
Lanne, B. et al., "Binding of the galactose-specific Pseudomonas aeruginose lectin, PA-I, to glycosphingolipids and other glycoconjugates," Glycoconjugate Journal, 11:292-298 (1994).
Larsen et al., "PADGEM-Dependent Adhesion of Platelets to Monocytes and Neutrophils is Mediated by a Lineage-Specific Carbohydrate, LNF III (CD15)," Cell 63:467-474, 1990.
Lee et al., "A new method of sequencing linear oligosaccharides on gels using charged, fluorescent coniugates" Carbohydrate Research, vol. 214, 1991, pp. 155-168, XP000226749.
Lemoli et al., "Hematopoietic stem cell mobilization," Haematologica, 93 (3): 321-324 (2008).
Leppla, S H et al., "Anthrax Toxin Fusion Proteins For Intracellular Delivery Of Macromolecules," Journal Of Applied Microbiology., 87(2): p. 284 (Aug. 1, 1999).
Ley, K., "The role of selectins in inflammation and disease," Trends in Molecular Medicine, 9(6): 263-268 (Jun. 2003).
Ley, K. et al., "Selectins in T-cell Recruitment to Non-Lymphoid Tissues and Sites of Inflammation," Nature Reviews, 4: 1-11 (May 2004).
Li, B., et al., "Delaying Acute Graft-Versus-Host Disease in Mouse Bone Marrow Transplantation by Treating Donor Cells with Antibodies Directed at L-Selectin and a4 Integrin Prior to Infusion," Scand. J, I Immunol 59:464-468, 2004.

(56) References Cited

OTHER PUBLICATIONS

Li et al., "α1,3 Fucosyltransferase VII plays a role in colorectal carcinoma metastases by promoting the carbohydration of glycoprotein CD24," Oncology Reports, 23:1609-1617, 2010.
Li et al., "Increased CSF E-Selectin in Clinical Alzheimer's Disease without Altered CSF A$\beta_{42}$ and Tau," Journal of Alzheimer's Disease, 47, 883-887, 2015.
Li et al., "Hematopoietic-Derived Galectin-3 Causes Cellular and Systemic Insulin Resistance," Cell, 167, 973-984, 2016.
Liang et al., "Clinicopathological and prognostic significance of sialyl Lewis X overexpression in patients with cancer: a meta-analysis," Onco Targets and Therapy, 9, 3113-3125, 2016.
Lindenberg et al., "Carbohydrate binding properties of mouse embryos," J. Reprod. Fert. 89:431-439, 1990.
Lipartiti et al., "Monosialoganglioside GM1 Reduces NMDA Neurotoxicity in Neonatal Rat Brain," Experimental Neurology 113:301-305, 1991.
Liu et al., "Altering the Specificity of the Antibody Response to HIV gp120 with a Glycoconjugate Antigen,"ACS Chemical Biology, 11, 1702-1709, 2016.
Liu et al., "Broadly Neutralizing Antibody-Guided Carbohydrate-Based HIV Vaccine Design: Challenges and Opportunities," ChemMedChem, 11, 357-362, 2016.
Llmer et al., "Cell surface galectin-3 defines a subset of chemoresistant gastrointestinal tumorinitiating cancer cells with heightened stem cell characteristics," Cell Death and Disease, 7, e2337, 1-9, 2016.
Loetscher et al., "N-terminal Peptides of Stromal Cell-derived Factor-1 with CXC Chemokine Receptor 4 Agonist and Antagonist Activities," J. Biol. Chem. 273(35):22279-22283, 1998.
Lowe et al., "ELAM-1-Dependent Cell Adhesion to Vascular Endothelium Determined by a Transfected Human Fucosyltransferase cDNA," Cell 63:475-484, 1990.
Lowe et al., "A transfected human fucosyltransferase cDNA determines biosynthesis of oligosaccharide ligand(s) for endothelial-leukocyte adhesion molecule I," Biochem. Soc. Trans. 19(3):649-653, 1991.
Luallen, R. J. et al., "A Yeast Glycoprotein Shows High-Affinity Binding to the Broadly Neutralizing Human Immunodeficiency Virus Antibody 2G12 and Inhibits gp120 interactions with 2G12 and DC-SIGN," Journal of Virology 83(1):4861-4870, May 2009.
Macher et al., "A Novel Carbohydrate, Differentiation Antigen on Fucogangliosides of Human Myeloid Cells Recognized by Monoclonal Antibody VIM-2," Journal of Biological Chemistry 263(21):10186-10191, 1988.
Magnani et al., "A Monoclonal Antibody-defined Antigen Associated with Gastrointestinal Cancer Is a Ganglioside Containing Sialylated Lacto-N-fucopentaose II," Journal of Biological Chemistry 257(23):14365-14369, 1982.
Magnani et al., "Identification of the Gastrointestinal and Pancreatic Cancer-associated Antigen Detected by Monoclonal Antibody 19-9 in the Sera of Patients as a Mucin," Cancer Res. 43:5489-5492, 1983.
Magnani, J., "Carbohydrate Sequences Detected by Murine Monoclonal Antibodies," Chemistry and Physics of Lipids 42:65-74, 1986.
Magnani, J., "Potent Glycomimetic Inhibitors of the Adhesion Molecule, PA-IIL, for the Bacterial Pathogen, Pseudomonas auroginosa," Glycobiology 13(11): 854, Abstract No. 104, Oct. 2003.
Magnani, "The Discovery, Biology, and Drug Development of Sialyl Le$^a$ and Sialyl Le$^x$", Archives of Biochemistry and Biophysics, 426:122-131, May 8, 2004.
Magnani et al., "Glycomimetic Drugs—A New Source of Therapeutic Opportunities," Discovery Medicine, 8(43), 247-252, 2009.
Magnani et al., "Pan-selectin Antagonist GMI-1070 affects Biomarkers of Adhesion, Activation and the Coagulation Cascade in Sickle Cell Adults at Steady State", Blood, 120, Abstract #87, Nov. 2012.
Magnani, "A Potent Glycomimetic Antagonist (GMI-1271) of E-selectin in Phase 1/2 Clinical Trials forthe Treatment of Acute Myelogenous Leukemia," 1271 Treatment of AML Presented on Glycoscience Research Day at the NIH on Jul. 11, 2017.
Magro et al., "Cutaneous lymphocyte antigen expression in benign and neoplastic cutaneous B-and T-cell lymphoid infiltrates," J. Cutan. Phathol., 2008:35:1040-1049.
Maly, P., et al., "The α(1,3)Fucosyltransferase Fuc-TVII Controls Leukocyte Trafficking through an Essential Role in L-, E-, and P-selection Ligand Biosynthesis", Cell. 86(4), It 1996), 643-653.
Mann, AP et al., "Identification of Thioaptamer Ligand against E-Selectin: Potential Application for Inflamed Vasculature Targeting," PLoS ONE, 5(9): 1-11 (Sep. 2010).
Matsuda, Masao et al., "Heterobifunctional Ligands: Practical Chemoenzymatic Synthesis of a Cell Adhesive Glycopeptide That Interacts With Both Selectins and Integrins," J. Med. Chem. 44:715-724, 2001.
Matsui, N. M. et al., "The Novel Adhesion of Erythrocytes to P-Selectin in Sickle Cell Disease," Blood 96(11) Pt. 1:600a, Abstract #2575, Nov. 16, 2000.
Matsui, N. M. et al., "P-selectin mediates the adhesion of sickle erythrocytes to the endothelium," Blood 98(6):1955-1962, Sep. 15, 2001.
Matsui, N. M. et al., "Heparin inhibits the flow adhesion of sickle red blood cells to Pselectin," Blood 100(10):3790-3796, Nov. 15, 2002.
Shan, M. et al., "HIV-1 gp120 Mannoses Induce Immunosuppressive Responses from Dendritic Cells," PLoS Pathogens 3(11):e169 1637-1650, Nov. 2007.
Sheen-Chen et al., "Serum levels of soluble E-selectin in women with breast cancer," British Journal of Surgery, 91, 1578-1581, 2004.
Shitara et al., "Application of Anti-Sialyl Le.sup.a Monoclonal antibody, KM231, for Immunotherapy of Cancer," Anticancer Res. 11:2003-2014, 1991.
Simanek et al. "Selectin-carbohydrate interactions: from natural ligands to designed mimics", Chemical Reviews vol. 98, No. 2, pp. 833-862, Jan. 1998.
Simon et al., "Mightier than the sickle cell (editorial)", Blood, 116(10), 1633, Sep. 9, 2010.
Simon et al., "Effects of Selectin Antagonist GMI-1070 on the Activation State of Leukocytes in Sickle Cell Patients not in Crisis" ASH Annual Meeting 2010, Poster #32407, Dec. 6, 2010.
Simon et al., "Inhibition of E-Selectin Inflammatory Function by the Glycomimetic GMI-1070" Blood, 118, Abstract #851, Nov. 2011.
Singh et al., "Evaluation of a CXCR4 Antagonist in a Xenograft Mouse Model of Inflammatory Breast Cancer," Clin. Exp. Metastasis 27:233-240, Mar. 2010.
Sipkins et al., "In Vivo Imaging of Specialized Bone Marrow Endothelial Microdomains for Tumor Engraftment," Nature Pub. Group GB 435 (7044):969-973, Jun. 2005.
Siuzdak et al., "Examination of the Sialyl Lewis X—Calcium Complex by Electrospray Mass Spectrometry," Bioorganic & Medicinal Chemistry Letters 4(24): 2863-2866, 1994.
Smith et al., "Abstract 2867: Glycomimetic antagonist of E-selectin, GMI-1271, enhances therapeutic activity of the hypomethylating agent 5-azacitidine in the KG1 model of AML," Cancer Research, 78(13 Supplement), Abstract #2867, Jul. 2018.
Solovey et al., "Circulating Activated Endothelial Cells in Sickle Cell Anemia," The New England Journal of Medicine 337:1584-1590, Nov. 27, 1997.
Solovey et al. "Modulation of endothelial cell activation in sickle cell disease: a pilot study," Blood, 97(7): 1937-1941 (Apr. 2001).
Spivak et al., "Low-Dose Molecular Ultrasound Imaging with E-Selectin-Targeted PBCA Microbubbles," Mol. Imaging Biol., (2016), 18:180-190.
Sprengard et al., "Synthesis and Biological Activity of Novel Sialyl-Lewis.sup.X Conjugates," Bioorganic & Medicinal Chemistry Letters 6(5): 509-514, 1996.
Stahn et al., Multivalent sialyl Lewis x ligands of definite structures as inhibitors of E-selectin mediated cell adhesion, Glycobiology, vol. 8, No. 4, 1998, pp. 311-319.
Stanley et al., "The LEC11 Chinese Hamster Ovary Mutant Synthesizes N-Linked Carbohydrates Containing Sialylated, Fucosylated Lactosamine Units. Analysis by One-and Two-Dimensional H NMR Spectroscopy," J. Biol. Chem. 263(23):11374-11381, 1988.

(56) References Cited

OTHER PUBLICATIONS

Steele et al., "#4503 A Small Molecule Glycomimetic Antagonist of E-selectin (GMI-1271) Prevents Pancreatic Tumor Metastasis and Offers Improved Efficacy of Chemotherapy," Proceedings of the 105th Annual Meeting of the American Association for Cancer Research, Abstract #4503, Apr. 5-9, 2014, San Diego, CA.
Steele et al., "A Small Molecule Glycomimetic Antagonist of E-selectin (GMI-1271) Prevents Pancreatic Tumor Metastasis and Offers Improved Efficacy of Chemotherapy", AACR Annual Meeting 2014, Poster #4503, Apr. 8, 2014.
Steele et al., "Abstract 4503: A small molecule glycomimetic antagonist of E-selectin (GMI-1271) prevents pancreatic tumor metastasis and offers a novel treatment for improved efficacy of chemotherapy," Cancer Research, 74(19 Supplement), Abstract #4503, Oct. 2014.
Steele et al., "425 A small molecule glycomimetic antagonist of E-selectin and CXCR4 (GMI-1359) prevents pancreatic tumor metastasis and offers improved chemotherapy" Cancer Research, Aug. 2015.
Steele et al., "A small molecule glycomimetic antagonist of E-selectin and CXCR4 (GMI-1359) prevents pancreatic tumor metastasis and improves chemotherapy," Cancer Research, 75(15 Supplement), 425-426, Aug. 2, 2015.
Steele et al., "A small molecule glycomimetic antagonist of E-selectin and CXCR4 (GMI-1359) delays pancreatic tumor metastasis and significantly alters the pancreatic tumor microenvironment," Proceedings of the 107th Annual Meeting of the American Association for Cancer Research, Abstract #902, Apr. 16-20, 2016, New Orleans, LA.
Steele et al., "A small molecule glycomimetic antagonist of E-selectin and CXCR4 (GMI-1359) delays pancreatic tumor metastasis and significantly alters the pancreatic tumor microenvironment," Cancer Research, 76(14 Supplement), Abstract #902, Jul. 2016.
Stephens et al.,"The construction of highly efficient and versatile set of mammalian expression vectors," Nucleic Acids Research. 17:7110, 1989.
Stevenson et al., "Differential metastasis inhibition by clinically relevant levels of heparins," Clin. Cancer Res. 11(19): 7003-7011 (2005).
Streeter et al., "Immunohistologic and Functional Characterization of a Vascular Addressin Involved in Lymphocyte Homing into Peripheral Lymph Nodes," Journal of Cell Biology 107: 1853-1862, 1988.
Stroud et al. ,"Extended Type 1 Chain Glycosphingolipids: Dimeric Le.sup.a (III.sup.4V.sup.4Fuc.sub.2Lc.sub.6) as Human Tumor-associated Antigen," J. Biol. Chem. 266(13):8439-8446, 1991.
Styles et al., GMI-1070, a Pan-Selectin Inhibitor: Safety and PK in a Phase 1/2 Study in Adults with Sickle Cell Disease, ASH Annual Meeting 2010, Poster #31824, Dec. 4, 2010.
Sudhoff et al., "Cutting Edge Communication: Circulating Endothelial Adhesion Molecules (sE-Selectin, sVCAM-1 and SICAM-1) During rHuG-CSF-Stimulated Stem Cell Mobilization," Jour. Hematother. & Stem Cell Res., 11:147-151 (2002).
Suzuma et al., "Contribution of E-Selectin to Cellular Infiltration during Endotoxin-Induced Uveitis," Invest. Ophthalmol. Vis. Sci., 39: 1620-1630 (1998).
Svenson et al., "Coupling of Acid Labile *Salmonella* Specific Oligosaccharides to Macromolecular Carriers," J. Immunol. Meth. 25:323-335, 1979.
Symon et al., "Selectins and their Counter receptors: a bittersweet attraction," Thorax, 51: 1155-1157 (1996).
Tabarani et al., "Mannose Hyperbranched Dendritic Polymers Interact with Clustered Organization of DC-SGIN and Inhibit gp120 Binding," FEBS Letters 580:2402-2408, Mar. 2006.
Takada et al., "Adhesion of Human Cancer Cells to Vascular Endothelium Mediated by a Carbohydrate Antigen, Sialyl Lewis A[1]," Biochem. Biophys. Res. Common. 179(2):713-719, 1991.
Takahashi et al., "Design and Synthesis of a Water-Soluble Taxol Analogue : Taxol-Sialyl Conjugate," Bioorg. & Med. Chem. Letters 8:113-116, 1998.

Takeichi, "Cadherins: a molecular family essential for selective cell-cell adhesion and animal morphogenesis," Trends Genet. 3(8):213-217, 1987.
Tamamura. et al., "Identification of a New Class of Low Molecular Weight Antagonists against the Chemokine Receptor CXCR4 Having the Dipicolylamine-Zinc(II) Complex Structure" J. Med. Chem., 49: 3412-3415 (2006).
Tanaka et al., "Azamacrocyclic Metal Complexes as CXCR4 Antagonists," ChemMedChem, 6: 834-839 (2011).
Taniguchi et al., "Serum Levels of Galectin-3: Possible Association with Fibrosis, Aberrant Angiogenesis, and Immune Activation in Patients with Systemic Sclerosis," The Journal of Rheumatology, 39(3), 539-544, Mar. 2012.
Tchinda et al., "Severe malaria in Cameronian children: correlation between plasma levels of three soluble inducible adhesion molecules and TNF-α," Acta Tropica, 102(2007), 20-28.
Tedder et al., "The selectins: vascular adhesion molecules," FASEB J, 9(10): 866-73 (1995).
Tejler et al., "Synthesis of galactose-mimicking 1H-(1,2,3-triazol-1-yl)-mannosides as selective galectin-3 and 9N inhibitors," Carbohydrate Research, 342(12-13), 1869-1875, 2007.
Tejler et al., "Fragment-based development of triazole-substituted O-galactosyl aldoximes with fragment-induced affinity and selectivity for galectin-3," Organic & Biomolecular Chemistry, 19(7), 3982-3992, 2009.
Telen et al., "GMI 1070: Reduction In Time To Resolution Of Vaso-Occlusive Crisis and Decreased Opioid Use In a Prospective, Randomized, Multi-Center Double Blind, Adaptive Phase 2 Study In Sickle Cell Disease" Blood, 122(21):776, Nov. 15, 2013.
Telen et al., "Randomized phase 2 study of GMI-1070 in SCD: reduction in time to resolution of vaso-occlusive events and decreased opioid use", Blood, 125(17):2656-2664, Apr. 23, 2015.
The Merck Manual of Diagnosis and Therapy, Seventeenth Edition, published 1999 by Merck Research Laboratories, pp. 397, 398, 948,949, 1916, 1979-1981.
Thoma, G. et al., "Synthesis and biological evaluation of a potent E-selectin antagonist," J. Med. Cherm. 42 (23): 4909-4913, Nov. 18, 1999.
Thoma G et al., "A readily Available, Highly Potent E-Selectin Antagonist," Angew. Chem. Int. Ed. 40(19): 3644-3647, 2001.
Thoma, G. et al., "Preorganization of the Bioactive Conformation of Sialyl Lewis[x] Analogues Correlates with Their Affinity to E-Selectin," Angew. Chem. Int. Ed. 40(10): 1941-1945, 2001.
Thoma, G. et al., "Synthesis and Biological Evaluation of a Sialyl Lewis X Mimic with Significantly Improved E-selectin Inhibition," Bioorganic & Medicinal Chemistry Letters 11: 923-925, 2001.
Thoma, G et al., "Nanomolar E-selectin inhibitors: 700-fold potentiation of affinity by multivalent ligand presentation,"Journal Of The American Chemical Society, 123(41): 10113-10114 (Oct. 17, 2001).
Tilton, R.G., "Endotoxin-Induced Leukocyte Accumulation in Aqueous Fluid of Rats is Decreased by a Small Molecule Selectin," Investigative Opthalmology & Visual Science 37(3): S918, Abstract No. 4227, Feb. 15, 1996.
Titz et al., "Mimetics of Sialyl Lewis[x]: The Pre-Organization of the Carboxylic Acid is Essential for Binding to Selectins", Chimia, 61:194-197, 2007.
Titz et al., "Is adamantine a suitable substituent to pre-organize the acid orientation in E-selectin antagonists?", Bioorganic & Medicinal Chemistry, 16 (2008), 1046-1056.
Titz, A. et al., "Probing the carbohydrate recognition domain of E-selectin: The importance of the acid orientation in sLex mimetics," Bioorg. Med. Chem., 18(1): 19-27 (2010).
Todderud et al., "BMS-190394, a Selectin Inhbitor, Prevents Rat Cutaneous Inflammatory Reactions," J Pharmacal Exp Ther., 282(3):1298-304, Sep. 1997.
Toepfer et al., "Synthesis of Novel Mimetics of the Sialyl Lewis X Determinant," Tetrahedron Letters, vol. 36, No. 50, pp. 9161-9164, 1995.
Togel et al., "Administered mesenchymal stem cells protect against ischemic acute renal failure through differentiation-independent mechanisms," Am. J. Physical Renal Physiol., 289:F31-42, Jul. 2005.

(56) References Cited

OTHER PUBLICATIONS

Totani, K. et al., "Chemoenzymatic synthesis and application of glycopolymers containing multivalent sialyloligosaccharides with a poly(L-glutamic acid) backbone for inhibition of infection by influenza viruses," Glycobiology, 13(5): 315-326 (2003).
Trøseid et al., "Changes in serum levels of E-selectin correlate to improved glycaemic control and reduced obesity in subjects with the metabolic syndrome," Scand J Clin Lab Invest, 2005, 65:283-290.
Trouet et al., "A covalent linkage between daunorubicin and proteins that is stable in serum and reversible by lysosomal hydrolases, as required for a lysosomotropic drug-carrier conjugate: In vitro and in vivo studies," Proc. Natl. Acad. Sci. USA 79:626-629, 1982.
Tsoref et al., "E-selectin-targeted copolymer reduces atherosclerotic lesions, adverse cardiac remodeling, and dysfunction," Journal of Controlled Release, 288(2018), 136-147.
Tsuruta et al., "Application of liposomes incorporating doxorubicin with sialyl Lewis X to prevent stenosis after rat carotid artery injury," Biomaterials, 30(2009), 118-125.
Turhan, et al., "Primary role for adherent leukocytes in sickle cell vascular occlusion: A new paradigm," Proceedings of the National Academy of Sciences of the United States of America 99(5):3047-3051, Mar. 5, 2002.
Turner et al., "Molecular Basis of Epithelial Barrier Regulation From Basic Mechanisms to Clinical Application," The American Journal of Pathology, 169(6): 1901-1909 (Dec. 2006).
Tyrrell, D. et al. "Structural requirements forthe carbohydrate ligand of E-selectin," PNAS, 88: 10372-10376 (Nov. 1991).
Ueda et. al., "Structure-Activity Relationships of Cyclic Peptide-Based Chemokine Receptor CXCR4 Antagonists: Disclosing the Importance of Side-Chain and Backbone Functionalities," J. Med. Chem. 50:192-198, 2007.
Van Der Velde et al., "Galectin-3 and sST2 in prediction of left ventricular ejection fraction after myocardial infarction," Clinica Chimica Acta, 452, 50-57, Jan. 2016.
Venkataraman et al., "Reawakening Retrocyclins: Ancestral Human Defensins Active Against HIV-1," Plos Biology, 7(4): 720-729 (Apr. 2009).
Wai, "Blockade of Chemokine (C-X-C motif) Receptor 4 for the Inhibition of Hepatocellular Carcinoma Metastasis," A Thesis, in partial fulfillment of requirements for Ph.D. Degree at the Univ. of Hong Kong, Jun. 2008.
Wakefield et al., "GMI-1271 and its Combination with LMWH Promotes Safer and More Effective Treatment of Venous Thrombosis: A Stage B Study," VITA presentation to NHLBI at National Institutes of Health, Feb. 2017.
Waldmann et al., "Synthesis of 2-Acetamindo-2-Deoxyglucosylasparagine Glyco-Tripeptide and-Pentapeptides by Selective C-and N-Terminal Elongation of the Peptide Chain," Carbohydrate Research 196: 75-93, 1990.
Walker et al., "Rapid Development of Glycan-Specific, Broad, and Potent Anti-HIV-1 gp120 Neutralizing Antibodies in an R5 SIV/HIV Chimeric Virus Infected Macaque," Proceedings of the National Academy of Sciences 108(50):20125-20129, Dec. 2011.
Walsh, "Novel Therapies for Asthma—Advances and Problems," Current Pharmaceutical Design, 11(23): 3027-3038 (2005).
Walz et al., "Recognition by ELAM-1 of the Sialyl-Le.sup.X Determinant on Myeloid and Tumor Cells," Science 250:1132-1135, 1990.
Wang et al., "Binding of High-Mannose-Type Oligosaccharides and Synthetic Oligomannose Clusters to Human Antibody 2G12: Implications for HIV-1 Vaccine Design," Chemistry & Biology 11:127-134, Jan. 2004.
Wang et al., "Effect of ginsenoside rg1 and rh1 on the expression of hla-dr, cd25, cd44, cd11c and e-selectin on dendritic cell," Zhongguo Mianyixue Zazhi, 23(1): 46-48 (2007)—Abstract.
Wang et al., "Targeting the Carbohydrates on HIV-1: Interaction of Oligomannose Dendrons with Human Monoclonal Antibody 2G12 and DC-SIGN," Proceedings of the National Academy of Sciences 105(10):3690-3695, Mar. 2008.

Wang et al., "Galectin-3 promotes HIV-1 budding via association with Alix and Gag p6," Glycobiology, 24(11), 1022-1035, 2014.
Ward et al., "Blocking of adhesion molecules in vivo as anti-inflammatory therapy," Immunology 1: 165-171, 1994.
Wesche et al., "Characterization of membrane translocation by anthrax protective antigen," Biochemistry, 37(45): 15737-15746 (Nov. 10, 1998).
Whisler et al., "Regulation of Lymphocyte Responses by Human Gangliosides. I. Characteristics of Inhibitory Effects and the Induction of Impaired Activation," Journal of Immunology 125(5):2106-2111, 1980.
Wicklein et al., "E-and P-Selectins Are Essential for Repopulation of Chronic Myelogenous and Chronic Eosinophilic Leukemias in a Scid Mouse Xenograft Model," PLOS One, 8(7), e70139, 2013.
Winkler et al., "Adhesion to E-selectin promotes growth inhibition and apoptosis of human and murine hematopoietic progenitor cells independent of PSGL-1," Blood, 103(5):1685-92, Mar. 1, 2004.
Winkler et al., "Absence of E-selectin at vascular niche delays hematopoietic stem cell turn-over," Blood, 110(11):188A, Nov. 2007.
Winkler et al., "Absence or blockage of E-Selectin-Mediated Cell Adhesion Delays Hematopoietic Stem Cell", ASH Annual Meeting 2009, Abstract #564, Nov. 2009.
Winkler et al., "Absence or blockage of E-Selectin-Mediated Cell Adhesion Delays Hematopoietic Stem Cell", Blood, 114(22), Abstract #564, Dec. 7, 2009.
Winkler et al., "Vascular niche E-selectin regulates hematopoietic stem cell dormancy, self renewal and chemoresistance," Nature Medicine, 18(11), 1651-1657, 2012.
Winkler et al., "Vascular niche E-selectin regulates hemopoietic stem cell dormancy, self-renewal and chemoresistance," Nature Medicine, 18(11), 1651-1657, Supplementary Figures and Table, 2012.
Winkler et al., "Administration of E-Selectin Antagonist GMI-1271 Improves Survival After High-Dose Chemotherapy By Alleviating Mucositis and Accelerating Neutrophil Recovery," Blood, 122(21), Abstract #2266, Nov. 15, 2013.
Winkler et al., "Mobilisation of Reconstituting HSC Is Boosted By Synergy Between G-CSF and E-Selectin Antagonist GMI-1271," Blood, 124(21), Abstract #317, Dec. 6, 2014.
Winkler et al., "Vascular Niche E-Selectin Protects Acute Myeloid Leukaemia Stem Cells from Chemotherapy,"Blood, 124(21), Abstract #620, Dec. 6, 2014.
Winkler, "Mobilisation of reconstituting HSC is boosted by E-selectin antagonist GMI-1271," Proceedings of the 56th Annual Meeting of the American Society of Hematology, Abstract #317, Oral Presentation on Dec. 7, 2014, San Francisco, CA.
Winkler, "Vascular bone marrow niches protect AML Leukaemia stem cells from chemotherapy," Proceedings of the 56th Annual Meeting of the American Society of Hematology, Abstract#620, Oral Presentation on Dec. 8, 2014, San Francisco, CA.
Winkler et al., "Mobilization of CD8+Central Memory T-Cells with Enhanced Reconstitution Potential in Mice By a Combination of G-CSF and GMI-1271-Mediated E-Selectin Blockade,"Blood, 126(23), Abstract#512, Dec. 3, 2015.
Winkler et al., "Vascular E-Selectin Protects leukemia Cells from Chemotherapy By Directly Activating Pro-Survival NF-Kb Signalling—Therapeutic Blockade of E-Selectin Dampens NF-Kb Activation," Blood, 128(22), Abstract #2823, Dec. 2, 2016.
Winkler et al., "Vascular E-Selectin Mediates Chemo-Resistance in Acute Myeloid Leukemia Initiating Cells Via Canonical Receptors PSGL-1 (CD1 62) and Hcell (CD44) and AKT Signalling," Proceedings of the 59th American Society of hematology Annual Meeting, Oral Presentation, Dec. 11, 2017, Atlanta, GA.
Winkler et al., "Vascular E-Selectin Acts As a Gatekeeper Inducing Commitment and Loss of Self-Renewal in HSC Transmigrating through the Marrow Vasculature," Blood, 132(Supplement 1), Abstract #4552, Nov. 2018.
Winkler et al., "Vascular E-Selectin—A Gatekeeper Inducing Commitment and Loss of Self-Renewal in transmigrating HSC," Poster #4552, Proceedings of the 60th American Society of Hematology Annual Meeting, Dec. 3, 2018, San Diego, CA.

(56) References Cited

OTHER PUBLICATIONS

Winnard, P. et al., "Real time non-invasive imaging of receptor-ligand interactions in vivo," J. Cell. Biochem., 90: 454-463 (2003).
Winzer, K. et al. "The Pseudomonas aeruginosa Lectins PA-IL and PA-IIL are Controlled by Quorom Sensing and by RpoS," J. Bacteriol. 182(22): 6401-6411 (2000).
Witz, "The involvement of selectins and their ligands in tumor-progression," Immunol. Lett., 104(1-2): 89-93 (2006).
Wu et al., "Salivary Agglutinin Inhibits HIV Type 1 Infectivity through Interaction with Viral Glycoprotein 120," AIDS Research and Human Retroviruses, 19(30), 201-209, 2003.
Wu, B. et al. "Structures of the CXCR4 Chemokine GPCR with Small-Molecule and Cyclic Peptide Antagonists," Science, 330(6007): 1066-1071 (Nov. 2010).
Wun et al., "Pan-Selectin Antagonist Rivipansel (GMI-1070) Reduces Soluble E-Selectin Levels While Improving Clinical Outcomes in SCD Vaso-Occlusive Crisis" Blood, 124(21):2704, Dec. 6, 2014.
Xu, J. et al., "Molecular insights and therapeutic targets for diabetic endothelial dysfunction," Circulation, 120: 1266-1286 (2009).
Yadav et al., "Screening of Neu5Acα(2-6)gal isomer preferences of siglecs with a sialic acid microarray," Org. Biomol. Chem., 2016, 14, 10812-10815.
Yamazaki, F. et al,. "Synthesis of an appropriately protected core glycotetraoside, a key intermediate for the synthesis of 'bisected' complex-type glycans of a glycoprotein," Carbohydrate Research 201: 15-30, 1990.
Zeisig et al., "Effect of sialyl Lewis X-glycoliposomes on the inhibition of E-selectin-mediated tumour cell adhesion in vitro" Biochimica et Biophysica Acta (2004) 1660, pp. 31-40.
Zhan et al., "Discovery of Small Molecule CXCR4 Antagonists," J. Med. Chem. 50:5655-5664, 2007.
Zhang et al., "Chemokine CXCL 12 and its receptor CXCR4 expression are associated with perineural invasion of prostate cancer" Journal of Experimental and Clinical Cancer Research (2008) vol. 27 No. 62, pp. 1-9.
Zhang, Z. et al. "CXCR4 but not CXCR7 is mainly implicated in ocular leukocyte trafficking during ovalbumin-induced acute uveitis," Experimental Eye Research, 89: 522-531 (2009).
Zhang et al., "The Dual E-Selectin/CXCR4 Inhibitor, GMI-1359, Enhances Efficacy of Anti-Leukemia Chemotherapy in FLT3-ITD Mutated Acute Myeloid Leukemia," Blood, 126(23), Abstract#3790, Dec. 3, 2015.
Zhang et al., "The Dual E-selectin/CXCR4 Inhibitor, GMI-1359, Enhances Efficacy of Chemotherapy in FLT3-ITD-Mutated Acute Myeloid Leukemia," Proceedings of the 57th Annual Meeting of the American Society of Hematology, Abstract #3790, Poster Presentation, Dec. 7, 2015, Orlando, FL.
Zhang et al., "The E-selectin/CXCR4 Inhibitor GMI-1359 Effectively Mobilizes Bone Marrow Leukemia Cells and Enhances FLT3 Inhibitor Efficacy in a Murine AML Model," Proceedings of the 107th Annual Meeting of AACR, 3284, Apr. 16-20, 2016, New Orleans, LA.
Zhang et al., "Abstract 3284: Targeting E-selectin/CXCR4 with GMI-1359 effectively mobilizes bone marrow leukemia cells and enhances FLT3 inhibitor-induced anti-leukemia efficacy in a murine acute myeloid leukemia model," Cancer Research, 76(14 Supplement), 3284-3284, Jul. 22, 2016.
Zhang et al., "Dual E-Selectin/CXCR4 Antagonist GMI-1359 Exerts Efficient Anti-Leukemia Effects in a FLT3 Itd Mutated Acute Myeloid Leukemia Patient-Derived Xenograft Murine Model," Blood, 128(22), Abstract #3519, Dec. 2, 2016.
Zhang et al., "The Dual E-selectin/CXCR4 Antagonist GMI-1359 Exerts Antileukemia Efficacy Against FLT3-ITD-mutated Acute Myeloid leukemia in A Patient-derived Xenograft Murine Model," Proceedings of the 58th Annual Meeting of the American Scoeity of Hematology, Abstract #3519, Poster Presentation, Dec. 4, 2016, San Diego, CA.
Zhao T. et al. "Targeting human CD34+ hematopoietic stem cells with anti-CD45 x antimyosin light-chain bispecific antibody preserves cardiac function in myocardial infarction" Journal of Applied Physiology, 10(6):1793-1800 (2008).
Zheng, CX et al. "The prognostic value of preoperative serum levels of CEA, CA19-9 and CA72-4 in patients with colorectal cancer," World J. Gastroentero, 7(3): 431-434 (2001).
Zhou et al., "The Selectin GMP-140 Binds to Sialylated, Fucosylated Lactosaminoglycans on Both Myeloid and Nonmyeloid Cells," Journal of Cell Biology 115(2):557-564, 1991.
Zhou, G. et al. "Effect of ET-RA on expression of selectin on the surface of endothelial cell in mice with severe acute pancreatitis," Chongqing Yixue, 35(7): 624-626 (2006)—Abstract.
Zopf et al., "Affinity Purification of Antibodies Using Oligosaccharide-Phenethylamine Derivatives Coupled to Sepharose," Meth. Enzymol. 50:171-175, 1978.
Zuber et al., "Mouse models of human AML accurately predict chemotherapy response," Genes. Dev., 23 (7): 877-889 (2009).

\* cited by examiner

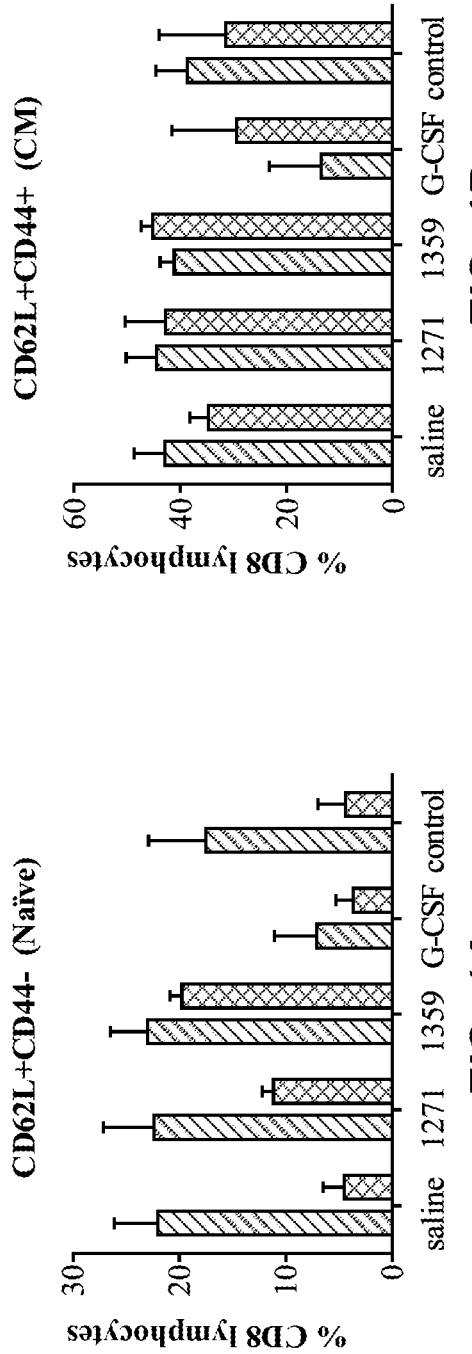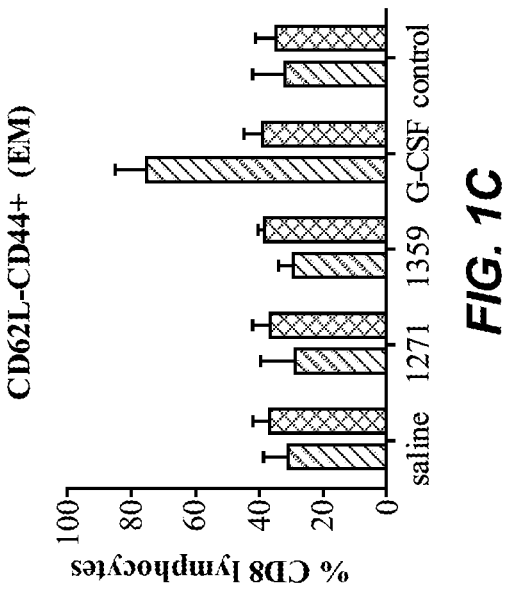

METHODS OF MOBILIZING MARROW INFILTRATING LYMPHOCYTES AND USES THEREOF

This application claims the benefit under 35 U.S.C. § 119(e) to U.S. Provisional Application No. 62/592,686, filed Nov. 30, 2017, which is incorporated by reference herein in its entirety.

The present disclosure relates to methods for mobilizing tumor-specific, primed, marrow infiltrating lymphocytes (MILs) from the bone marrow using at least one E-selectin antagonist or compositions comprising the same as well as methods of treatment or prevention of cancers using the mobilized MILs.

Immunotherapy has become a major focus of research in oncology. For example, for many years, Adoptive T-cell Therapy (ACT) has been used as a treatment for various cancers. ACT involves the isolation and ex vivo expansion of tumor specific T-cells to achieve greater number of T-cells than what could be obtained by vaccination alone. The tumor specific T-cells are then infused into patients with cancer in an attempt to give their immune system the ability to overwhelm remaining tumor via T-cells which can attack and kill cancer. Therefore, efficacious ACT requires the ability to activate tumor-specific T-cells that have the ability to travel to the tumor site and effectively kill their target. See, e.g., Noonan et al., *Adoptive Transfer of Activated Marrow-Infiltrating Lymphocytes Induces Measureable Antitumor Immunity in the Bone Marrow in Multiple Myeloma*, Cancer, Vol. 7, Issue 288 (May 15, 2015).

Prominent in oncology research is the tumor microenvironment and the interaction of T-cells. T-cells that are able to effectively identify and/or attack cancer cells are of particular interest because, for example, they can allow the body to quickly mount a response to cancer. T-cells that have long life spans are also of particular interest because, for example, they will be able to provide the body with longer-lasting defenses. One promising type of T-cell are MILs. MILs are T-cells that have been primed to tumor antigens. MILs have been found in patients suffering from hematological malignancies and in metastatic disease arising from solid tumors such as prostate, breast, and lung cancers. The presence of tumor-specific T-cells in the bone marrow of patients with hematologic malignancies and solid tumors opens up the prospect of utilizing MILs for many therapies including adoptive T-cell therapy (ACT).

A study by Noonan et al. has previously shown that anti-CD3/anti-CD28 ex vivo activated MILs have several fundamental properties, making them good candidates for cancer treatments. Noonan et al. at 2. Noonan found that, upon activation, MILs demonstrate significant tumor specificity compared to peripheral blood lymphocytes, target a broad range of antigens present on both the mature multiple myeloma plasma cells and their clonogenic precursors, and effectively kill multiple myeloma plasma cells. Id. Therefore, MILs exemplify a promising tumor-specific approach for treating cancers and cancerous malignancies.

Accordingly, there is an unmet need for methods of mobilizing MILs and inducing them to leave the marrow, where they can, for example, be used in ex vivo manipulations such as the development of CAR T-cells or used in autologous or allogenic donation.

Additionally, although ACT provides one option for cancer treatments, it requires ex vivo expansion of the cells, which can be time-consuming, inconvenient to patients, and labor intensive.

Accordingly, there is an unmet need for methods of mobilizing MILs for in vivo treatments.

BRIEF DESCRIPTION OF DRAWINGS

FIG. 1A is an exemplary graph of the percentage of CD8+ lymphocytes in the population of CD62L+CD44− (naïve) lymphocytes found in bone marrow and peripheral blood samples taken from CT26 non-immune mice acting as controls and in CT26 immune mice following administration of GMI-1271, GMI-1359, granulocyte-colony stimulating factor (G-CSF), or saline.

FIG. 1B is an exemplary graph of the percentage of CD8+ lymphocytes in the population of CD62L+CD44+(central memory or CM) lymphocytes found in bone marrow and peripheral blood samples taken from CT26 non-immune mice acting as controls and in CT26 immune mice following administration of GMI-1271, GMI-1359, G-CSF, or saline.

FIG. 1C is an exemplary graph of the percentage of CD8+ lymphocytes in the population of CD62L-CD44+(effector memory or EM) lymphocytes found in bone marrow and peripheral blood samples taken from CT26 non-immune mice acting as controls and in CT26 immune mice following administration of GMI-1271, GMI-1359, G-CSF, or saline.

Figure 2:
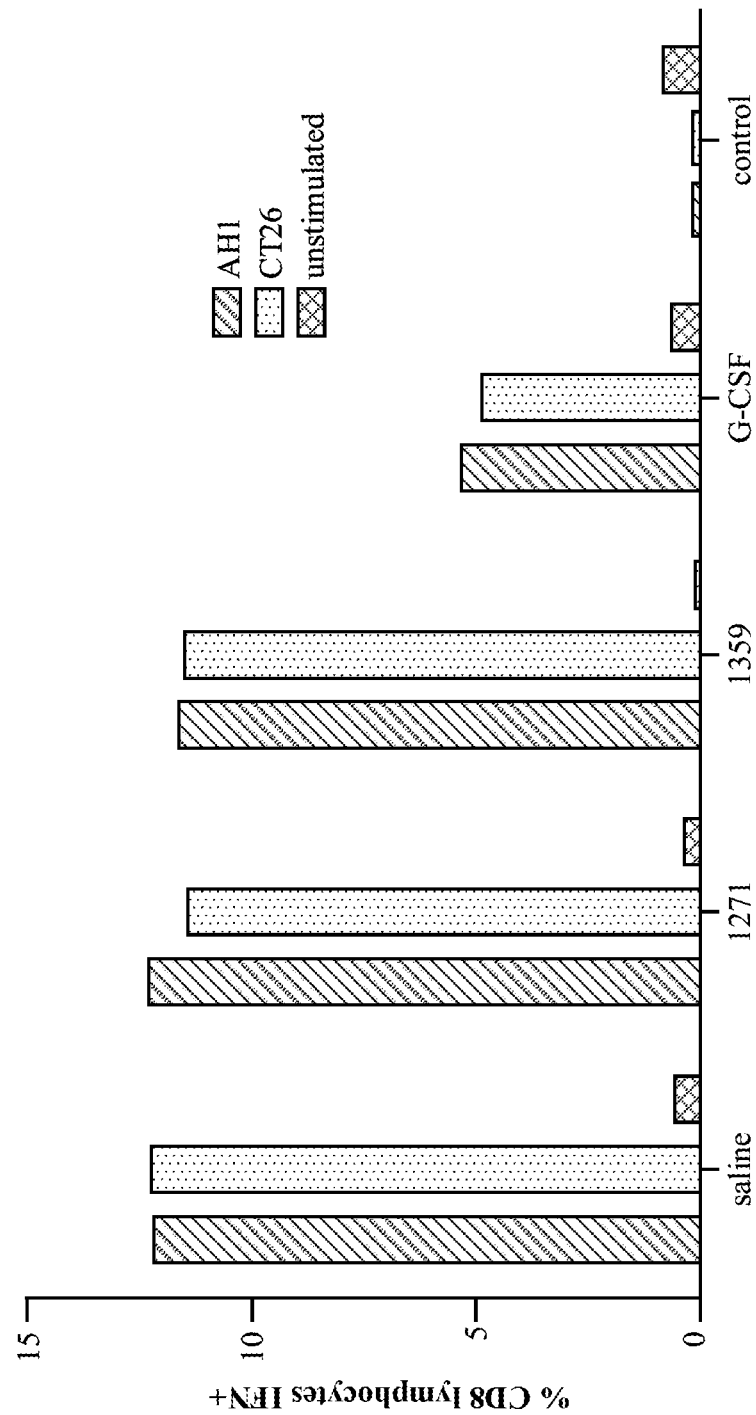
FIG. 2 is an exemplary graph of the percentage of IFN+ lymphocytes in the population of CD8+ lymphocytes from bone marrow samples taken from CT26 non-immune mice acting as controls and in CT26 immune mice following administration of GMI-1271, GMI-1359, G-CSF, or saline.

The terms defined below are more fully defined by reference to the specification as a whole. While the terms used herein are believed to be well understood by one of ordinary skill in the art, the definitions included in this document are set forth to facilitate explanation of the presently-disclosed subject matter.

Following long-standing patent law convention, the terms "a," "an," and "the" refer to "one or more" when used in this application, including the claims. Thus, for example, reference to "a cell" includes one cell or a plurality of cells, and so forth.

Throughout this disclosure, various embodiments can be presented in a range format. Numeric ranges are inclusive of the numbers defining the range. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range, such as from 1 to 6, should be considered to have specifically disclosed subranges, such as from 1 to 3, from 1 to 4, from 1 to 5, from 2 to 4, from 2 to 6, from 3 to 6 etc., as well as individual numbers within that range, for example, 1, 2, 2.7, 3.8, 4, 5.1, 5.3, and 6. This applies regardless of the breadth of the range.

E-selectin (CD62E) is a cell adhesion molecule that is expressed on activated endothelial cells and plays an important role in leukocyte recruitment to the site of injury. The terms "E-selectin antagonist" means an agent that inhibits an activity of E-selectin or inhibits the binding of E-selectin to one or more E-selectin ligands (which in turn may inhibit a biological activity of E-selectin). The term "E-selectin antagonist" includes antagonists of E-selectin only, as well as antagonists of E-selectin and either P-selectin or L-selectin, and antagonists of E-selectin, P-selectin, and L-selectin. E-selectin antagonists include the glycomimetic compounds described herein that inhibit interaction of E-selectin with sialyl Le$^a$ (sLe$^a$) or sialyl Le$^x$ (sLe$^x$). E-selectin antagonists also include antibodies, polypeptides, peptides, peptidomimetics, and aptamers which bind at or near the binding site on E-selectin to inhibit E-selectin interaction with sialyl Le$^a$ (sLe$^a$) or sialyl Le$^x$ (sLe$^x$)).

The term "non-glycomimetic moiety" includes moieties having a structure not intended to mimic a carbohydrate molecule. A non-glycomimetic moiety may not be (and is typically not) active as an E-selectin antagonist. Instead, non-glycomimetic moieties are generally moieties added to a glycomimetic moiety for purposes of altering at least one property, such as solubility, bio-availability, lipophilicity and/or other drug-like properties of the glycomimetic.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "therapy" refers to "treating" or "treatment" of a disease or condition including inhibiting the disease (slowing or arresting its development), providing relief from the symptoms or side-effects of the disease (including palliative treatment), and relieving the disease (causing regression of the disease). "Therapy" may also refer to prophylactic treatment, which includes preventing or delaying the onset of the disease or condition from occurring in a subject that may be predisposed to the disease but does not yet experience or exhibit symptoms of the disease.

The term "treatment" means the slowing down, interruption, arrest, reversal, or stoppage of the progression of the disease, which does not necessarily require the complete elimination of all the signs and symptoms of the disease. "Treatment" also includes prophylactic treatment to prevent or delay the onset of the disease or condition from occurring in a subject that may be predisposed to the disease but does not yet experience or exhibit symptoms of the disease. "Treatment" further means preventing or delaying the relapse or recurrence of the disease or condition in a subject that is considered in remission for the disease or condition. Furthermore, it is not necessary for the treatment to show effectiveness in 100% of the patients treated, rather, the term "treatment" is intended to mean that a statistically significant proportion of patients can be treated effectively, in such a way that the symptoms and clinical signs show at least an improvement. The person skilled in the art can easily establish whether the proportion is statistically significant using various statistical methods (e.g. confidence intervals, determination of them p value, Student's t-test, Mann-Whitney test etc.). Confidence intervals have a confidence of at least 90%, at least 95%, at least 97%, at least 98% or at least 99%. The p values are 0.1, 0.05, 0.01, 0.005 or 0.0001.

The term "prevention of relapse" refers to the reduction of the risk of the return of a disease or condition and/or extending the time until a relapse occurs.

As used herein, "together" is used to mean that the agents are administered concurrently. They can be administered in the same composition or in separate compositions. In contrast to "together," "sequentially" is used herein to mean that the gap between administering one agent and the other is significant, i.e., the first administered agent may no longer be present in the bloodstream in a therapeutic amount when the second agent and/or third agent is administered. When administered sequentially, the compounds may be administered in any order.

Briefly, provided herein are agents that are E-selectin antagonists, compositions comprising the agents, and methods for using the agents for mobilizing marrow infiltrating lymphocytes from the bone marrow. Glycomimetic compounds that may be used in these methods are E-selectin antagonists as described herein. Additionally, compounds disclosed herein may be heterobifunctional, for example, an E-selectin antagonist linked to a CXCR4 chemokine receptor antagonist.

E-selectin is an adhesion molecule expressed on endothelial cells and binds to specific carbohydrate sequences (sialyl Le$^x$ and sialyl Le$^a$) found on the surfaces of opposing bound cells. The endothelium in most of the normal vasculature does not express E-selectin until stimulation of protein synthesis by inflammatory mediators. After about three hours of de novo protein synthesis, E-selectin is then expressed as a result of an inflammatory response. In contrast, E-selectin is constitutively expressed in the bone marrow by the endothelial cells lining the blood vessels. Here, it is thought, without wishing to be bound by theory, that MILs reside in the vasculature niche of the bone marrow by binding to adhesion molecules, including E-selectin. In this disclosure, antagonists of E-selectin are provided that mobilize MILs from the bone marrow. Such antagonists may include but are not limited to small molecules, antibodies, aptamers, peptides, and glycoproteins. MILs derived from mobilized cells from the bone marrow have a wide range of therapeutic uses. For example, MILs can be induced to leave the marrow and distribute to the periphery where they may act in vivo or where they can be collected for ex vivo manipulation such as engineering CAR T-cells.

Furthermore, it is known that some individuals do not respond well to the use of Plerixafor (AMD-3100) and/or G-CSF due to age, disease, and certain genetic conditions. Thus, to the extent those prior art methods are found to be ineffective in mobilizing MILs, the disclosed methods provide an alternative.

In some embodiments, a method is provided for mobilizing MILs by inhibiting E-selectin, a major adhesion protein in the bone marrow vasculature. This method may comprise using the at least one E-selectin antagonist alone or in combination with other agents used to mobilize hematopoietic stem cells. Specific small molecule antagonists of E-selectin that mobilize hematopoietic cells and which are therefore useful for these methods and other methods are described herein.

In some embodiments, at least one E-selectin antagonist is administered to a patient. In some embodiments, at least one E-selectin antagonist is administered to a cancer patient in remission. In some embodiments, at least one E-selectin antagonist is administered as a cancer vaccine to stimulate MILs in a cancer patient or cancer survivor to prevent relapse.

In some embodiments, a method of treating cancer and/or preventing a cancer relapse is provided comprising administering to a patient at least one E-selectin antagonist in an amount sufficient to mobilize MILs of the patient into the peripheral blood.

In some embodiments, a method of treating cancer and/or preventing a cancer relapse is provided comprising administering to a donor patient at least one E-selectin antagonist in an amount of sufficient to mobilize MILs of the patient out of the marrow (e.g., into the peripheral blood), recovering MILS (e.g., recovering them from the peripheral blood), and transplanting at least a portion of the MIL cell population to the donor patient or another patient. In some embodiments, the MIL cell population is expanded ex vivo before transplantation.

In some embodiments, a method of preventing cancer is provided comprising administering to a donor patient at least one E-selectin antagonist in an amount sufficient to mobilize MILs of the patient out of the bone marrow (e.g., into the peripheral blood), recovering MILs (e.g., recovering them from the peripheral blood), and transplanting at least a portion of MIL cell population to a subject (e.g., a non-cancer patient, a patient suffering from a different form or type of cancer than the donor patient, etc.). In some embodiments, the MIL cell population is expanded ex vivo before transplantation.

In some embodiments, the at least one E-selectin antagonist is in the form of a pharmaceutical composition. In some embodiments the pharmaceutical composition further comprises at least one pharmaceutically acceptable ingredient.

At least one E-selectin antagonist may be chosen from glycomimetics. In some embodiments, at least one E-selectin antagonist is chosen from sialyl Lewis$^x$ (sLe$^x$) and sLe$^x$ mimetics. In some embodiments, at least one E-selectin antagonist is chosen from glycomimetic antagonists of E-selectin, antibodies directed to E-selectin, aptamers to E-selectin, peptides or polypeptides directed to E-selectin, and peptidomimetics directed to E-selectin.

In some embodiments, a colony stimulating factor is administered with at least one E-selectin antagonist to the cancer patient.

In some embodiments, the cancer patient has received or will receive chemotherapy and/or radiotherapy. In some embodiments, the chemotherapy comprises administration of bortexomib and/or gemcitabine. In some embodiments, the cancer is a hematologic cancer. In some embodiments, the cancer is a solid cancer. In some embodiments, the cancer is a liquid cancer.

In some embodiments, the patient has been diagnosed with a first type of cancer and the cancer for which the method is performed to treat or prevent is a second type of cancer.

In some embodiments, a composition comprising MILs mobilized out of the bone marrow by at least one E-selectin antagonist is disclosed.

In some embodiments, treatment of cancer is provided by the mobilization of MILs following the administration of at least one E-selectin antagonist (i.e., in vivo mobilization of MILs). In some embodiments, relapse of cancer is prevented by the mobilization of MILs following the administration of at least one E-selectin antagonist.

In some embodiments, at least one E-selectin antagonist is chosen from compounds of Formula (I):

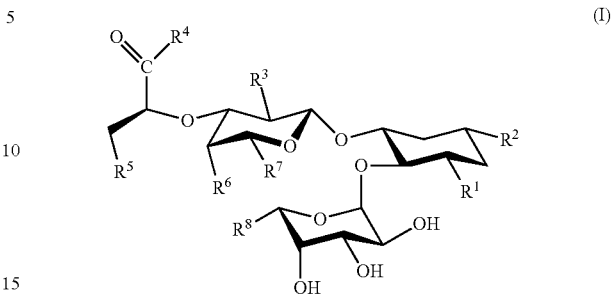

isomers of Formula (I), tautomers of Formula (I), and pharmaceutically acceptable salts of any of the foregoing, wherein:

$R^1$ is chosen from $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, and $C_2$-$C_8$ haloalkynyl groups;

$R^2$ is chosen from H, -M, and -L-M;

$R^3$ is chosen from —OH, —NH$_2$, —OC(=O)Y$^1$, —NHC(=O)Y$^1$, and —NHC(=O)NHY$^1$ groups, wherein Y$^1$ is chosen from $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, $C_2$-$C_8$ haloalkynyl, $C_6$-$C_{18}$ aryl, and $C_1$-$C_{13}$ heteroaryl groups;

$R^4$ is chosen from —OH and —NZ$^1$Z$^2$ groups, wherein Z$^1$ and Z$^2$, which may be identical or different, are each independently chosen from H, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, and $C_2$-$C_8$ haloalkynyl groups, wherein Z$^1$ and Z$^2$ may together form a ring;

$R^5$ is chosen from $C_3$-$C_8$ cycloalkyl groups;

$R^6$ is chosen from —OH, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, and $C_2$-$C_8$ haloalkynyl groups;

$R^7$ is chosen from —CH$_2$OH, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, and $C_2$-$C_8$ haloalkynyl groups;

$R^8$ is chosen from $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, and $C_2$-$C_8$ haloalkynyl groups;

L is chosen from linker groups; and

M is a non-glycomimetic moiety chosen from —C(=O)NH(CH$_2$)$_{1-4}$NH$_2$, $C_1$-$C_8$ alkyl, —C(=O)OY$^2$, and moieties comprising polyethylene glycol, thiazolyl, or chromenyl, wherein Y$^2$ is chosen from $C_1$-$C_4$ alkyl, $C_2$-$C_4$ alkenyl, and $C_2$-$C_4$ alkynyl groups.

In some embodiments, at least one E-selectin antagonist is chosen from compounds of Formula (I), wherein M is a non-glycomimetic moiety comprising polyethylene glycol, thiazolyl, or chromenyl. In some embodiments, at least one E-selectin antagonist is chosen from compounds of Formula (I), wherein M is a non-glycomimetic moiety comprising polyethylene glycol.

As would be recognized by one of ordinary skill in the art, the phrase "isomers of Formula (I), tautomers of Formula (I), and pharmaceutically acceptable salts of any of the foregoing" includes hydrates and solvates.

In some embodiments, at least one E-selectin antagonist is chosen from compounds of Formula (I), wherein the non-glycomimetic moiety comprises polyethylene glycol.

In some embodiments, at least one E-selectin antagonist is chosen from compounds of Formula (II):

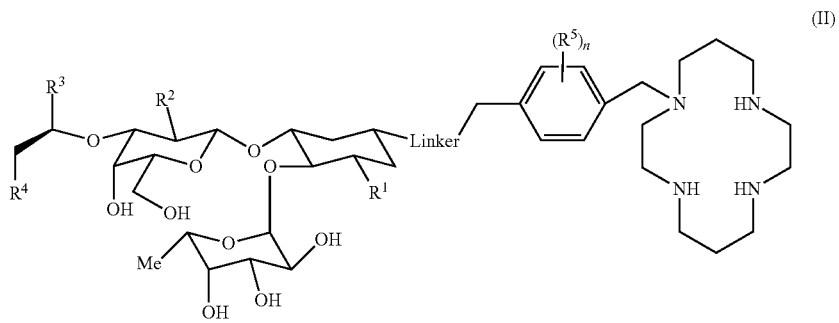

isomers of Formula (II), tautomers of Formula (II), and pharmaceutically acceptable salts of any of the foregoing, wherein:

$R^1$ is chosen from H, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, and $C_2$-$C_8$ haloalkynyl groups;

$R^2$ is chosen from —OH, —NH$_2$, —OC(=O)Y$^1$, —NHC(=O)Y$^1$, and —NHC(=O)NHY$^1$ groups, wherein Y$^1$ is chosen from $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, $C_2$-$C_8$ haloalkynyl, $C_6$-$C_{18}$ aryl, and $C_1$-$C_{13}$ heteroaryl groups;

$R^3$ is chosen from —CN, —CH$_2$CN, and —C(=O)Y$^2$ groups, wherein Y$^2$ is chosen from $C_1$-$C_8$ alkyl, $C_2$-$C_8$ alkenyl, $C_2$-$C_8$ alkynyl, —OZ$^1$, —NHOH, —NHOCH$_3$, —NHCN, and —NZ$^1$Z$^2$ groups, wherein Z$^1$ and Z$^2$, which may be identical or different, are independently chosen from H, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, and $C_2$-$C_8$ haloalkynyl groups, wherein Z$^1$ and Z$^2$ may together form a ring;

$R^4$ is chosen from $C_3$-$C_8$ cycloalkyl groups;

$R^5$ is independently chosen from H, halo, $C_1$-$C_8$ alkyl, $C_2$-$C_8$ alkenyl, $C_2$-$C_8$ alkynyl, $C_1$-$C_8$ haloalkyl, $C_2$-$C_8$ haloalkenyl, and $C_2$-$C_8$ haloalkynyl groups;

n is chosen from integers ranging from 1 to 4; and

L is chosen from linker groups.

As would be recognized by one of ordinary skill in the art, the phrase "isomers of Formula (II), tautomers of Formula (II), and pharmaceutically acceptable salts of any of the foregoing" includes hydrates and solvates.

In some embodiments, at least one E-selectin antagonist is chosen from compounds of Formula (IIa):

In some embodiments, the linker groups of Formula I and/or Formula II are independently chosen from groups comprising spacer groups, such spacer groups as, for example, —(CH$_2$)$_p$— and —O(CH$_2$)$_p$—, wherein p is chosen from integers ranging from 1 to 30. In some embodiments, p is chosen from integers ranging from 1 to 20. Other non-limiting examples of spacer groups include carbonyl groups and carbonyl-containing groups such as, for example, amide groups. A non-limiting example of a spacer group is

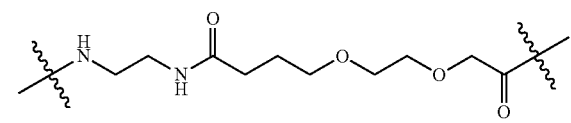

In some embodiments, the linker groups are independently chosen from

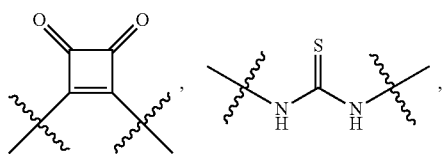

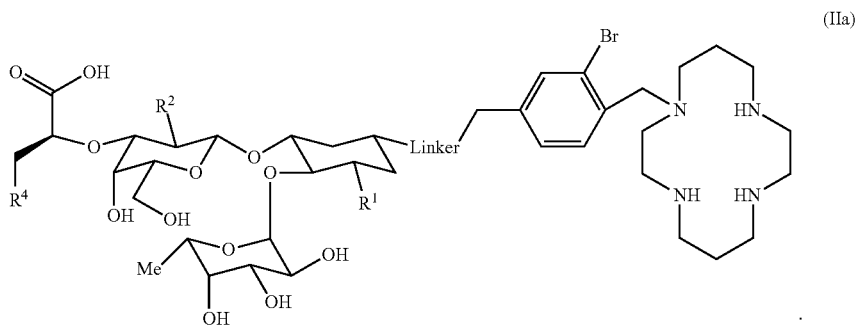

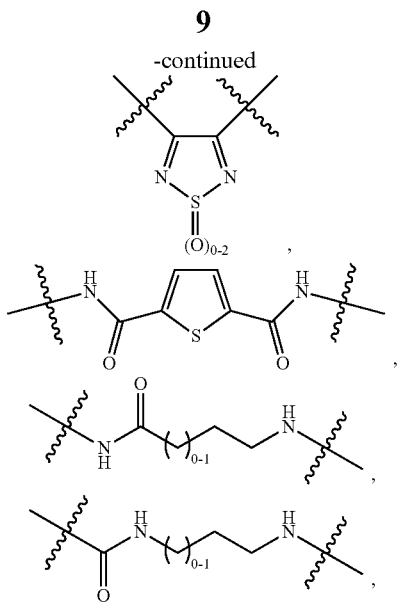

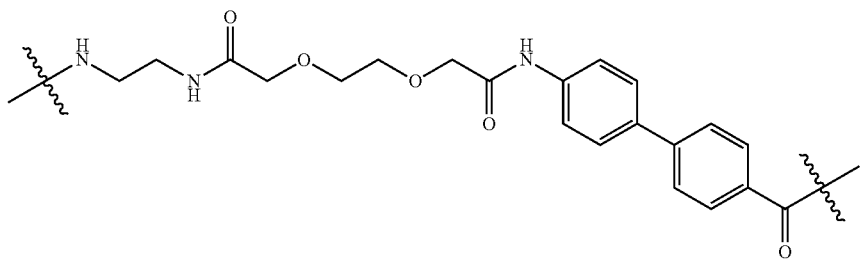

Other linker groups, such as, for example, polyethylene glycols (PEGs) and —C(═O)—NH—(CH$_2$)$_p$—C(═O)—NH—, wherein p is chosen from integers ranging from 1 to 30, or wherein p is chosen from integers ranging from 1 to 20, will be familiar to those of ordinary skill in the art and/or those in possession of the present disclosure.

In some embodiments, at least one linker group is

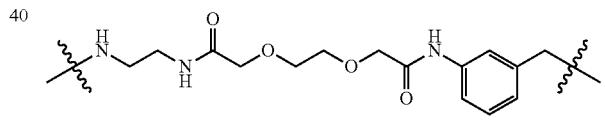

In some embodiments, at least one linker group is

In some embodiments, at least one linker group is chosen from —C(═O)NH(CH$_2$)$_2$NH—, —CH$_2$NHCH$_2$—, and —C(═O)NHCH$_2$—. In some embodiments, at least one linker group is —C(═O)NH(CH$_2$)$_2$NH—.

In some embodiments, at least one E-selectin antagonist is chosen from compounds of Formula (Ia):

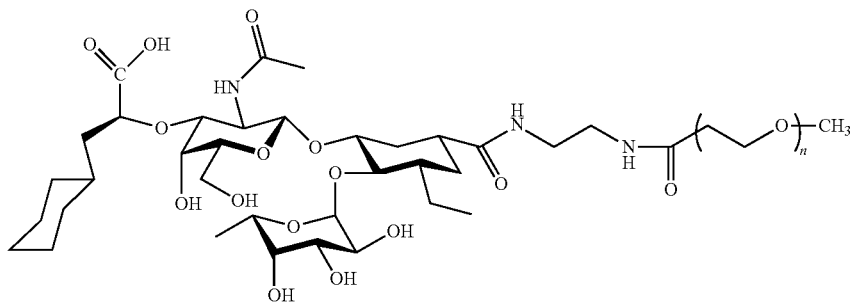

(Ia)

wherein n is chosen from integers ranging from 1 to 100. In some embodiments, n is chosen from 4, 8, 12, 16, 20, 24, and 28.

In some embodiments, at least one E-selectin antagonist is chosen from E-selectin antagonists disclosed in U.S. Pat. No. 9,109,002, which is hereby incorporated by reference. In some embodiments, at least one E-selectin antagonist is GMI-1271. See, e.g., Price et al., "Dormant breast cancer micrometastases reside in specific bone marrow niches that regulate their transit to and from bone," Science Translational Medicine, Vol. 8(340), May 25, 2016, [DOI:10.1126/scitranslmed.aad4059]; Dutta et al., "E-Selectin Inhibition Mitigates Splenic HSC Activation and Myelopoiesis in Hypercholesterolemic Mice With Myocardial Infarction", Arterioscler Thromb Vasc Biol [DOI: 10.1161/ATVBAHA.116.307519]

In some embodiments, at least one E-selectin antagonist is chosen from compounds of the following Formulae:

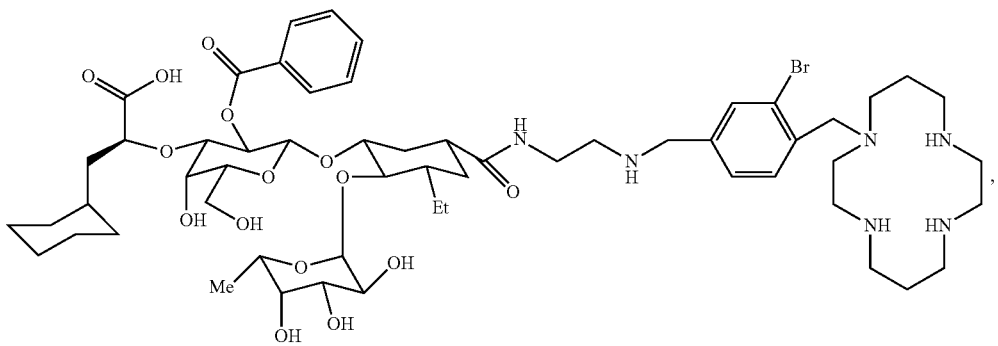

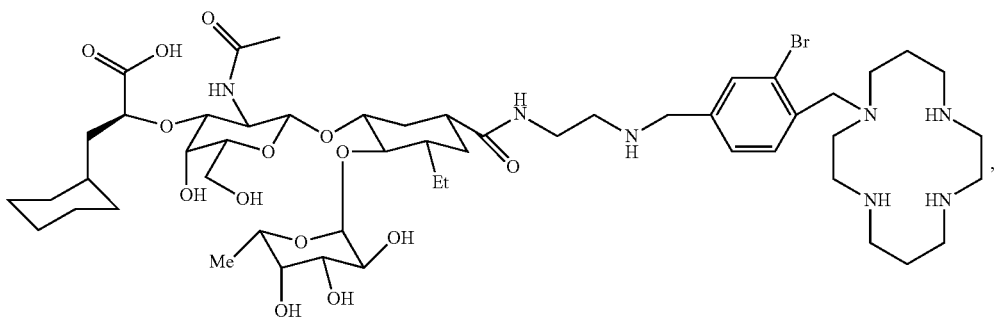

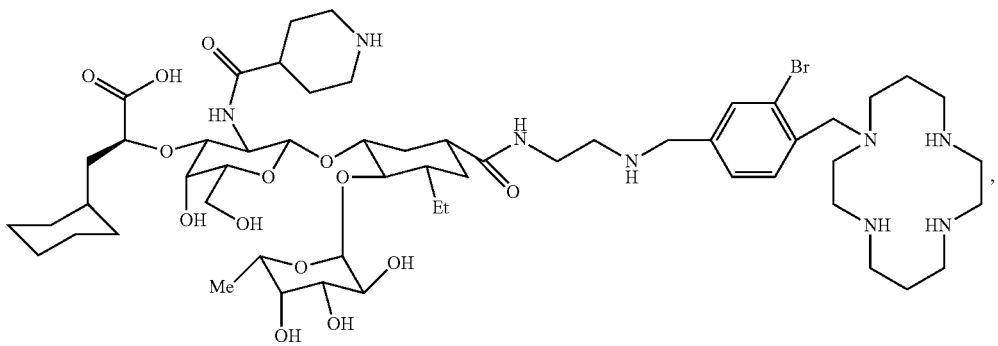

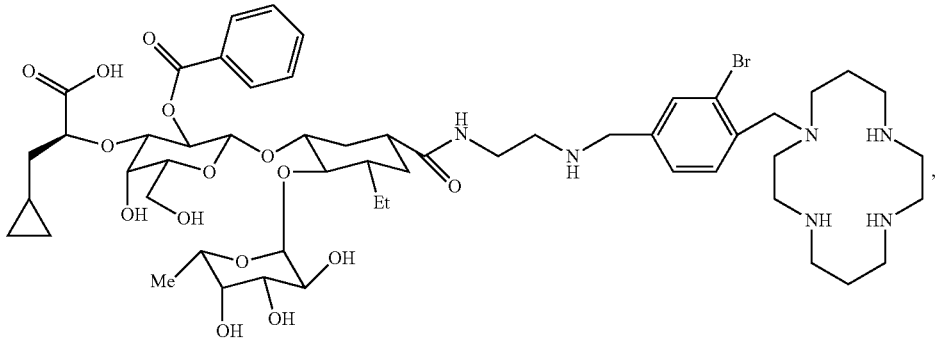

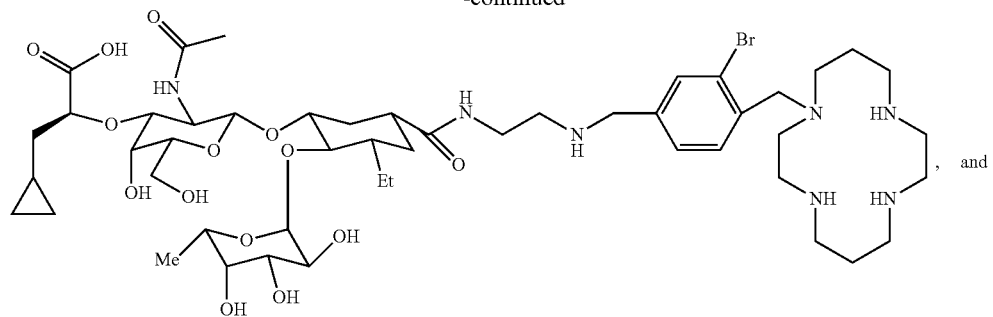
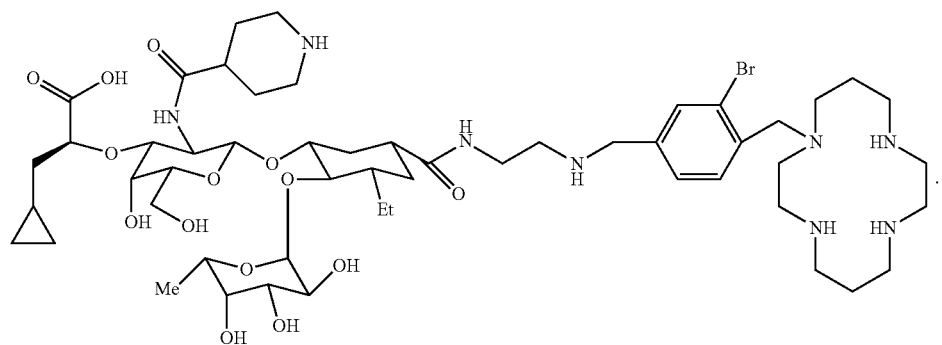
In some embodiments, at least one E-selectin antagonist is chosen from compounds of the following Formulae:
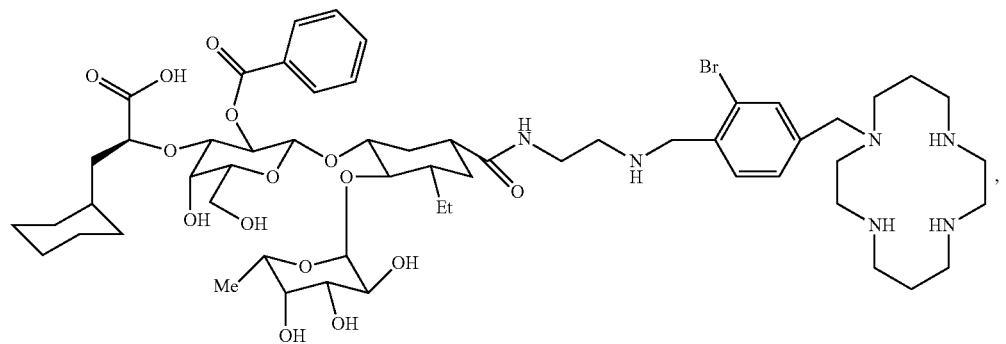
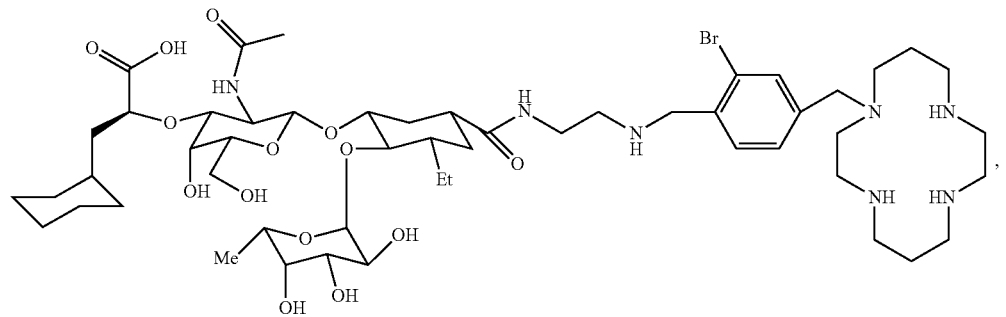

-continued

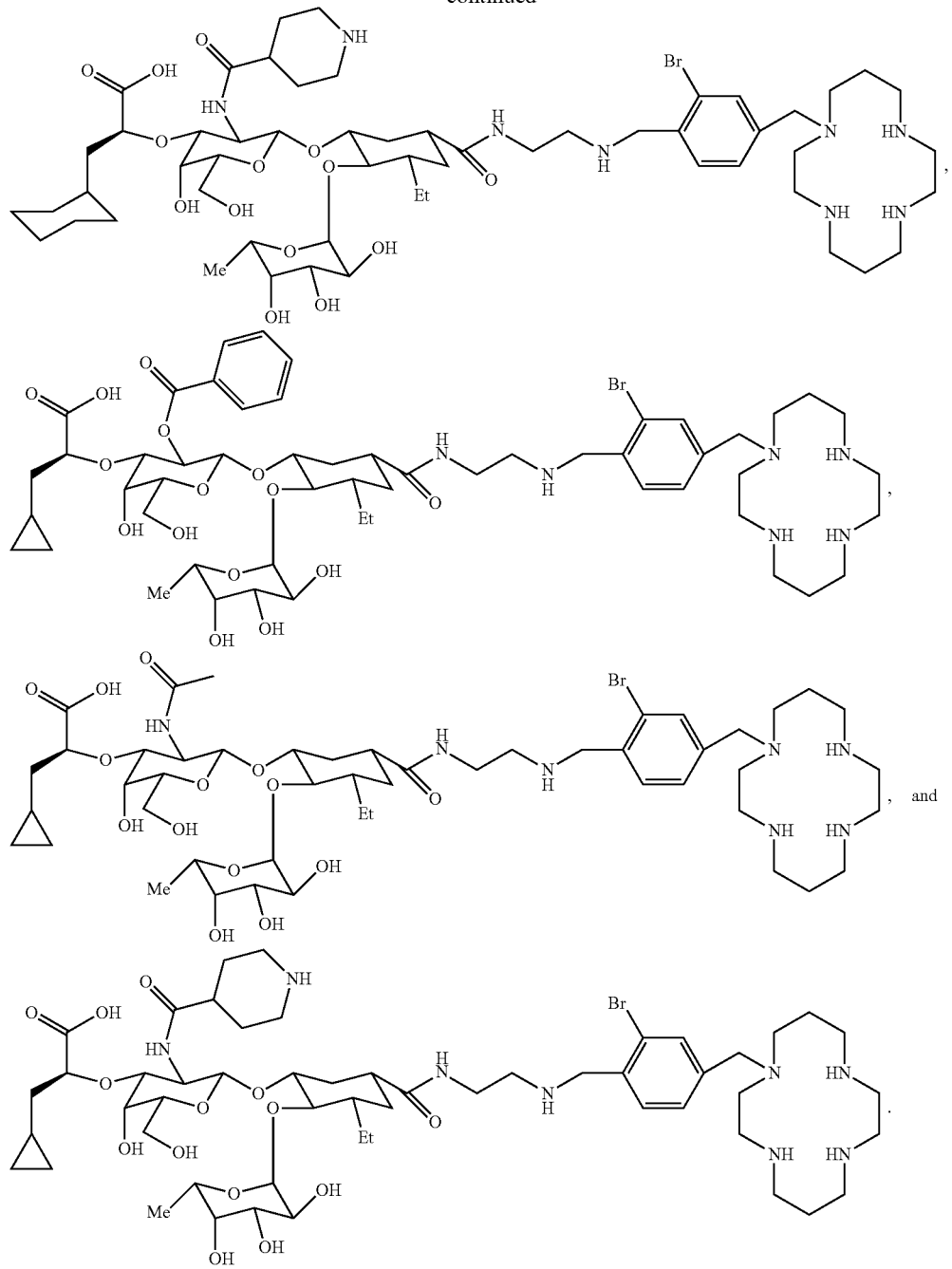

In some embodiments, at least one E-selectin antagonist is chosen from E-selectin antagonists disclosed in U.S. Pat. No. 8,410,066 and PCT/US2015/063191, which are hereby incorporated by reference. In some embodiments, at least one E-selectin antagonist is GMI-1359. See, e.g., Steele, Maria M. et al., "A small molecule glycomimetic antagonist of E-selectin and CXCR4 (GM1-1359) prevents pancreatic tumor metastasis and improves chemotherapy [abstract]," Proceedings of the 106th Annual Meeting of the American Association for Cancer Research, 2015 Apr. 18-22, Philadelphia, Pa.; Philadelphia (Pa.): AACR, Cancer Res 2015, 75(15 Suppl):Abstract nr 425. doi:10.1158/1538-7445.AM2015-425; Gravina, Giovanni L. et al., "Dual E-selectin and CXCR4 inhibition reduces tumor growth and increases the sensitivity to docetaxel in experimental bone metastases of prostate cancer [abstract]," Proceedings of the 106th Annual Meeting of the American Association for Cancer Research, 2015 Apr. 18-22, Philadelphia, Pa.; Philadelphia (Pa.): AACR, Cancer Res 2015, 75(15 Suppl): Abstract nr 428. doi:10.1158/1538-7445.AM2015-428, all of which are incorporated by reference.

Synthesis of the compounds of formula II (and substructures, and specific compounds) may be performed as described in U.S. Publication No. US 2017/0305951, which is incorporated herein by reference.

Also provided are pharmaceutical compositions comprising at least one compound of formula (I) and/or formula (II).

Such pharmaceutical compositions are described in greater detail herein. These compounds and compositions may be used in the methods described herein.

In some embodiments, at least one E-selectin antagonist (e.g., a compound of formula (I) or formula (II)) and/or a pharmaceutical composition comprising at least one E-selectin antagonist (e.g., a compound of formula (I) or formula (II)) may be used in methods for releasing MILs out of bone marrow and into circulating blood and enhancing retention of MILs in the blood.

In some embodiments, at least one E-selectin antagonist (e.g., a compound of formula (I) or formula (II)) and/or a pharmaceutical composition comprising at least one E-selectin antagonist (e.g., a compound of formula (I) or formula (II)) may be used in methods described herein for treatment and/or prevention of a cancer. The cancer may be a cancer in which the cancer cells may leave the primary site. A primary site may be, for example, solid tissue (e.g., breast, prostate, or pancreatic) or the bloodstream.

One use of the method is, for example, for MILs harvesting. MILs may be needed, for example, after high-dose chemotherapy treatment. A compound described herein may be used, for example, to release MILs into circulating blood and enhance retention of MILs in the blood. The method may include a further step of collecting MILs that are released. A variety of techniques are known in the art for collecting MILs that have been released into the blood. For example, apheresis may be utilized.

The release of MILs from bone marrow into circulating blood and retention therein has a variety of uses. For example, the mobilized MILs may be collected from the blood. A use of such collected cells is to obtain healthy MILs from an individual prior to treatment of the individual in a manner such that MILs are suppressed. Following treatment, the individual can receive a transplantation utilizing MILs collected prior to treatment. This is useful, for example, where an individual needs to be subjected to a chemotherapy protocol that may damage MILs.

It can be desirable to additionally treat an individual with at least one (i.e., one or more) colony stimulating factor. Such a factor may be administered, for example, before or simultaneous with administration of at least one of the above—described compounds. Where administration is simultaneous, the combination may be administered from a single container or two (or more) separate containers. An example of a suitable colony stimulating factor is G-CSF. G-CSF induces the bone marrow to grow and produce more stem cells. A compound described herein aids in releasing MILs into circulating blood. MILs produced in bone marrow and released into circulating blood, as a result of the combination of the administration (separately or together) of a compound described herein and G-CSF, may be collected as described above. Such collected MILs may be, for example, administered to the individual after chemotherapy. Application of a compound described herein to mobilization and harvesting of healthy MILs from bone marrow treated with G-CSF provides cells useful, for example, for transplantation.

In some embodiments, at least one E-selectin antagonist (e.g., a compound of formula (I) or formula (II)) and/or a pharmaceutical composition comprising at least one E-selectin antagonist (e.g., a compound of formula (I) or formula (II)) may be used in methods described herein for treatment and/or prevention of tumor metastasis. In some embodiments, at least one additional chemotherapy agent such as gemcitabine is administered to the individual.

In some embodiments, at least one E-selectin antagonist (e.g., a compound of formula (I) or formula (II)) and/or a pharmaceutical composition comprising at least one compound of E-selectin antagonist (e.g., a compound of formula (I) or formula (II)) may be used in methods for treatment and/or prevention of an inflammatory disease in which the adhesion or migration of cells occurs in the disease.

Examples of inflammatory diseases include inflammatory skin disorders such as atopic dermatitis and psoriasis. The treatment may reduce (partially or totally) the disease or a complication associated therewith, such as pain. The treatment may be used in conjunction with one or more other therapies for such an inflammatory disease or a complication associated therewith.

In some embodiments, at least one E-selectin antagonist (e.g., a compound of formula (I) or formula (II)) and/or a pharmaceutical composition comprising at least one E-selectin antagonist (e.g., a compound of formula (I) or formula (II)) may be used for treating at least one of the diseases, disorders, and conditions described herein or for the preparation or manufacture of a medicament for use in treating at least one of the diseases, disorders, and/or conditions described herein. Each of these methods and uses is described in greater detail.

In certain embodiments, the methods and E-selectin antagonists described herein are therefore useful for treating hematologic malignancies and metastatic disease, particularly in combination or as an adjunct therapy with chemotherapy and/or radiation therapy.

In some embodiments, at least one E-selectin antagonist (e.g., a compound of formula (I) or formula (II)) and/or a pharmaceutical composition comprising at least one E-selectin antagonist (e.g., a compound of formula (I) or formula (II)) may be used in combination with one or more other agents that mobilize hematopoietic cells. Such agents include, for example, G-CSF; AMD-3100 or other CXCR4 antagonists; GRO-β (CXCL2) and an N-terminal 4-amino truncated form (SB-251353); IL-8SDF-1α peptide analogs, CTCE-0021 and CTCE-0214; and the SDF1 analog, Met-SDF-1β (see, e.g., Pelus, supra and references cited therein). The appropriate therapeutic regimen for administering at least one E-selectin antagonist in combination with another mobilizing agent or agents can be readily determined by a person skilled in the clinical art.

In particular embodiments of the methods described herein, the subject is a human or non-human animal. A subject in need of the treatments described herein may exhibit symptoms or sequelae of cancer disease, disorder, or condition described herein or may be at risk of developing the disease, disorder, or condition. Non-human animals that may be treated include mammals, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

The effectiveness of a compound, agent, or composition described herein in treating or preventing a disease or disorder or condition, and determining and adjusting an appropriate dosing regimen (e.g., adjusting the amount of compound per dose and/or number of doses and frequency of dosing), can readily be determined by a person of ordinary skill in the medical and clinical arts. One or any combination of diagnostic methods, including physical examination, assessment and monitoring of clinical symptoms, and performance of analytical tests and methods described herein, may be used for monitoring the health status of the subject.

Mobilization of MILs can be monitored using methods and techniques routinely practiced in the art the skilled person. MILs may be identified by identifying the presence or absence of certain cell surface markers. For example, the presence and level of MILs can be determined by methods that detect the presence of CD8 or CD4 on the surface of cells (i.e., CD8+ or CD4+ cells).

The compounds described herein may be formulated in a pharmaceutical composition for use in medicaments and therapeutics for mobilizing MILs and for treatment or preventive (or prophylactic) treatment (e.g., reducing the likelihood of occurrence or of exacerbation of a disease, or of one or more symptoms of the disease) of a disease or disorder for which mobilizing MILs is beneficial or for which receiving a MILs transplant or replacement is beneficial. The methods and excipients described herein are exemplary and are in no way limiting.

The dose of an E-selectin antagonist described herein may depend upon the subject's condition, that is, stage of the disease, severity of symptoms caused by the disease, general health status, as well as age, gender, and weight, and other factors apparent to a person of ordinary skill in the medical art. Similarly, the dose of the therapeutic for treating a disease or disorder may be determined according to parameters understood by a person of ordinary skill in the medical art.

Pharmaceutical compositions may be administered in a manner appropriate to the disease or disorder to be treated as determined by persons of ordinary skill in the medical arts. An appropriate dose and a suitable duration and frequency of administration will be determined by such factors as discussed herein, including the condition of the patient, the type and severity of the patient's disease, the particular form of the active ingredient, and the method of administration. In general, an appropriate dose (or effective dose) and treatment regimen provides the pharmaceutical composition(s) as described herein in an amount sufficient to provide therapeutic and/or prophylactic benefit (for example, an improved clinical outcome, such as more frequent complete or partial remissions, or longer disease-free and/or overall survival, or a lessening of symptom severity or other benefit as described in detail above).

The pharmaceutical compositions described herein may be administered to a subject in need thereof by any one of several routes that effectively deliver an effective amount of the compound. Such administrative routes include, for example, topical, oral, nasal, intrathecal, enteral, buccal, sublingual, transdermal, rectal, vaginal, intraocular, subconjunctival, sublingual or parenteral administration, including subcutaneous, intravenous, intramuscular, intrasternal, intracavernous, intrameatal or intraurethral injection or infusion. Compositions administered by these routes of administration and others are described in greater detail herein.

A pharmaceutical composition may be a sterile aqueous or sterile non-aqueous solution, suspension or emulsion, which additionally comprises a physiologically acceptable excipient (pharmaceutically acceptable or suitable excipient or carrier) (i.e., a non-toxic material that does not interfere with the activity of the active ingredient). Such compositions may be in the form of a solid, liquid, or gas (aerosol). Alternatively, compositions described herein may be formulated as a lyophilizate, or compounds and polypeptides or peptides described herein may be encapsulated within liposomes using technology known in the art. Pharmaceutical compositions may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, stabilizers, dyes, flavoring agents, and suspending agents and/or preservatives.

Any suitable excipient or carrier known to those of ordinary skill in the art for use in pharmaceutical compositions may be employed in the compositions described herein. Excipients for therapeutic use are well known, and are described, for example, in Remington: The Science and Practice of Pharmacy (Gennaro, 21st Ed. Mack Pub. Co., Easton, Pa. (2005)). In general, the type of excipient is selected based on the mode of administration, as well as the chemical composition of the active ingredient(s). Pharmaceutical compositions may be formulated for any appropriate manner of administration, including, for example, topical, oral, nasal, intrathecal, enteral, buccal, sublingual, transdermal, rectal, vaginal, intraocular, subconjunctival, sublingual or parenteral administration, including subcutaneous, intravenous, intramuscular, intrasternal, intracavernous, intrameatal or intraurethral injection or infusion. For parenteral administration, the carrier preferably comprises water, saline, alcohol, a fat, a wax or a buffer. For oral administration, any of the above excipients or a solid excipient or carrier, such as mannitol, lactose, starch, magnesium stearate, sodium saccharine, talcum, cellulose, kaolin, glycerin, starch dextrins, sodium alginate, carboxymethylcellulose, ethyl cellulose, glucose, sucrose and/or magnesium carbonate, may be employed.

A pharmaceutical composition (e.g., for oral administration or delivery by injection) may be in the form of a liquid. A liquid pharmaceutical composition may include, for example, one or more of the following: a sterile diluent such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

For oral formulations, at least one E-selectin antagonist described herein can be used alone or in combination with appropriate additives to make tablets, powders, granules or capsules, for example, with any one or more conventional additives, disintegrators, lubricants, and if desired, diluents, buffering agents, moistening agents, preservatives, coloring agents, and flavoring agents. The compositions may be formulated to include a buffering agent to provide for protection of the active ingredient from low pH of the gastric environment and/or an enteric coating. A composition may be formulated for oral delivery with a flavoring agent, e.g., in a liquid, solid or semi-solid formulation and/or with an enteric coating.

Oral formulations may be provided as gelatin capsules, which may contain the active compound or biological along with powdered carriers. Similar carriers and diluents may be used to make compressed tablets. Tablets and capsules can be manufactured as sustained release products to provide for continuous release of active ingredients over a period of time. Compressed tablets can be sugar coated or film coated to mask any unpleasant taste and protect the tablet from the atmosphere, or enteric coated for selective disintegration in the gastrointestinal tract.

A pharmaceutical composition may be formulated for sustained or slow release. Such compositions may generally be prepared using well known technology and administered by, for example, oral, rectal or subcutaneous implantation, or by implantation at the desired target site. Sustained-release formulations may contain the active therapeutic dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active therapeutic contained within a sustained release formulation depends upon the site of implantation, the rate and expected duration of release, and the nature of the condition to be treated or prevented.

The pharmaceutical compositions described herein can be formulated as suppositories by mixing with a variety of bases such as emulsifying bases or water-soluble bases. The pharmaceutical compositions may be prepared as aerosol formulations to be administered via inhalation. The compositions may be formulated into pressurized acceptable propellants such as dichlorodifluoromethane, propane, nitrogen and the like.

The at least one E-selectin antagonist may be administered topically (e.g., by transdermal administration). Topical formulations may be in the form of a transdermal patch, ointment, paste, lotion, cream, gel, and the like. Topical formulations may include one or more of a penetrating agent or enhancer (also call permeation enhancer), thickener, diluent, emulsifier, dispersing aid, or binder. Physical penetration enhancers include, for example, electrophoretic techniques such as iontophoresis, use of ultrasound (or "phonophoresis"), and the like. Chemical penetration enhancers are agents administered either prior to, with, or immediately following administration of the therapeutic, which increase the permeability of the skin, particularly the stratum corneum, to provide for enhanced penetration of the drug through the skin. Additional chemical and physical penetration enhancers are described in, for example, Transdermal Delivery of Drugs, A. F. Kydonieus (ED) 1987 CRL Press; Percutaneous Penetration Enhancers, eds. Smith et al. (CRC Press, 1995); Lenneras et al., J. Pharm. Pharmacol. 54:499-508 (2002); Karande et al., Pharm. Res. 19:655-60 (2002); Vaddi et al., Int. J. Pharm. 91:1639-51 (2002); Ventura et al., J. Drug Target 9:379-93 (2001); Shokri et al., Int. J. Pharm. 228(1-2):99-107 (2001); Suzuki et al., Biol. Pharm. Bull. 24:698-700 (2001); Alberti et al., J. Control Release 71:319-27 (2001); Goldstein et al., Urology 57:301-5 (2001); Kiijavainen et al., Eur. J. Pharm. Sci. 10:97-102 (2000); and Tenjarla et al., Int. J. Pharm. 192: 147-58 (1999).

Routes of administration include, but are not limited to, intradermal, intramuscular, intraperitoneal, intravenous, intrathecal, and subcutaneous routes. In some embodiments, the compounds or compositions are administered locally (i.e., near a cancer tumor). In some embodiments, one or more of the compounds or compositions are administered using different routes of administration.

The compounds or pharmaceutical composition(s) can be administered in one or more doses and treatment regimens, which may be the same or different. In some embodiments, each of the compounds or pharmaceutical composition(s) is administered in an amount ranging from about 1 mg/kg to about 50 mg/kg once a day. In other embodiments, the dosage may be at any dosage including, but not limited to, about 1 µg/kg, 25 µg/kg, 50 µg/kg, 75 µg/kg, 100 µg/kg, 125 µg/kg, 150 µg/kg, 175 µg/kg, 200 µg/kg, 225 µg/kg, 250 µg/kg, 275 µg/kg, 300 µg/kg, 325 µg/kg, 350 µg/kg, 375 µg/kg, 400 µg/kg, 425 µg/kg, 450 µg/kg, 475 µg/kg, 500 µg/kg, 525 µg/kg, 550 µg/kg, 575 µg/kg, 600 µg/kg, 625 µg/kg, 650 µg/kg, 675 µg/kg, 700 µg/kg, 725 µg/kg, 750 µg/kg, 775 µg/kg, 800 µg/kg, 825 µg/kg, 850 µg/kg, 875 µg/kg, 900 µg/kg, 925 µg/kg, 950 µg/kg, 975 µg/kg, 1 mg/kg, 2 mg/kg, 3 mg/kg, 4 mg/kg, 5 mg/kg, 6 mg/kg, 7 mg/kg, 8 mg/kg, 9 mg/kg, or 10 mg/kg.

In some embodiments, the compounds or pharmaceutical composition(s) are administered in any of these amounts and ranges once a day, more than once a day, every other day, every two days, etc. One of more treatment cycles may be repeated, and any number of cycles is contemplated. The number of treatments per day and the amount per dose for each compound or pharmaceutical composition may vary during each cycle.

Kits with unit doses of one or more of the compounds, polypeptides, peptides, aptamers, antibodies and antigen binding fragments thereof described herein, usually in oral or injectable doses, are provided. Such kits may include a container containing the unit dose, an informational package insert describing the use and attendant benefits of the therapeutic in treating the pathological condition of interest, and optionally an appliance or device for delivery of the composition.

The following examples provide illustrative embodiments of the invention. One of ordinary skill in the art will recognize the numerous modifications and variations that may be performed without altering the spirit or scope of the present invention. Such modifications and variations are encompassed within the scope of the invention. The Examples do not in any way limit the invention.

EXAMPLES

In the disclosed examples, the following materials and methods were used.

Chemicals: GMI-1271 (100% parent, >97% purity) was obtained as a white, crystalline substance. It was stored protected from light at −20° C. The compound was formulated in sterile phosphate buffered saline (PBS), resulting in a clear, colorless solution with a pH value of 7.4 and a concentration of 4 mg/mL. The dosing solution was prepared 12 hours prior to the first dose and stored at 4° C. protected from light between treatments.

GMI-1359 (100% parent, >97% purity) was obtained as a white, granular powder. It was stored protected from light at −20° C. The compound was formulated in sterile (PBS), resulting in a clear, colorless solution with a pH value of 9.2 and a concentration of 4 mg/mL. The dosing solution was prepared 12 hours prior to the first dose and stored at 4° C. protected from light between treatments.

G-CSF (0.3 mg/mL) was obtained as a clear, colorless stock solution. It was stored protected from light and at 4° C. The dosing solution was prepared by diluting the stock solution with 5% dextrose. The result was a clear, colorless solution with a pH value of 4.8 and a concentration of 0.0128 mg/mL. The dosing formulation was prepared daily and was stored at room temperature and protected from light, between treatments.

Anti-CTLA-4 (7.36 mg/mL) was obtained as a clear, colorless stock solution. It was stored protected from light and at 4° C. The dosing solution was prepared by diluting the stock solution with PBS. The result was a clear, colorless solution with a pH value of 7 and a concentration of 1 mg/mL. The dosing formulation was prepared fresh weekly and stored at 4° C. and protected from light between treatments.

Animals and Husbandry: Female Envigo Balb/c mice (BALB/cAnNHsd) were used in this study. They were 6-7 weeks old on Day 1 of the experiment. The animals were fed irradiated Harlan 2918.15 Rodent Diet and water ad libitum. Animals were housed in Innovive disposable ventilated caging with corn cob bedding inside Biobubble® Clean Rooms that provide H.E.P.A filtered air into the bubble environment at 100 complete air changes per hour. All treatments, body weight determinations, and tumor measurements were carried out in the bubble environment. The environment was controlled to a temperature range of 70°±2° F. and a humidity range of 30-70%.

Cancer Cell Preparation: CT26WT cells were obtained. They were grown in RPMI 1640 medium which was modified with 1% 100 mM Na pyruvate, 1% 1M HEPES buffer, 1% of a 45% glucose solution and supplemented with 10% non-heat-inactivated Fetal Bovine Serum (FBS) and 1% 100× Penicillin/Streptomycin/L-Glutamine (PSG). The growth environment was maintained in an incubator with a 5% CO2 atmosphere at 37° C. When expansion was complete, the cells (passage 3) were trypsinized using 0.25% trypsin-EDTA solution following cell detachment, the trypsin was inactivated by dilution with complete growth medium and any clumps of cells were separated by pipetting. The cells were centrifuged at 200rcf for 8 minutes at 4° C., the supernatant was aspirated, and the pellet was re-suspended in cold Dulbecco's Phosphate Buffered Saline (DPBS) by pipetting. An aliquot of the homogeneous cell suspension was diluted in a trypan blue solution and counted using a Luna automated cell counter. The pre-implantation cell viability was 93%. The cell suspension was centrifuged at 200rcf for 8 minutes at 4° C. The supernatant was aspirated and the cell pellet was re-suspended in cold serum-free medium to generate a final concentration of 2.50E+06 trypan-excluding cells/mL. The cell suspension was maintained on wet ice during implantation.

Following implantation, an aliquot of the remaining cells was diluted with a trypan blue solution and counted to determine the post-implantation cell viability (92%).

Test animals in were implanted subcutaneously, high in the axilla (just under the fore limb) on Day 0 with 5.0E+05 cells in 0.2 mL of serum-free medium using a 27-gauge needle and syringe.

Protocol for Detection and Mobilization of MILs in the CT-26 tumor model: GMI-1271 is a potent, small-molecule, glycomimetic antagonist of E-selectin. GMI-1359 is a potent, small-molecule glycomimetic dual antagonist, targeting E-selectin and CXCR4. The effects of inhibiting either E-selectin with GMI-1271 or E-selectin and CXCR4 with GMI-1359 on MIL mobilization was tested in BALB/c mice that had been induced to reject the syngeneic CT26 colon carcinoma via anti-CTLA-4 T cell checkpoint antibody. The experimental protocol is summarized in Table 1.

TABLE 1

| Group | Treatment Regimen | Parameters (12 hrs post final dose) |
|---|---|---|
| Tumor immune, saline | 10 mL/kg IP bid × 3 d | PB & BM CD8+ phenotype |
| Tumor immune, GMI-1271 | 40 mgkg$^{-1}$ IP bid × 3 d | Tumor specific PB & BM in vitro responses: defined as CD8+/IFNγ$^+$ following tumor pulse |
| Tumor immune, GMI-1359 | 40 mgkg$^{-1}$ IP bid × 3 d | |

TABLE 1-continued

| Group | Treatment Regimen | Parameters (12 hrs post final dose) |
|---|---|---|
| Tumor immune, G-CSF | 0.125 mgkg$^{-1}$ SC bid × 3 d | |
| Non-immune, saline | 10 mL/kg IP bid × 3 d | |

Treatment with anti-CTLA-4 for all mice implanted with CT26.WT began on Day 3. All mice were dosed intraperitoneally on Days 3, 6, 10, 13, and 17. All mice were dosed according to individual body weight on the day of treatment (0.2 mg/20 g).

On Day 25, mice without tumors following CTLA-4 treatment were distributed into the four "Tumor Immune" treatment groups indicated in Table 1 such that the mean body weight within each group was within 10% of the overall mean.

Treatment for "Tumor Immune" groups 1-4 began on Day 25. The Vehicle was dosed intraperitoneally every 12 hours for 3 days (Days 25-27). GMI-1271 and GMI-1359 were dosed intraperitoneally at 40 mg/kg every 12 hours for 3 days (Days 25-27). G-CSF was dosed at 0.125 mg/kg subcutaneously every 12 hours for 3 days (Days 25-27).

A "Nonimmune" group 5 was populated with age-matched, naive non-tumor bearing mice.

At 12 hours after the final dose of test agents, all mice in groups 1-5 (treatment "Tumor Immune" groups 1-4 and control "Nonimmune" group 5) were euthanized for blood and bone marrow collection.

Flow cytometric analysis was used to determine CD62L and CD44 expression on CD8+ T cells in whole blood and bone marrow samples. Secondary analysis included AH-1 Dextramer analysis on the three tissue types and IFNγ production in pooled blood and bone marrow samples. Samples were acquired using a 4 laser, 14 color Attune NxT Flow Cytometer with autosampler. CD62L and CD44 events were gated on CDS+ T cells.

Results

The distribution of CD8+ T cells in CT26 immune mice following administration of GMI-1271, GMI-1359, or G-CSF was analyzed. As shown in FIGS. 1A-1C, the phenotypes of CD8+ T cells were determined in the peripheral blood and bone marrow samples. The data shows that, in contrast to G-CSF, treatment with GMI-1271 and GMI-1359 mobilized both naïve (FIG. 1A) and central memory (CM) CD8+ T cells (FIG. 1B) into the peripheral blood. Redistribution of effector memory (EM) CD8+ T cells was not effected by GMI-1271 or GMI-1359 (FIG. 1C).

The percent of CD8+ lymphocytes in bone marrow armed to produce IFNγ in the test subjects was also tested. As shown in FIG. 2, the functional activity of the CD8+ MILs was assessed by IFNγ production following in vitro stimulation with irradiated CT-26 tumor cells, the immunodominant CT-26 tumor antigen (AH1), or saline (unstimulated). MILs from tumor immunized mice treated with saline, GMI-1271, and GMI-1359 were primed to respond to both AH1 and whole tumor cells. Unstimulated MILs from tumor immune mice or stimulated CD8+ T-cells from non-immune mice did not produce IFNγ.

Figure 3:
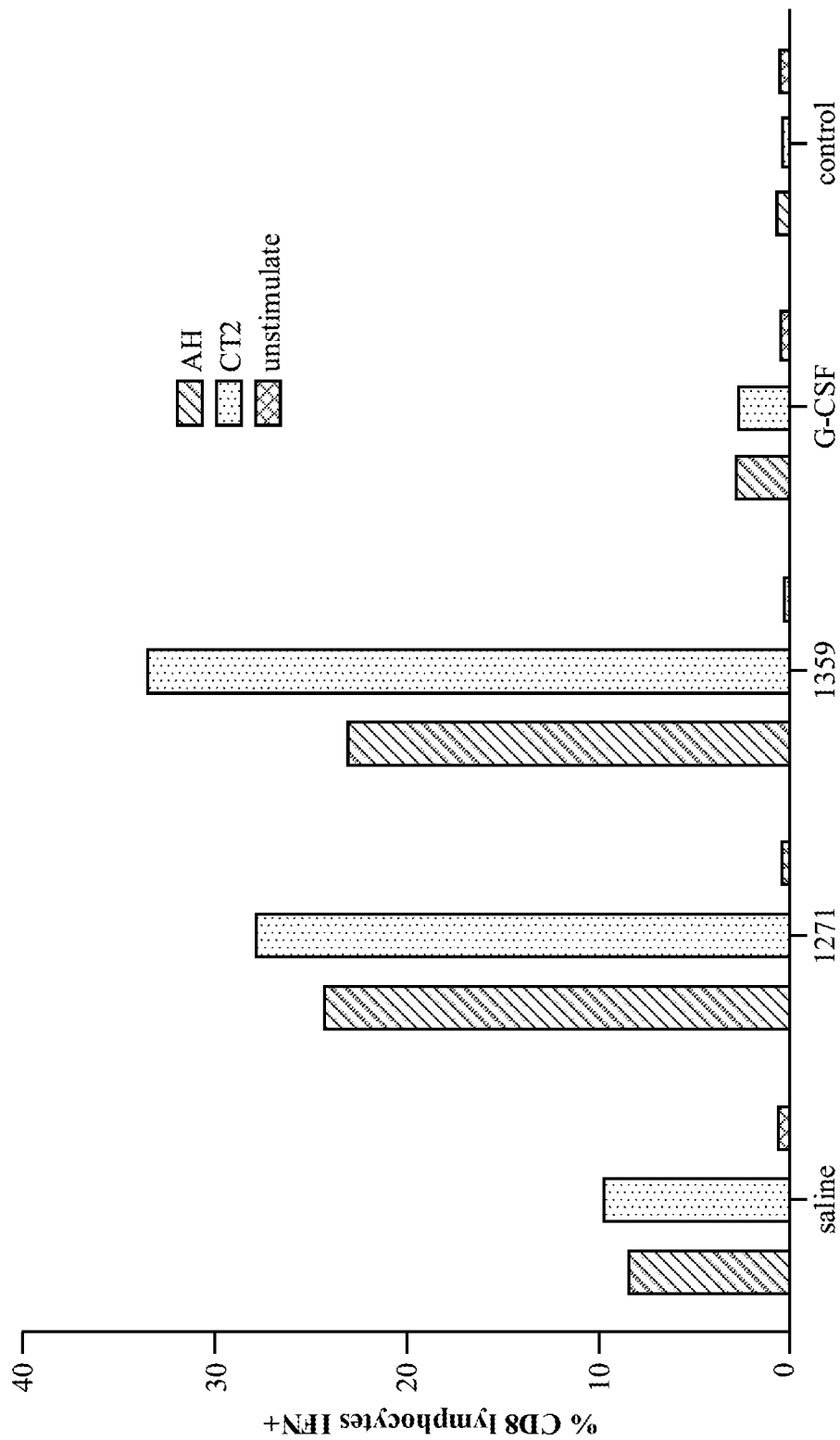
FIG. 3 is an exemplary graph of the percentage of IFN+ lymphocytes in the population of CD8+ lymphocytes from peripheral blood samples taken from CT26 non-immune mice acting as controls and in CT26 immune mice following administration of GMI-1271, GMI-1359, G-CSF, or saline.

The percent of CD8+ lymphocytes in peripheral blood armed to produce IFNγ was tested as well. FIG. 3 illustrates that the percentage of CD8+ T-cells in peripheral blood primed to produce IFNγ was markedly increased following treatment with GMI-1271 or GMI-1359 but not saline or G-CSF. Without being bound to theory, applicant understands that these results are likely due to a redistribution of tumor-primed MILs into the blood compartment.

Thus, the experimental results here highlight a unique use of E-selectin antagonists, such as GMI-1271 (a compound of formula (I)) and GMI-1359 (a compound of formula (II)).

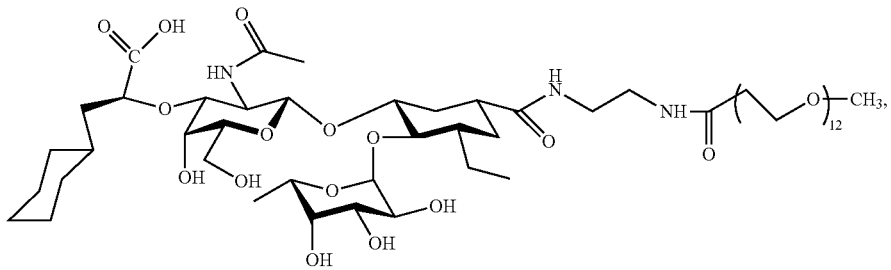

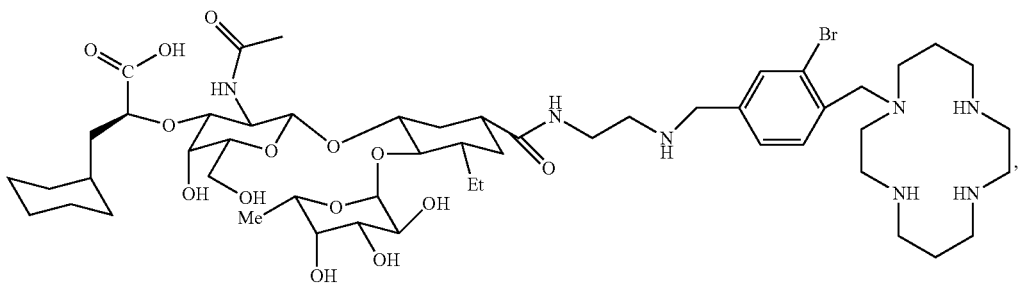

The administration of E-selectin antagonists results in mobilization or redistribution of tumor-primed MILs into peripheral blood.

The various embodiments described above can be combined to provide further embodiments. All U.S. patents, U.S. patent application publications, U.S. patent applications, non-U.S. patents, non-U.S. patent applications, and non-patent publications referred to in this specification and/or listed in the Application Data Sheet are incorporated herein by reference, in their entirety. Aspects of the embodiments can be modified, if necessary, to employ concepts of the various patents, applications, and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

14. The method of claim 1, wherein the at least one E-selectin antagonist is
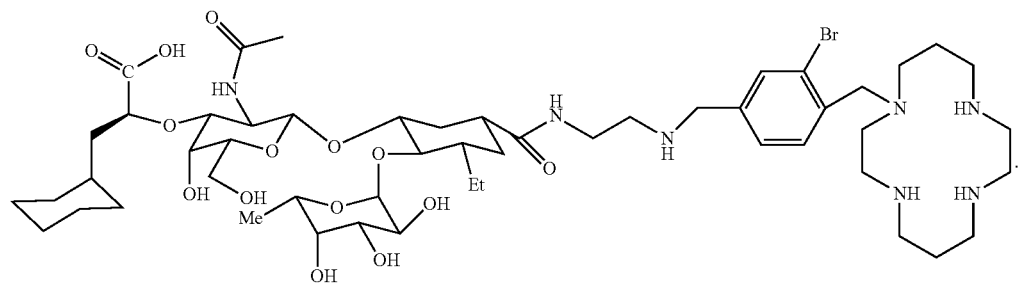

What is claimed is:

1. A method of treating cancer and/or preventing a cancer relapse, wherein the method comprises:
   administering to a donor patient at least one E-selectin antagonist, wherein the amount of E-selectin antagonist administered is sufficient to mobilize MILs of the donor patient into the peripheral blood;
   recovering MILs from the peripheral blood of the donor patient; and
   transplanting at least a portion of the recovered MIL cell population to the donor patient or a second patient;
   wherein the at least one E-selectin antagonist is chosen from and pharmaceutically acceptable salts of either of the foregoing; and
   wherein the at least one E-selectin antagonist is not used in combination with other agents used to mobilize hematopoietic stem cells.

2. The method of claim 1, wherein the recovered MILs are expanded ex vivo before transplantation.

3. The method of claim 1, wherein the at least one E-selectin antagonist is in the form of a pharmaceutical composition.

4. The method of claim 3, wherein said pharmaceutical composition further comprises at least one additional pharmaceutically acceptable ingredient.

5. The method of claim 1, wherein the patient receiving the transplantation of the at least a portion of the recovered MIL cell population has received or will receive chemotherapy and/or radiotherapy.

6. The method of claim 5, wherein the chemotherapy comprises administration of bortexomib and/or gemcitabine.

7. The method of claim 1, wherein the cancer is a hematologic cancer.

8. The method of claim 1, wherein the cancer is a solid cancer.

9. The method of claim 1, wherein the cancer is a liquid cancer.

10. The method of claim 1, wherein the donor patient has been diagnosed with a first type of cancer and the cancer for which the method is performed to treat and/or prevent a relapse thereof is a second type of cancer.

11. The method of claim 1, wherein the at least one E-selectin antagonist is chosen from
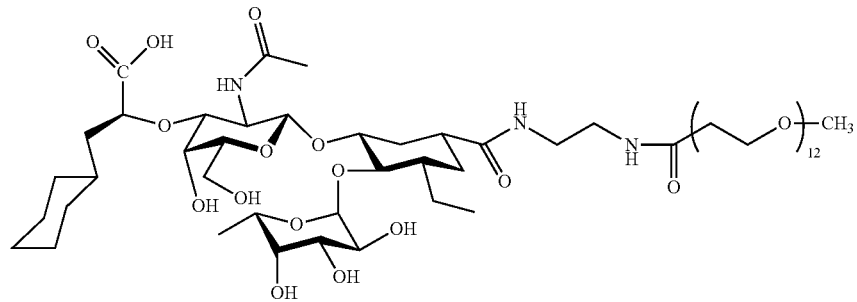
and pharmaceutically acceptable salts thereof.
12. The method of claim 1, wherein the at least one E-selectin antagonist is
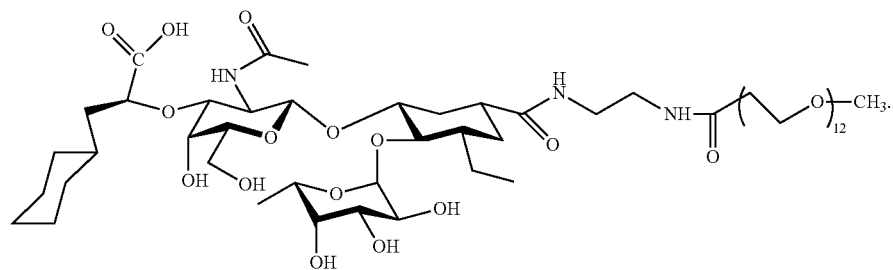
13. The method of claim 1, wherein the at least one E-selectin antagonist is chosen from
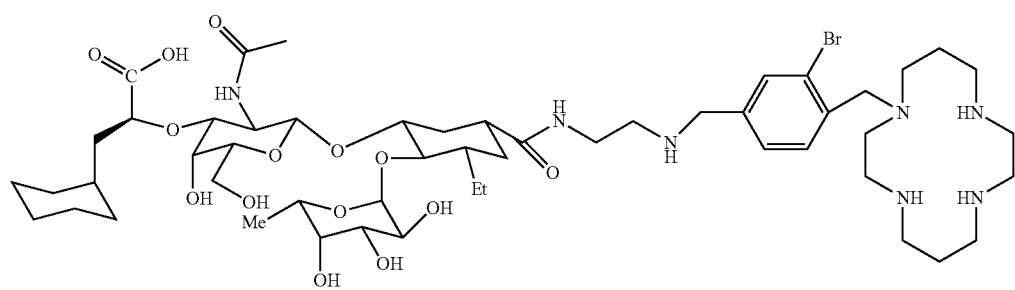 [SMILES: CCC1CC(C(=O)NCCNCc2ccc(CN3CCCNCCNCCCNCC3)c(Br)c2)CC(OC2OC(CO)C(O)C(O[C@@H](CC3CCCCC3)C(=O)O)C2NC(C)=O)C1OC1OC(C)C(O)C(O)C1O]
and pharmaceutically acceptable salts thereof.